US008299217B2

(12) United States Patent
Heinrichs

(10) Patent No.: US 8,299,217 B2
(45) Date of Patent: Oct. 30, 2012

(54) VARIANT AXMI-R1 DELTA ENDOTOXIN GENES AND METHODS FOR THEIR USE

(75) Inventor: Volker Heinrichs, Raleigh, NC (US)

(73) Assignee: Athenix Corp., Research Triangle Park, NC (US)

( * ) Notice: Subject to any disclaimer, the term of this patent is extended or adjusted under 35 U.S.C. 154(b) by 232 days.

(21) Appl. No.: 12/701,058

(22) Filed: Feb. 5, 2010

(65) Prior Publication Data

US 2010/0197592 A1 Aug. 5, 2010

Related U.S. Application Data

(60) Provisional application No. 61/150,309, filed on Feb. 5, 2009, provisional application No. 61/229,567, filed on Jul. 29, 2009.

(51) Int. Cl.
*C07K 14/235* (2006.01)
*A01N 37/44* (2006.01)
*A01P 7/04* (2006.01)

(52) U.S. Cl. ............... 530/350; 514/12; 536/23.71

(58) Field of Classification Search .............. 514/12; 530/350; 536/23.71
See application file for complete search history.

(56) References Cited

U.S. PATENT DOCUMENTS

| 4,764,372 A | 8/1988 | Herrnstadt et al. |
| 4,771,131 A | 9/1988 | Herrnstadt et al. |
| 4,797,276 A | 1/1989 | Herrnstadt et al. |
| 4,853,331 A | 8/1989 | Herrnstadt et al. |
| 4,865,981 A | 9/1989 | Herrnstadt et al. |
| 4,910,136 A | 3/1990 | Herrnstadt et al. |
| 5,002,765 A | 3/1991 | Herrnstadt et al. |
| 5,017,373 A | 5/1991 | Herrnstadt et al. |
| 5,349,124 A | 9/1994 | Fischhoff et al. |
| 5,495,071 A | 2/1996 | Fischhoff et al. |
| 5,659,123 A | 8/1997 | Van Rie et al. |
| 5,763,241 A | 6/1998 | Fischhoff et al. |
| 6,023,013 A | 2/2000 | English et al. |
| 6,077,824 A | 6/2000 | English et al. |
| 6,284,949 B1 | 9/2001 | Fischhoff et al. |
| 6,620,988 B1 | 9/2003 | English et al. |
| 6,953,835 B2 | 10/2005 | Fischhoff et al. |
| 7,030,295 B2 | 4/2006 | Chen et al. |
| 7,227,056 B2 | 6/2007 | English et al. |
| 7,230,167 B2 | 6/2007 | Chen et al. |
| 7,276,583 B2 | 10/2007 | Chen et al. |

FOREIGN PATENT DOCUMENTS

WO 03018810 A2 3/2003

OTHER PUBLICATIONS

Schnepf E. et al, "*Bacillus thuringiensis* and It's Pesticidal Crystal Proteins", Reviews, American Society for Microbiology, US, vol. 62, No. 3, Sep. 1, 1998, pp. 775-806, EX000986964, ISSN: 1092-2172, pp. 788-789.
Park H-W et al, "Effect of specific mutations in helix [alpha]7 of domain I on the stability and crystallization of Cry3A in *Bacillus thuringiensis*", Molecular Biotechnology, Humana Press, Inc, US, vol. 27, No. 2, Jan. 1, 2004, XP002526267, ISSN: 1073-6085.
Invitation to Pay Addition Fees with Communication Relating to the Search Results of the Partial International Search mailed Apr. 15, 2010.
Carroll et al. (1989) *Biochem J.* 261:99-105.
Carroll et al. (1997) *Journal of Invertebrate Biology* 70:41-49.
Donovan et al. (1988) *Mol. Gen. Genet.* 214(3):365-372.
Hernstadt et al. (1987) *Gene* 57:37-46.
Hofte et al. (1987) *Nucleic Acids Research* 15:7183.
McPherson et al. (1988) *Bio/Technology* 6:61-66.
Sekar et al. (1987) *Proc. Natl. Acad. Sci. USA* 84: 7036-7040.
Walters et al. (2008) *Applied and Environ. Micro.* 74: 367-374.
Wu and Dean (1996) *J. Mol. Biol.* 255:628-640.
Wu et al (2000) *FEBS Letters* 473:227-232.
GenBank Accession No. P0A379, submitted on Mar. 15, 2005.

*Primary Examiner* — Chih-Min Kam

(57) ABSTRACT

Compositions and methods for conferring pesticidal activity to bacteria, plants, plant cells, tissues and seeds are provided. Compositions comprising a coding sequence for pesticidal polypeptides are provided. The coding sequences can be used in DNA constructs or expression cassettes for transformation and expression in plants and bacteria. Compositions also comprise transformed bacteria, plants, plant cells, tissues, and seeds. In particular, nucleic acid molecules encoding variant AXMI-R1 sequences are provided. Additionally, amino acid sequences corresponding to the polynucleotides are encompassed.

12 Claims, 2 Drawing Sheets

DI
MNPNNRSEHDTIKTTENNEVPTNHVQYPLAETPNPTLEDLNYKEFLRMTADNNTEALDSSTTKDVIQ

KGISVVGDLLGVVGFPFGGALVSFYTNFLNTIWPSEDPWKAFMEQVEALMDQKIADYAKNKALÆL
                           ↓154           ↓160
QGLQNNVEDYVSALSSWQKNPVSSRNPHSQGRIRELFSQAESHFRNSMPSFAISGYEVLFLTTYAQ

AANTHLFLLKDAQIYGEEWGYEKEDIAEFYKRQLKLTQEYTDHCVKWYNVGLDKLRGSSYESWWN
                         | DII                         ↓398
FNRYRREMTLTVLDLIALFPLYDVRLYPKEVKTELTRDVLTDPIVGVNNLRGYGTTFSNIENYRKPHL

FDYLHRIQFHTRFQPGYYGNDSFNYWSGNYVSTRPSIGSNDIITSPFYGNKSSEPVQNLEFNGBKVY
        L1
RAVANTNLAVWPSAVYSGVTKVEFSQYNDQTDEASTQTYDSKRNVGAVSWDSIDQLPPETTDER
    L2                                      | DIII
EKGYSHQLNYVMCFLMQGSRGTIPVLTWTHKSVDFFNMIDSKKITQLPLVKAYKLQSGASVVAQPR
               L3
FTGGDIIQCTENGSAATIYVTPDVSYSQKYRARIHYASTSQITFTLSLDGAPFNQYYFDKTINIGDTLT

YNSFNLASFSTPFELSGNNLQIGVTGLSAGDKVYIDKIEFIPVN

Figure 1

| | 187 | | | | 210 | 220 | 230 |
|---|---|---|---|---|---|---|---|
| Axmi164 (187) | --EYARNK | LTE | KGLGDAIDV | QESLEA | IENRNDT | ----RARSVVSK |
| Axmi161 (128) | --ESFRNE | ISK | NGLADIYTV | LSELELI | IEHPHDP | ----SIIQSVRT |
| Axmi152 (116) | --NYAREK | ITE | EGLGNWKD | RSKLQQ | IDTKRSLKH | |
| Axmi151 (119) | --KAVRSR | ISE | EGIHQVYRI | IEALNE | IPDTPDNP | ----FVQERVRT |
| Axmi146 (119) | --EQVRND | LAT | ESSGIALQA | LNAALED | ITNENNAR | ----STQLVRE |
| Axmi141 (126) | --EYARNI | LTN | KGLENSYKI | LEALADL | KQNPTSP | ----SSQERVRT |
| Axmi129 (128) | --BAVRNK | LAD | ANSGRALQS | LNAFELQ | RNENIER | ----SKELVRE |
| Axmi128 (80) | --BYARNI | LTH | KGLENSYKI | LEALAD | IQNPTSP | ----SSQERVRT |
| Axmi127 (127) | --ANVRSQ | IAK | EGLGRGLBA | QEILVA | IENRNNA | ----RTRSIIKQ |
| Axmi120 (126) | --ESTRKL | IAR | QGLGAASEV | QESLES | IENQNDAR | ----AMSVVRQ |
| Axmi116 (14) | --BAVRSR | LSE | EGLQRIYSS | QSDLER | IGDRDNP | ----EYQEIIRQ |
| Axmi114 (155) | END DVVID | DNK | EGLANTLDI | LEALKE | INDPQNP | ----ASQERVRT |
| Axmi101 (95) | --AYAKSR | LTD | VSIGNAVEF | QTALED | EKQEEN | ----IKSLGLVIQ |
| Axmi091 (145) | --AFAREQ | LRQ | EGLGNLGI | KEALAE | PQORDNP | ----TTIKERVRT |
| Axmi087 (129) | --EYARNK | IAE | TGLGNAMDV | QSSLED | VANPNDA | ----RTRSVVAT |
| Axmi037 (129) | --EQVELD | LTE | EKTGEAVEA | YIALDL | EPVFEDM | ----FBLSEVIK |
| Axmi029 (146) | --QQVIID | ETA | ESVKLNVDI | LNAFEE | EKRPTNE | ----YSTELVYK |
| Axmi028 (80) | ED DEVVKD | NTI | KGINGSLNI | PRDPNNL | TTIENVTD | |
| Cry6Ba1 (96) | --EYARNK | LSE | EGLGNNYQI | LTAEEE | EENPNGS | ----RALRDVRN |
| Cry6Bc1 (129) | --BYARNK | LSE | EGLGNNYQI | LITALEE | EENPNGS | ----RALRDVRN |
| Cry2Aa (129) | --EYVRNK | LAE | DSLGSALDR | QKALALD | GRQDDP | ----EAILSVAT |
| axmiR1_permutP3c-7 (117) | --DYARNK | LAE | DGLQNNVEI | VSAISS | CRNAKSSRNMHSQGRIRE | |
| axmi-R1 (123) | --DYARNK | LAE | DGLQNNVEL | VSALSS | CRNPVSSRNEHSQGRIRE | |

Figure 2

SEQUENCE LISTING

```
<160> NUMBER OF SEQ ID NOS: 64

<210> SEQ ID NO 1
<211> LENGTH: 1935
<212> TYPE: DNA
<213> ORGANISM: Bacillus thuringiensis

<400> SEQUENCE: 1
atgaatccga acaatcgaag tgaacatgat acaataaaaa ctactgaaaa taatgaggtg     60
ccaactaacc atgttcaata tcctttagcg gaaactccaa atccaacact agaagattta    120
aattataaag agtttttaag aatgactgca gataataata cggaagcact agatagctct    180
acaacaaaag atgtcattca aaaaggcatt tccgtagtag gtgatctcct aggcgtagta    240
ggtttcccgt ttggtggagc gcttgtttcg ttttatacaa actttttaaa tactatttgg    300
ccaagtgaag acccgtggaa ggcttttatg gaacaagtag aagcattgat ggatcagaaa    360
atagctgatt atgcaaaaaa taaagctctt gcagagttac agggccttca aaataatgtc    420
gaagattatg tgagtgcatt gagttcatgg caaaaaaatc ctgtgagttc acgaaatcca    480
catagccagg ggcggataag agagctgttt tctcaagcag aaagtcattt tcgtaattca    540
atgccttcgt ttgcaatttc tggatacgag gttctatttc taacaacata tgcacaagct    600
gccaacacac atttattttt actaaaagac gctcaaattt atggagaaga atggggatac    660
gaaaaagaag atattgctga attttataaa agacaactaa aacttacgca agaatatact    720
gaccattgtg tcaaatggta taatgttgga ttagataaat taagaggttc atcttatgaa    780
tcttgggtaa actttaaccg ttatcgcaga gagatgacat taacagtatt agatttaatt    840
gcactatttc cattgtatga tgttcggcta tacccaaaag aagttaaaac cgaattaaca    900
```

```
agagacgttt taacagatcc aattgtcgga gtcaacaacc ttaggggcta tggaacaacc    960
ttctctaata tagaaaatta tattcgaaaa ccacatctat ttgactatct gcatagaatt   1020
caatttcaca cgcggttcca accaggatat tatggaaatg actctttcaa ttattggtcc   1080
ggtaattatg tttcaactag accaagcata ggatcaaatg atataatcac atctccattc   1140
tatggaaata atccagtga acctgtacaa aatttagaat ttaatggaga aaaagtctat    1200
agagccgtag caaatacaaa tcttgcggtc tggccgtccg ctgtatattc aggtgttaca   1260
aaagtggaat ttagccaata taatgatcaa acagatgaag caagtacaca aacgtacgac   1320
tcaaaaagaa atgttggcgc ggtcagctgg gattctatcg atcaattgcc tccagaaaca   1380
acagatgaac ctctagaaaa gggatatagc catcaactca attatgtaat gtgcttttta   1440
atgcagggta gtagaggaac aatcccagtg ttaacttgga cacataaaag tgtagacttt   1500
tttaacatga ttgattcgaa aaaaattaca caacttccgt tagtaaaggc atataagtta   1560
caatctggtg cttccgttgt cgcaggtcct aggtttacag gagagatat cattcaatgc    1620
acagaaaatg gaagtgcggc aactatttac gttacaccgg atgtgtcgta ctctcaaaaa   1680
tatcgagcta gaattcatta tgcttctaca tctcagataa catttacact cagtttagac   1740
ggggcaccat ttaatcaata ctatttcgat aaaacgataa ataaaggaga cacattaacg   1800
tataattcat ttaatttagc aagtttcagc acaccattcg aattatcagg gaataactta   1860
caaataggcg tcacaggatt aagtgctgga gataaagttt atatagacaa aattgaattt   1920
attccagtga attag                                                    1935

<210> SEQ ID NO 2
<211> LENGTH: 644
<212> TYPE: PRT
<213> ORGANISM: Bacillus thuringiensis

<400> SEQUENCE: 2

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
             20                  25                  30

Pro Asn Pro Thr Leu Glu Asp Leu Asn Tyr Lys Glu Phe Leu Arg Met
         35                  40                  45

Thr Ala Asp Asn Asn Thr Glu Ala Leu Asp Ser Ser Thr Thr Lys Asp
     50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190
```

```
Phe Leu Thr Thr Tyr Ala Gln Ala Asn Thr His Leu Phe Leu Leu
        195                 200                 205
Lys Asp Ala Gln Ile Tyr Gly Glu Glu Trp Gly Tyr Glu Lys Glu Asp
    210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
                245                 250                 255
Ser Ser Tyr Glu Ser Trp Val Asn Phe Asn Arg Tyr Arg Arg Glu Met
            260                 265                 270
Thr Leu Thr Val Leu Asp Leu Ile Ala Leu Phe Pro Leu Tyr Asp Val
        275                 280                 285
Arg Leu Tyr Pro Lys Glu Val Lys Thr Glu Leu Thr Arg Asp Val Leu
    290                 295                 300
Thr Asp Pro Ile Val Gly Val Asn Asn Leu Arg Gly Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
        355                 360                 365
Ser Ile Gly Ser Asn Asp Ile Ile Thr Ser Pro Phe Tyr Gly Asn Lys
    370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
        435                 440                 445
Ser Trp Asp Ser Ile Asp Gln Leu Pro Pro Glu Thr Thr Asp Glu Pro
    450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
            500                 505                 510
Pro Leu Val Lys Ala Tyr Lys Leu Gln Ser Gly Ala Ser Val Val Ala
        515                 520                 525
Gly Pro Arg Phe Thr Gly Gly Asp Ile Ile Gln Cys Thr Glu Asn Gly
    530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
            580                 585                 590
Ile Asn Lys Gly Asp Thr Leu Thr Tyr Asn Ser Phe Asn Leu Ala Ser
        595                 600                 605
Phe Ser Thr Pro Phe Glu Leu Ser Gly Asn Asn Leu Gln Ile Gly Val
    610                 615                 620
```

Thr Gly Leu Ser Ala Gly Asp Lys Val Tyr Ile Asp Lys Ile Glu Phe
625                 630                 635                 640

Ile Pro Val Asn

<210> SEQ ID NO 3
<211> LENGTH: 1965
<212> TYPE: DNA
<213> ORGANISM: Artificial Sequence
<220> FEATURE:
<223> OTHER INFORMATION: axmi-R1 with histidine tag

<400> SEQUENCE: 3

| | |
|---|---|
| atggcacatc accaccacca tcacggatcc atgaatccga caatcgaag tgaacatgat | 60 |
| acaataaaaa ctactgaaaa taatgaggtg ccaactaacc atgttcaata tcctttagcg | 120 |
| gaaactccaa atccaacact agaagattta aattataaag agttttttaag aatgactgca | 180 |
| gataataata cggaagcact agatagctct acaacaaaag atgtcattca aaaaggcatt | 240 |
| tccgtagtag gtgatctcct aggcgtagta ggtttcccgt ttggtggagc gcttgtttcg | 300 |
| ttttatacaa acttttttaaa tactatttgg ccaagtgaag acccgtggaa ggcttttatg | 360 |
| gaacaagtag aagcattgat ggatcagaaa atagctgatt atgcaaaaaa taaagctctt | 420 |
| gcagagttac agggccttca aaataatgtc gaagattatg tgagtgcatt gagttcatgg | 480 |
| caaaaaaatc ctgtgagttc acgaaatcca catagccagg ggcggataag agagctgttt | 540 |
| tctcaagcag aaagtcattt tcgtaattca atgccttcgt ttgcaatttc tggatacgag | 600 |
| gttctatttc taacaacata tgcacaagct gccaacacac atttatttttt actaaaagac | 660 |
| gctcaaattt atggagaaga tggggatac gaaaaagaag atattgctga atttttataaa | 720 |
| agacaactaa aacttacgca agaatatact gaccattgtg tcaaatggta taatgttgga | 780 |
| ttagataaat taagaggttc atcttatgaa tcttgggtaa actttaaccg ttatcgcaga | 840 |
| gagatgacat taacagtatt agatttaatt gcactatttc cattgtatga tgttcggcta | 900 |
| tacccaaaag aagttaaaac cgaattaaca agagacgttt taacagatcc aattgtcgga | 960 |
| gtcaacaacc ttaggggcta tggaacaacc ttctctaata tagaaaatta tattcgaaaa | 1020 |
| ccacatctat ttgactatct gcatagaatt caatttcaca cgcggttcca accaggatat | 1080 |
| tatgaaaatg actctttcaa ttattggtcc ggtaattatg tttcaactag accaagcata | 1140 |
| ggatcaaatg atataatcac atctccattc tatggaaata atccagtga acctgtacaa | 1200 |
| aatttagaat ttaatggaga aaaagtctat agagccgtag caaatacaaa tcttgcggtc | 1260 |
| tggccgtccg ctgtatattc aggtgttaca aaagtggaat ttagccaata taatgatcaa | 1320 |
| acagatgaag caagtacaca aacgtacgac tcaaaaagaa atgttggcgc ggtcagctgg | 1380 |
| gattctatcg atcaattgcc tccagaaaca acagatgaac ctctagaaaa gggatatagc | 1440 |
| catcaactca attatgtaat gtgcttttta atgcagggta gtagaggaac aatcccagtg | 1500 |
| ttaacttgga cacataaaag tgtagacttt tttaacatga ttgattcgaa aaaaattaca | 1560 |
| caacttccgt tagtaaaggc atataagtta caatctggtg cttccgttgt cgcaggtcct | 1620 |
| aggtttacag gaggagatat cattcaatgc acagaaaatg gaagtgcggc aactatttac | 1680 |
| gttacaccgg atgtgtcgta ctctcaaaaa tatcgagcta gaattcatta tgcttctaca | 1740 |
| tctcagataa catttacact cagtttagac ggggcaccat ttaatcaata ctatttcgat | 1800 |
| aaaacgataa ataaaggaga cattaacg tataattcat ttaatttagc aagtttcagc | 1860 |
| acaccattcg aattatcagg gaataactta caaataggcg tcacaggatt aagtgctgga | 1920 | gataaagttt atatagacaa aattgaattt attccagtga attag        1965

<210> SEQ ID NO 4
<211> LENGTH: 654
<212> TYPE: PRT
<213> ORGANISM: Artificial Sequence
<220> FEATURE:
<223> OTHER INFORMATION: Axmi-R1 with histidine tag

<400> SEQUENCE: 4

```
Met Ala His His His His His His Gly Ser Met Asn Pro Asn Asn Arg
 1               5                  10                  15

Ser Glu His Asp Thr Ile Lys Thr Thr Glu Asn Asn Glu Val Pro Thr
            20                  25                  30

Asn His Val Gln Tyr Pro Leu Ala Glu Thr Pro Asn Pro Thr Leu Glu
        35                  40                  45

Asp Leu Asn Tyr Lys Glu Phe Leu Arg Met Thr Ala Asp Asn Asn Thr
    50                  55                  60

Glu Ala Leu Asp Ser Ser Thr Thr Lys Asp Val Ile Gln Lys Gly Ile
65                  70                  75                  80

Ser Val Val Gly Asp Leu Leu Gly Val Val Gly Phe Pro Phe Gly Gly
                85                  90                  95

Ala Leu Val Ser Phe Tyr Thr Asn Phe Leu Asn Thr Ile Trp Pro Ser
            100                 105                 110

Glu Asp Pro Trp Lys Ala Phe Met Glu Gln Val Glu Ala Leu Met Asp
        115                 120                 125

Gln Lys Ile Ala Asp Tyr Ala Lys Asn Lys Ala Leu Ala Glu Leu Gln
    130                 135                 140

Gly Leu Gln Asn Asn Val Glu Asp Tyr Val Ser Ala Leu Ser Ser Trp
145                 150                 155                 160

Gln Lys Asn Pro Val Ser Ser Arg Asn Pro His Ser Gln Gly Arg Ile
                165                 170                 175

Arg Glu Leu Phe Ser Gln Ala Glu Ser His Phe Arg Asn Ser Met Pro
            180                 185                 190

Ser Phe Ala Ile Ser Gly Tyr Glu Val Leu Phe Leu Thr Thr Tyr Ala
        195                 200                 205

Gln Ala Ala Asn Thr His Leu Phe Leu Leu Lys Asp Ala Gln Ile Tyr
    210                 215                 220

Gly Glu Glu Trp Gly Tyr Glu Lys Glu Asp Ile Ala Glu Phe Tyr Lys
225                 230                 235                 240

Arg Gln Leu Lys Leu Thr Gln Glu Tyr Thr Asp His Cys Val Lys Trp
                245                 250                 255

Tyr Asn Val Gly Leu Asp Lys Leu Arg Gly Ser Ser Tyr Glu Ser Trp
            260                 265                 270

Val Asn Phe Asn Arg Tyr Arg Arg Glu Met Thr Leu Thr Val Leu Asp
        275                 280                 285

Leu Ile Ala Leu Phe Pro Leu Tyr Asp Val Arg Leu Tyr Pro Lys Glu
    290                 295                 300

Val Lys Thr Glu Leu Thr Arg Asp Val Leu Thr Asp Pro Ile Val Gly
305                 310                 315                 320

Val Asn Asn Leu Arg Gly Tyr Gly Thr Thr Phe Ser Asn Ile Glu Asn
                325                 330                 335

Tyr Ile Arg Lys Pro His Leu Phe Asp Tyr Leu His Arg Ile Gln Phe
            340                 345                 350

His Thr Arg Phe Gln Pro Gly Tyr Tyr Gly Asn Asp Ser Phe Asn Tyr
        355                 360                 365
```

Trp Ser Gly Asn Tyr Val Ser Thr Arg Pro Ser Ile Gly Ser Asn Asp
    370                 375                 380

Ile Ile Thr Ser Pro Phe Tyr Gly Asn Lys Ser Ser Glu Pro Val Gln
385                 390                 395                 400

Asn Leu Glu Phe Asn Gly Glu Lys Val Tyr Arg Ala Val Ala Asn Thr
                405                 410                 415

Asn Leu Ala Val Trp Pro Ser Ala Val Tyr Ser Gly Val Thr Lys Val
            420                 425                 430

Glu Phe Ser Gln Tyr Asn Asp Gln Thr Asp Glu Ala Ser Thr Gln Thr
        435                 440                 445

Tyr Asp Ser Lys Arg Asn Val Gly Ala Val Ser Trp Asp Ser Ile Asp
    450                 455                 460

Gln Leu Pro Pro Glu Thr Thr Asp Glu Pro Leu Glu Lys Gly Tyr Ser
465                 470                 475                 480

His Gln Leu Asn Tyr Val Met Cys Phe Leu Met Gln Gly Ser Arg Gly
                485                 490                 495

Thr Ile Pro Val Leu Thr Trp Thr His Lys Ser Val Asp Phe Phe Asn
            500                 505                 510

Met Ile Asp Ser Lys Lys Ile Thr Gln Leu Pro Leu Val Lys Ala Tyr
        515                 520                 525

Lys Leu Gln Ser Gly Ala Ser Val Val Ala Gly Pro Arg Phe Thr Gly
    530                 535                 540

Gly Asp Ile Ile Gln Cys Thr Glu Asn Gly Ser Ala Ala Thr Ile Tyr
545                 550                 555                 560

Val Thr Pro Asp Val Ser Tyr Ser Gln Lys Tyr Arg Ala Arg Ile His
                565                 570                 575

Tyr Ala Ser Thr Ser Gln Ile Thr Phe Thr Leu Ser Leu Asp Gly Ala
            580                 585                 590

Pro Phe Asn Gln Tyr Tyr Phe Asp Lys Thr Ile Asn Lys Gly Asp Thr
        595                 600                 605

Leu Thr Tyr Asn Ser Phe Asn Leu Ala Ser Phe Ser Thr Pro Phe Glu
    610                 615                 620

Leu Ser Gly Asn Asn Leu Gln Ile Gly Val Thr Gly Leu Ser Ala Gly
625                 630                 635                 640

Asp Lys Val Tyr Ile Asp Lys Ile Glu Phe Ile Pro Val Asn
                645                 650

<210> SEQ ID NO 5
<211> LENGTH: 1935
<212> TYPE: DNA
<213> ORGANISM: Artificial Sequence
<220> FEATURE:
<223> OTHER INFORMATION: synthetic nucleotide sequence encoding
      AXMI-R1(evo18)

<400> SEQUENCE: 5
atgaacccca caacaggag cgagcatgac accatcaaga caacagagaa caatgaagtt      60
ccaacaaacc atgttcaata tcctcttgct gaaacaccaa atccaacctt ggaggacctc    120
aactacaagg agttcttgag gatgacagct gacaacaaca cagaagctct ggattcaagc    180
accaccaagg atgtcatcca gaagggcatc tctgttgttg agatctgct gggcgtggtg     240 ggcttcccct tcggcggcgc gctggtgagc ttctacacca acttcctcaa caccatctgg    300
ccatcagaag atccatggaa ggccttcatg gagcaagtgg aggcgctgat ggaccagaag    360
attgctgatt atgccaagaa caaggcgctg gcggagctgc aaggcctcca gaacaatgtg    420

-continued

```
gaggattatg tttctgctct gagcagctgg cagaagaacc ctgtttcttc aagaaatcct    480
cacagccaag gaaggatcag ggagctcttc tcccaagcag aaagccactt cagaaacagc    540 atgcccctcct tcgccatctc aggatatgag gtgctcttcc tcaccacata tgctcaagct    600
gccaacaccc acctcttcct gctgaaggat gctcaaattt atggagaaga atggggatat    660
gagaaggagg acattgctga gttctacaag aggcagctaa agctcaccca ggagtacaca    720
gatcactgcg tcaaatggta caatgttggg ctggacaagc tccgcggcag cagctatgaa    780
agctgggtga acttcaacag atacaggagg gagatgaccc tcaccgtgct ggacctcatt    840
gctctcttcc ctctctatga tgtccgcctc taccccaagg aggtgaaaac agagctaaca    900
agagatgtgc tgacagatcc catcgtcggc gtcaacaact gaggacata tggcaccacc    960 ttcagcaaca tcgagaacta catcaggaag cctcatctct tcgactacct ccacaggatt   1020
cagttccaca caaggttcca gcctggatat tatggaaatg acagcttcaa ctactggagc   1080
ggcaactatg tttcaacaag gccaagcatt ggaagcaatg acatcataac ttctcccttc   1140
tatggcaaca agagcagcga gcctgttcag aacctggagt tcaatggaga aaggtgtac   1200 cgcgccgtcg ccaacaccaa cctcgccgtc tggccatcag ctgtctacag cggcgtgacc   1260
aaggtggagt tcagccagta caatgatcaa acagatgaag caagcaccca aacatatgac   1320
agcaagagaa atgttggagc tgtttcatgg acagcatcg accagctgcc gccggagaca   1380
acagatgagc cgctggagaa gggctacagc caccagctca actatgtgat gtgcttcttg   1440
atgcaaggaa gcagaggcac catccccgtg ctgacatgga cccacaaatc agtggacttc   1500
ttcaacatga ttgacagcaa gaagatcacc cagctgccgc tggtgaaggc ctacaagctg   1560
caaagcggcg cctccgtggt ggctgggccg cgcttcactg gaggagacat catccaatgc   1620
acagaaaatg gcagcgccgc caccatctat gtcacccctg atgtcagcta cagccagaag   1680
tacagagcaa ggattcatta tgcttcaaca agccagatca ccttcacctt gagcttggat   1740
ggagctccct tcaaccagta ctacttcgac aagaccatca acaaaggaga caccctcacc   1800
tacaacagct tcaacctcgc ctccttctcc acgccatttg agctctcagg aaacaacctc   1860
cagatcggcg tcaccggcct ctccgccggc gacaaggtgt acatcgacaa gatcgagttc   1920
atccccgtca actaa                                                      1935
```

<210> SEQ ID NO 6
<211> LENGTH: 644
<212> TYPE: PRT
<213> ORGANISM: Artificial Sequence
<220> FEATURE:
<223> OTHER INFORMATION: Axmi-R1 variant sequence (AXMI-R1(evo18))

<400> SEQUENCE: 6

```
Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95
```

```
Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
290                 295                 300

Thr Asp Pro Ile Val Gly Val Asn Asn Leu Arg Thr Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525
```

```
Gly Pro Arg Phe Thr Gly Gly Asp Ile Ile Gln Cys Thr Glu Asn Gly
        530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
        610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 7
<211> LENGTH: 1935
<212> TYPE: DNA
<213> ORGANISM: Artificial Sequence
<220> FEATURE:
<223> OTHER INFORMATION: synthetic nucleotide sequence encoding AXMI-R1
      variant sequence (AXMI-R1(evo19))

<400> SEQUENCE: 7
atgaacccca caacaggag cgagcatgac accatcaaga caacagagaa caatgaagtt      60
ccaacaaatc atgtgcagta cccgctggcg gagacaccaa atccaacatt ggaggacctc    120
aactacaagg agttcttgag gatgacggcg gacaacaaca cagaagctct ggacagcagc    180
accaccaagg atgtcatcca agagggcatc tcagtggtgg agatcttct tggagtggtg     240 ggcttccct cggcggcgc gctggttagc ttctacacca acttcctcaa caccatctgg      300
ccatcagaag atccatggaa ggccttcatg agcaagtgg aggcgctgat ggaccagaag     360
atcgccgact acgccaagaa caaggcgctg gcggagctgc aaggcctcca gaacaatgtt    420
gaagattatg tctcggcgct gagcagctgg cagaagaacc cggtgagctc aagaaatatc    480
cattctcaag gaaggatcag ggagctcttc agccaagcag aaagccactt cagaaacagc    540
atgccgagct tcgccatctc aggatatgag gtgctcttcc tcaccaccta tgctcaagct    600
gccaacaccc cctcttcct gctgaaggat gctcaaattt atggagaaga atggggctat    660
gagaaggagg acattgctga gttctacaag aggcagctaa agctgacaca agagtacacc    720
gaccactgcg tcaagtggta caatgttggg ctggacaagc tccgcggcag cagctatgaa    780
agctgggtga acttcaacag atacaggagg gagatgacgc tcaccgtgct ggacctcatt    840
gctctcttcc cgctctatga tgtgaggctc taccccaagg aggtcaagac agagctgaca    900
agagatgtgc taacagatcc catcgtcggc gtcaacaacc tccgcaccta tggcaccacc    960
ttcagcaaca tcgagaacta catcaggaag ccgcacctct tcgactacct ccaccgcatc   1020
cagttccaca caaggttcca acctggatat tatggaaatg acagcttcaa ctactggagc   1080
ggcaactatg tttcaacaag gccaagcata ggaagcaacg acatcatcac ctcgcccttc   1140
tacggcaaca gagctccga gccggtgcaa aatttggagt tcaatggaga aaggtgtac   1200 cgcgccgtcg ccaacaccaa cctcgccgtc tggccatcag ctgtctacag cggcgtgacc   1260
aaggtggagt tcagccagta caatgatcaa acagatgaag caagcaccca gacctacgac   1320
agcaagagga acgtcggcgc cgtgtcatgg gacagcatcg accagctgcc gccggagaca   1380
```

```
acagatgagc cgctggagaa gggctacagc caccagctca actatgtgat gtgcttcttg   1440
atgcaaggaa gccgcggcac catcccggtg ctgacatgga cccacaagag cgtggacttc   1500
ttcaacatga ttgattcaaa gaagatcacc cagctgccgc tggtgaaggc ctacaagctg   1560
caaagcggcg cctccgtggt ggctgggcca aggttcaccg gcggcgacat catccaatgc   1620
acagaaaatg aagcgccgc caccatctat gtgacacctg atgtgagcta cagccagaag   1680
tacagagcaa ggattcatta tgcttcaaca agccagatca ccttcacctt gagcttggat   1740
ggagctccct tcaaccagta ctacttcgac aagaccatca caaaggaga cccttgacc   1800 tacaacagct tcaacctcgc cagcttctca acaccatttg agctgagcgg caacaacctc   1860
cagatcggcg tcaccggcct ctccgccggc gacaaggtct acatcgacaa gattgagttc   1920
atcccggtga actaa                                                    1935

<210> SEQ ID NO 8
<211> LENGTH: 644
<212> TYPE: PRT
<213> ORGANISM: Artificial Sequence
<220> FEATURE:
<223> OTHER INFORMATION: AXMI-R1 variant sequence (AXMI-R1(evo19

```
                260             265             270
Thr Leu Thr Val Leu Asp Leu Ile Ala Leu Phe Pro Leu Tyr Asp Val
        275                 280                 285
Arg Leu Tyr Pro Lys Glu Val Lys Thr Glu Leu Thr Arg Asp Val Leu
        290                 295                 300
Thr Asp Pro Ile Val Gly Val Asn Asn Leu Arg Thr Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
                340                 345                 350
Asn Asp Ser Phe Asn Tyr Trp Ser Gly Asn Tyr Val Ser Thr Arg Pro
                355                 360                 365
Ser Ile Gly Ser Asn Asp Ile Ile Thr Ser Pro Phe Tyr Gly Asn Lys
        370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
                420                 425                 430
Glu Ala Ser Thr Gln Thr Tyr Asp Ser Lys Arg Asn Val Gly Ala Val
                435                 440                 445
Ser Trp Asp Ser Ile Asp Gln Leu Pro Pro Glu Thr Thr Asp Glu Pro
        450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
                500                 505                 510
Pro Leu Val Lys Ala Tyr Lys Leu Gln Ser Gly Ala Ser Val Val Ala
                515                 520                 525
Gly Pro Arg Phe Thr Gly Gly Asp Ile Ile Gln Cys Thr Glu Asn Gly
        530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
                580                 585                 590
Ile Asn Lys Gly Asp Thr Leu Thr Tyr Asn Ser Phe Asn Leu Ala Ser
        595                 600                 605
Phe Ser Thr Pro Phe Glu Leu Ser Gly Asn Asn Leu Gln Ile Gly Val
        610                 615                 620
Thr Gly Leu Ser Ala Gly Asp Lys Val Tyr Ile Asp Lys Ile Glu Phe
625                 630                 635                 640
Ile Pro Val Asn

<210> SEQ ID NO 9
<211> LENGTH: 1935
<212> TYPE: DNA
<213> ORGANISM: Artificial Sequence
<220> FEATURE:
<223> OTHER INFORMATION: synthetic nucleotide sequence encoding AXMI-R1
```

-continued variant sequence (AXMI-R1(evo20))

<400> SEQUENCE: 9

```
atgaacccca acaacaggag cgagcatgac accatcaaga caacagagaa caatgaagtt      60
ccaacaaatc atgtgcagta cccgctggcg gagacaccaa atccaacatt ggaggacctc     120
aactacaagg agttcttgag gatgacggcg gacaacaaca cagaagctct ggacagcagc     180
accaccaagg atgtcatcca gaagggcatc tcagtggtgg agatcttct tggagtggtg      240
ggcttcccct tcggcggcgc gctggttagc ttctacacca acttcctcaa caccatctgg     300
ccatcagaag atccatggaa ggccttcatg gagcaagtgg aggcgctgat ggaccagaag     360
atcgccgact acgccaagaa caaggcgctg gcggagctgc aaggcctcca gaacaatgtt     420
gaagattatg tctcggcgct gagcagctgg cagaagaacg cgaagagctc aagaaatgtg     480
cattctcaag gaaggatcag ggagctcttc agccaagcag aaagccactt cagaaacagc     540
atgccgagct tcgccatctc aggatatgag gtgctcttcc tcaccaccta tgctcaagct     600
gccaacaccc acctcttcct gctgaaggat gctcaaattt atggagaaga tggggctat     660
gagaaggagg acattgctga gttctacaag aggcagctaa agctgacaca agagtacacc     720
gaccactgcg tcaagtggta caatgttggg ctggacaagc tccgcggcag cagctatgaa     780
agctgggtga acttcaacag atacaggagg agatgacgc tcaccgtgct ggacctcatt     840
gctctcttcc cgctctatga tgtgaggctc taccccaagg aggtcaagac agagctgaca     900
agagatgtgc taacagatcc catcgtcggc gtcaacaacc tccgcaccta tggcaccacc     960
ttcagcaaca tcgagaacta catcaggaag ccgcacctct tcgactacct ccaccgcatc    1020
cagttccaca caaggttcca acctggatat tatggaaatg acagcttcaa ctactggagc    1080
ggcaactatg tttcaacaag gccaagcata ggaagcaaca catcatcac ctcgcccttc    1140
tacggcaaca agagctccga gccggtgcaa aatttggagt tcaatggaga aaggtgtac    1200
cgcgccgtcg ccaacaccaa cctcgccgtc tggccatcag ctgtctacag cggcgtgacc    1260
aaggtggagt tcagccagta caatgatcaa acagatgaag caagcaccca gacctacgac    1320
agcaagagga acgtcggcgc cgtgtcatgg gacagcatcg accagctgcc gccggagaca    1380
acagatgagc cgctggagaa gggctacagc caccagctca actatgtgat gtgcttcttg    1440
atgcaaggaa gccgcggcac catcccggtg ctgacatgga cccacaagag cgtggacttc    1500
ttcaacatga ttgattcaaa gaagatcacc cagctgccgc tggtgaaggc ctacaagctg    1560
caaagcggcg cctccgtggt ggctgggcca aggttcaccg gcggcacat catccaatgc    1620
acagaaaatg aagcgccgc caccatctat gtgacacctg atgtgagcta cagccagaag    1680
tacagagcaa ggattcatta tgcttcaaca agccagatca ccttcacctt gagcttggat    1740
ggagctccct tcaaccagta ctacttcgac aagaccatca acaaggaga caccttgacc    1800
tacaacagct tcaacctcgc cagcttctca acaccatttg agctgagcgg caacaacctc    1860
cagatcggcg tcaccggcct ctccgccggc gacaaggtct acatcgacaa gattgagttc    1920
atcccggtga actaa                                                    1935
```

<210> SEQ ID NO 10
<211> LENGTH: 644
<212> TYPE: PRT
<213> ORGANISM: Artificial Sequence
<220> FEATURE:
<223> OTHER INFORMATION: AXMI-R1 variant sequence (AXMI-R1(evo20))

<400> SEQUENCE: 10

-continued

```
Met Asn Pro Asn Asn Arg Ser Glu His Asp Thr Ile Lys Thr Thr Glu
 1               5                  10                  15
Asn Asn Glu Val Pro Thr Asn His Val Gln Tyr Pro Leu Ala Glu Thr
             20                  25                  30
Pro Asn Pro Thr Leu Glu Asp Leu Asn Tyr Lys Glu Phe Leu Arg Met
         35                  40                  45
Thr Ala Asp Asn Asn Thr Glu Ala Leu Asp Ser Ser Thr Thr Lys Asp
 50                  55                  60
Val Ile Gln Lys Gly Ile Ser Val Val Gly Asp Leu Leu Gly Val Val
 65                  70                  75                  80
Gly Phe Pro Phe Gly Gly Ala Leu Val Ser Phe Tyr Thr Asn Phe Leu
                 85                  90                  95
Asn Thr Ile Trp Pro Ser Glu Asp Pro Trp Lys Ala Phe Met Glu Gln
                100                 105                 110
Val Glu Ala Leu Met Asp Gln Lys Ile Ala Asp Tyr Ala Lys Asn Lys
            115                 120                 125
Ala Leu Ala Glu Leu Gln Gly Leu Gln Asn Asn Val Glu Asp Tyr Val
130                 135                 140
Ser Ala Leu Ser Ser Trp Gln Lys Asn Ala Lys Ser Ser Arg Asn Val
145                 150                 155                 160
His Ser Gln Gly Arg Ile Arg Glu Leu Phe Ser Gln Ala Glu Ser His
                165                 170                 175
Phe Arg Asn Ser Met Pro Ser Phe Ala Ile Ser Gly Tyr Glu Val Leu
                180                 185                 190
Phe Leu Thr Thr Tyr Ala Gln Ala Ala Asn Thr His Leu Phe Leu Leu
            195                 200                 205
Lys Asp Ala Gln Ile Tyr Gly Glu Glu Trp Gly Tyr Glu Lys Glu Asp
210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
                245                 250                 255
Ser Ser Tyr Glu Ser Trp Val Asn Phe Asn Arg Tyr Arg Arg Glu Met
                260                 265                 270
Thr Leu Thr Val Leu Asp Leu Ile Ala Leu Phe Pro Leu Tyr Asp Val
            275                 280                 285
Arg Leu Tyr Pro Lys Glu Val Lys Thr Glu Leu Thr Arg Asp Val Leu
290                 295                 300
Thr Asp Pro Ile Val Gly Val Asn Asn Leu Arg Thr Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
                340                 345                 350
Asn Asp Ser Phe Asn Tyr Trp Ser Gly Asn Tyr Val Ser Thr Arg Pro
            355                 360                 365
Ser Ile Gly Ser Asn Asp Ile Ile Thr Ser Pro Phe Tyr Gly Asn Lys
370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
                420                 425                 430
```

```
Glu Ala Ser Thr Gln Thr Tyr Asp Ser Lys Arg Asn Val Gly Ala Val
            435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
            485                 490                 495

Ser Val Asp Phe Phe Asn Met Ile Asp Ser Lys Lys Ile Thr Gln Leu
        500                 505                 510

Pro Leu Val Lys Ala Tyr Lys Leu Gln Ser Gly Ala Ser Val Val Ala
    515                 520                 525

Gly Pro Arg Phe Thr Gly Gly Asp Ile Ile Gln Cys Thr Glu Asn Gly
530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 11
<211> LENGTH: 4
<212> TYPE: PRT
<213> ORGANISM: Artificial Sequence
<220> FEATURE:
<223> OTHER INFORMATION: endoplasmic reticulum signal sequence

<400> SEQUENCE: 11

Lys Asp Glu Leu
 1

<210> SEQ ID NO 12
<211> LENGTH: 1932
<212> TYPE: DNA
<213> ORGANISM: Artificial Sequence
<220> FEATURE:
<223> OTHER INFORMATION: nucleotide sequence encoding variant of Axmi-R1
      (Axmi-R1(3c7))

<400> SEQUENCE: 12
atgaatccga caatcgaag tgaacatgat acaataaaaa ctactgaaaa taatgaggtg      60
ccaactaacc atgttcaata tcctttagcg gaaactccaa atccaacact agaagattta     120
aattataaag agttttttaag aatgactgca gataataata cggaagcact agatagctct     180
acaacaaaag atgtcattca aaaaggcatt tccgtagtag gtgatctcct aggcgtagta     240
ggtttcccgt tggtggagc gcttgtttcg ttttatacaa acttttttaaa tactatttgg     300 ccaagtgaag acccgtggaa ggcttttatg gaacaagtag aagcattgat ggatcagaaa     360
atagctgatt atgcaaaaaa taaagctctt gcagagttac agggccttca aaataatgtc     420
```

```
gaagattatg tgagtgcatt gagttcatgg caaaaaaatg caaagagttc acgaaatgta    480
catagccagg ggcggataag agagctgttt tctcaagcag aaagtcattt tcgtaattca    540
atgccttcgt ttgcaattcc tggatacgag gttctatttc taacaacata tgcacaagct    600
gccaacacac atttatttt actaaaagac gctcaaattt atggagaaga atggggatac    660 gaaaagaag atattgctga attttataaa agacaactaa aacttacgca agaatatact    720
gaccattgtg tcaaatggta taatgttgga ttagataaat taagaggttc atcttatgaa    780
tcttgggtaa actttaaccg ttatcgcaga gagatgacat taacagtatt agatttaatt    840
gcactatttc cattgtatga tgttcggcta tacccaaaag aagttaaaac cgaattaaca    900
agagacgttt taacagatcc aattgtcgga gtcaacaacc ttaggggcta tggaacaacc    960
ttctctaata tagaaaatta tattcgaaaa ccacatctat ttgactatct gcatagaatt   1020
caatttcaca cgcggttcca accaggatat tatggaaatg actctttcaa ttattggtcc   1080
ggtaattatg tttcaactag accaagcata ggatcaaatg atataatcac atctccattc   1140
tatggaaata atccagtga acctgtacaa aatttagaat ttaatggaga aaaagtctat   1200
agagccgtag caaatacaaa tcttgcggtc tggccgtccg ctgtatattc aggtgttaca   1260
aaagtggaat ttagccaata taatgatcaa acagatgaag caagtacaca aacgtacgac   1320
tcaaaaagaa atgttggcgc ggtcagctgg gattctatcg atcaattgcc tccagaaaca   1380
acagatgaac ctctagaaaa gggatatagc catcaactca attatgtaat gtgctttta   1440 atgcagggta gtagaggaac aatcccagtg ttaacttgga cacataaaag tgtagacttt   1500
tttaacatga ttgattcgaa aaaaattaca caacttccgt tagtaaaggc atataagtta   1560
caatctggtg cttccgttgt cgcaggtcct aggtttacag gaggagatat cattcaatgc   1620
acagaaaatg gaagtgcggc aactattac gttacaccgg atgtgtcgta ctctcaaaaa   1680
tatcgagcta gaattcatta tgcttctaca tctcagataa catttacact cagtttagac   1740
ggggcaccat ttaatcaata ctatttcgat aaaacgataa ataaaggaga cacattaacg   1800
tataattcat ttaatttagc aagtttcagc acaccattcg aattatcagg gaataactta   1860
caaataggcg tcacaggatt aagtgctgga gataaagttt atatagacaa aattgaattt   1920
attccagtga at                                                       1932
```

<210> SEQ ID NO 13
<211> LENGTH: 644
<212> TYPE: PRT
<213> ORGANISM: Artificial Sequence
<220> FEATURE:
<223> OTHER INFORMATION: variant of Axmi-R1 (Axmi-R1(3c7))

<400> SEQUENCE: 13

```
Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
             20                  25                  30

Pro Asn Pro Thr Leu Glu Asp Leu Asn Tyr Lys Glu Phe Leu Arg Met
         35                  40                  45

Thr Ala Asp Asn Asn Thr Glu Ala Leu Asp Ser Ser Thr Thr Lys Asp
     50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95
```

```
Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
130                 135                 140

Ser Ala Leu Ser Ser Trp Gln Lys Asn Ala Lys Ser Ser Arg Asn Val
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
            195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
            275                 280                 285

Arg Leu Tyr Pro Lys Glu Val Lys Thr Glu Leu Thr Arg Asp Val Leu
            290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
            435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
            515                 520                 525
```

```
Gly Pro Arg Phe Thr Gly Gly Asp Ile Ile Gln Cys Thr Glu Asn Gly
        530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn
```

<210> SEQ ID NO 14
<211> LENGTH: 1932
<212> TYPE: DNA
<213> ORGANISM: Artificial Sequence
<220> FEATURE:
<223> OTHER INFORMATION: nucleotide sequence encoding variant of Axmi-R1
      (Axmi-R1(1g8))

<400> SEQUENCE: 14

```
atgaatccga acaatcgaag tgaacatgat acaataaaaa ctactgaaaa taatgaggtg      60
ccaactaacc atgttcaata tcctttagcg gaaactccaa atccaacact agaagattta     120
aattataaag agttttaag aatgactgca gataataata cggaagcact agatagctct     180
acaacaaaag atgtcattca aaaaggcatt tccgtagtag gtgatctcct aggcgtagta     240
ggtttcccgt ttggtggagc gcttgtttcg tttatacaa acttttaaa tactatttgg     300
ccaagtgaag acccgtggaa ggcttttatg gaacaagtag aagcattgat ggatcagaaa     360
atagctgatt atgcaaaaaa taagctctt gcagagttac agggccttca aaataatgtc     420
gaagattatg tgagtgcatt gagttcatgg caaaaaaatc ctgtgagttc acgaaatcca     480
catagccagg gcggataag agagctgttt tctcaagcag aaagtcattt tcgtaattca     540
atgccttcgt ttgcaattc tggatacgag gttctatttc taacaacata tgcacaagct     600
gccaacacac atttattttt actaaaagac gctcaaattt atggagaaga atgggggatac     660
gaaaagaag atattgctga attttataaa agacaactaa aacttacgca agaatatact     720
gaccattgtg tcaaatggta taatgttgga ttagataaat taagaggttc atcttatgaa     780
tcttgggtaa actttaaccg ttatcgcaga gagatgacat taacagtatt agatttaatt     840
gcactatttc cattgtatga tgttcggcta tacccaaaag aagttaaaac cgaattaaca     900
agagacgttt taacagatcc aattgtcgga gtcaacaacc ttagggaata tggaacaacc     960
ttctctaata tagaaaatta tattcgaaaa ccacatctat ttgactatct gcatagaatt    1020
caatttcaca cgcggttcca accaggatat tatggaaatg actcttttcaa ttattggtcc    1080
ggtaattatg tttcaactag accaagcata ggatcaaatg atataatcac atctccattc    1140
tatggaaata atccagtga acctgtacaa atttagaat ttaatggaga aaagtctat    1200
agagccgtag caaatacaaa tcttgcggtc tggccgtccg ctgtatattc aggtgttaca    1260
aaagtggaat ttgccaata taatgatcaa acagatgaag caagtacaca aacgtacgac    1320
tcaaaagaa atgttggcgc ggtcagctgg gattctatcg atcaattgcc tccagaaaca    1380
```

```
acagatgaac ctctagaaaa gggatatagc catcaactca attatgtaat gtgcttttta    1440
atgctgaaaa gtagaggaac aatcccagtg ttaacttgga cacataaaag tgtagacttt    1500
tttaacatga ttgattcgaa aaaaattaca caacttccgt tagtaaaggc atataagtta    1560
caatctggtg cttccgttgt cgcaggtcct aggtttacag gaggagatat cattcaatgc    1620
acagaaaatg gaagtgcggc aactatttac gttacaccgg atgtgtcgta ctctcaaaaa    1680
tatcgagcta gaattcatta tgcttctaca tctcagataa catttacact cagtttagac    1740
ggggcaccat ttaatcaata ctatttcgat aaaacgataa ataaaggaga cacattaacg    1800
tataattcat ttaatttagc aagtttcagc acaccattcg aattatcagg gaataactta    1860
caaataggcg tcacaggatt aagtgctgga gataaagttt atatagacaa aattgaattt    1920
attccagtga at                                                        1932
```

<210> SEQ ID NO 15
<211> LENGTH: 644
<212> TYPE: PRT
<213> ORGANISM: Artificial Sequence
<220> FEATURE:
<223> OTHER INFORMATION: variant of Axmi-R1 (Axmi-R1(1g8))

<400> SEQUENCE: 15

```
Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
```

```
                  260             265             270
Thr Leu Thr Val Leu Asp Leu Ile Ala Leu Phe Pro Leu Tyr Asp Val
            275                 280                 285
Arg Leu Tyr Pro Lys Glu Val Lys Thr Glu Leu Thr Arg Asp Val Leu
        290                 295                 300
Thr Asp Pro Ile Val Gly Val Asn Asn Leu Arg Glu Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
        355                 360                 365
Ser Ile Gly Ser Asn Asp Ile Ile Thr Ser Pro Phe Tyr Gly Asn Lys
    370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
        435                 440                 445
Ser Trp Asp Ser Ile Asp Gln Leu Pro Pro Glu Thr Thr Asp Glu Pro
    450                 455                 460
Leu Glu Lys Gly Tyr Ser His Gln Leu Asn Tyr Val Met Cys Phe Leu
465                 470                 475                 480
Met Leu Lys Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
            500                 505                 510
Pro Leu Val Lys Ala Tyr Lys Leu Gln Ser Gly Ala Ser Val Val Ala
        515                 520                 525
Gly Pro Arg Phe Thr Gly Gly Asp Ile Ile Gln Cys Thr Glu Asn Gly
    530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
            580                 585                 590
Ile Asn Lys Gly Asp Thr Leu Thr Tyr Asn Ser Phe Asn Leu Ala Ser
        595                 600                 605
Phe Ser Thr Pro Phe Glu Leu Ser Gly Asn Asn Leu Gln Ile Gly Val
    610                 615                 620
Thr Gly Leu Ser Ala Gly Asp Lys Val Tyr Ile Asp Lys Ile Glu Phe
625                 630                 635                 640
Ile Pro Val Asn

<210> SEQ ID NO 16
<211> LENGTH: 1932
<212> TYPE: DNA
<213> ORGANISM: Artificial Sequence
<220> FEATURE:
<223> OTHER INFORMATION: nucleotide sequence encoding variant of Axmi-R1
```

(Axmi-R1(Evo23))

<400> SEQUENCE: 16

```
atgaatccga acaatcgaag tgaacatgat acaataaaaa ctactgaaaa taatgaggtg      60
ccaactaacc atgttcaata tcctttagcg gaaactccaa atccaacact agaagattta     120
aattataaag agttttaag aatgactgca gataataata cggaagcact agatagctct     180
acaacaaaag atgtcattca aaaaggcatt tccgtagtag gtgatctcct aggcgtagta     240
ggtttcccgt ttggtggagc gcttgtttcg ttttatacaa acttttaaa tactatttgg      300
ccaagtgaag acccgtggaa ggcttttatg gaacaagtag aagcattgat ggatcagaaa     360
atagctgatt atgcaaaaaa taaagctctt gcagagttac agggccttca aaataatgtc     420
gaagattatg tgagtgcatt gagttcatgg caaaaaaatc atgtgagttc acgaaatctt     480
catagccagg ggcggataag agagctgttt tctcaagcag aaagtcattt tcgtaattca     540
atgccttcgt ttgcaatttc tggatacgag gttctatttc taacaacata tgcacaagct     600
gccaacacac atttatttt actaaaagac gctcaaattt atggagaaga atggggatac     660
gaaaaagaag atattgctga attttataaa agacaactaa aacttacgca agaatatact     720
gaccattgtg tcaaatggta taatgttgga ttagataaat taagaggttc atcttatgaa     780
tcttgggtaa actttaaccg ttatcgcaga gagatgacat taacagtatt agatttaatt     840
gcactatttc cattgtatga tgttcggcta tacccaaaag aagttaaaac cgaattaaca     900
agagacgttt taacagatcc aattgtcgga gtcaacaacc ttagggaata tggaacaacc     960
ttctctaata tagaaaatta tattcgaaaa ccacatctat ttgactatct gcatagaatt    1020
caatttcaca cgcggttcca accaggatat tatggaaatg actctttcaa ttattggtcc    1080
ggtaattatg tttcaactag accaagcata ggatcaaatg atataatcac atctccattc    1140
tatggaaata atccagtga acctgtacaa aattttagaat ttaatggaga aaaagtctat    1200
agagccgtag caaatacaaa tcttgcggtc tggccgtccg ctgtatattc aggtgttaca    1260
aaagtggaat ttagccaata taatgatcaa acagatgaag caagtacaca aacgtacgac    1320
tcaaaaagaa atgttggcgc ggtcagctgg gattctatcg atcaattgcc tccagaaaca    1380
acagatgaac tctagaaaaa gggatatagc catcaactca attatgtaat gtgctttta     1440
atgctgaaaa gtagaggaac aatcccagtg ttaacttgga cacataaaag tgtagacttt    1500
tttaacatga ttgattcgaa aaaaattaca caacttccgt tagtaaaggc atataagtta    1560
caatctggtg cttccgttgt cgcaggtcct aggtttacag gaggagatat cattcaatgc    1620
acagaaaatg gaagtgcggc aactatttac gttacaccgg atgtgtcgta ctctcaaaaa    1680
tatcgagcta gaattcatta tgcttctaca tctcagataa catttacact cagttttagac    1740
ggggcaccat ttaatcaata ctatttcgat aaaacgataa ataaaggaga cacattaacg    1800
tataattcat ttaatttagc aagtttcagc acaccattcg aattatcagg gaataactta    1860
caaataggcg tcacaggatt aagtgctgga gataaagttt atatagacaa aattgaattt    1920
attccagtga at                                                         1932
```

<210> SEQ ID NO 17
<211> LENGTH: 644
<212> TYPE: PRT
<213> ORGANISM: Artificial Sequence
<220> FEATURE:
<223> OTHER INFORMATION: variant of Axmi-R1 (Axmi-R1(Evo23))

<400> SEQUENCE: 17

```
Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
                 20                  25                  30

Pro Asn Pro Thr Leu Glu Asp Leu Asn Tyr Lys Glu Phe Leu Arg Met
             35                  40                  45

Thr Ala Asp Asn Asn Thr Glu Ala Leu Asp Ser Ser Thr Thr Lys Asp
         50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
             100                 105                 110

Val Glu Ala Leu Met Asp Gln Lys Ile Ala Asp Tyr Ala Lys Asn Lys
         115                 120                 125

Ala Leu Ala Glu Leu Gln Gly Leu Gln Asn Asn Val Glu Asp Tyr Val
 130                 135                 140

Ser Ala Leu Ser Ser Trp Gln Lys Asn His Val Ser Ser Arg Asn Leu
 145                 150                 155                 160

His Ser Gln Gly Arg Ile Arg Glu Leu Phe Ser Gln Ala Glu Ser His
             165                 170                 175

Phe Arg Asn Ser Met Pro Ser Phe Ala Ile Ser Gly Tyr Glu Val Leu
             180                 185                 190

Phe Leu Thr Thr Tyr Ala Gln Ala Ala Asn Thr His Leu Phe Leu Leu
         195                 200                 205

Lys Asp Ala Gln Ile Tyr Gly Glu Glu Trp Gly Tyr Glu Lys Glu Asp
 210                 215                 220

Ile Ala Glu Phe Tyr Lys Arg Gln Leu Lys Leu Thr Gln Glu Tyr Thr
 225                 230                 235                 240

Asp His Cys Val Lys Trp Tyr Asn Val Gly Leu Asp Lys Leu Arg Gly
             245                 250                 255

Ser Ser Tyr Glu Ser Trp Val Asn Phe Asn Arg Tyr Arg Arg Glu Met
             260                 265                 270

Thr Leu Thr Val Leu Asp Leu Ile Ala Leu Phe Pro Leu Tyr Asp Val
         275                 280                 285

Arg Leu Tyr Pro Lys Glu Val Lys Thr Glu Leu Thr Arg Asp Val Leu
 290                 295                 300

Thr Asp Pro Ile Val Gly Val Asn Asn Leu Arg Glu Tyr Gly Thr Thr
 305                 310                 315                 320

Phe Ser Asn Ile Glu Asn Tyr Ile Arg Lys Pro His Leu Phe Asp Tyr
             325                 330                 335

Leu His Arg Ile Gln Phe His Thr Arg Phe Gln Pro Gly Tyr Tyr Gly
             340                 345                 350

Asn Asp Ser Phe Asn Tyr Trp Ser Gly Asn Tyr Val Ser Thr Arg Pro
         355                 360                 365

Ser Ile Gly Ser Asn Asp Ile Ile Thr Ser Pro Phe Tyr Gly Asn Lys
 370                 375                 380

Ser Ser Glu Pro Val Gln Asn Leu Glu Phe Asn Gly Glu Lys Val Tyr
 385                 390                 395                 400

Arg Ala Val Ala Asn Thr Asn Leu Ala Val Trp Pro Ser Ala Val Tyr
             405                 410                 415

Ser Gly Val Thr Lys Val Glu Phe Ser Gln Tyr Asn Asp Gln Thr Asp
         420                 425                 430
```

```
Glu Ala Ser Thr Gln Thr Tyr Asp Ser Lys Arg Asn Val Gly Ala Val
        435                 440                 445
Ser Trp Asp Ser Ile Asp Gln Leu Pro Pro Glu Thr Thr Asp Glu Pro
450                 455                 460
Leu Glu Lys Gly Tyr Ser His Gln Leu Asn Tyr Val Met Cys Phe Leu
465                 470                 475                 480
Met Leu Lys Ser Arg Gly Thr Ile Pro Val Leu Thr Trp Thr His Lys
        485                 490                 495
Ser Val Asp Phe Phe Asn Met Ile Asp Ser Lys Lys Ile Thr Gln Leu
                500                 505                 510
Pro Leu Val Lys Ala Tyr Lys Leu Gln Ser Gly Ala Ser Val Val Ala
            515                 520                 525
Gly Pro Arg Phe Thr Gly Gly Asp Ile Ile Gln Cys Thr Glu Asn Gly
        530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
            580                 585                 590
Ile Asn Lys Gly Asp Thr Leu Thr Tyr Asn Ser Phe Asn Leu Ala Ser
        595                 600                 605
Phe Ser Thr Pro Phe Glu Leu Ser Gly Asn Asn Leu Gln Ile Gly Val
                610                 615                 620
Thr Gly Leu Ser Ala Gly Asp Lys Val Tyr Ile Asp Lys Ile Glu Phe
625                 630                 635                 640
Ile Pro Val Asn

<210> SEQ ID NO 18
<211> LENGTH: 1932
<212> TYPE: DNA
<213> ORGANISM: Artificial Sequence
<220> FEATURE:
<223> OTHER INFORMATION: nucleotide sequence encoding variant of Axmi-R1
      (Axmi-R1(L61E11)) (Axmi-R1(L61E11))
      (Axmi-R1(Evo23))

<400> SEQUENCE: 18
atgaatccga acaatcgaag tgaacatgat acaataaaaa ctactgaaaa taatgaggtg      60
ccaactaacc atgttcaata tcctttagcg gaaactccaa atccaacact agaagattta     120
aattataaag agttttttaag aatgactgca gataataata cggaagcact agatagctct     180
acaacaaaag atgtcattca aaaaggcatt tccgtagtag gtgatctcct aggcgtagta     240
ggtttcccgt tggtggagc gcttgtttcg ttttatacaa acttttttaaa tactatttgg     300 ccaagtgaag acccgtggaa ggcttttatg gaacaagtag aagcattgat ggatcagaaa     360
atagctgatt atgcaaaaaa taaagctctt gcagagttac agggccttca aaataatgtc     420
gaagattatg tgagtgcatt gagttcatgg caaaaaaatc ctgtgagttc acgaaatcca     480
catagccagg ggcggataag agagctgttt tctcaagcag aaagtcattt tcgtaattca     540
atgccttcgt ttgcaatttc tggatacgag gttctatttc taacaacata tgcacaagct     600
gccaacacac atttatttt actaaaagac gctcaaattt atggagaaga atggggatac     660 gaaaagaag atattgctga attttataaa gacaactaa aacttacgca agaatatact     720
gaccattgtg tcaaatggta taatgttgga ttagataaat taagaggttc atcttatgaa     780
```

```
tcttgggtaa actttaaccg ttatcgcaga gagatgacat taacagtatt agatttaatt    840
gcactatttc cattgtatga tgttcggcta tacccaaaag aagttaaaac cgaattaaca    900
agagacgttt taacagatcc aattgtcgga gtcaacaacc ttaggggcta tggaacaacc    960
ttctctaata tagaaaatta tattcgaaaa ccacatctat ttgactatct gcatagaatt   1020
caatttcaca cgcggttcca accaggatat tatggaaatg actctttcaa ttattggtcc   1080
ggtaattatg tttcaactag accaagcata ggatcaaatg atataatcac atctccattc   1140
tatggaaata atccagtga acctgtacaa aatttagaat ttaatggaga aaaagtctat   1200
agagccgtag caaatacaaa tcttgcggtc tggccgtccg ctgtatattc aggtgttaca   1260
aaagtggaat ttagccaata taatgatcaa acagatgaag caagtacaca aacgtacgac   1320
tcaaaaagaa atgttggcgc ggtcagctgg gattctatcg atcaattgcc tccagaaaca   1380
acagatgaac ctctagaaaa gggatatagc catcaactca attatgtaat gtgctttttta   1440
atgcagggta gtagaggaac aatcccagtg ttaacttgga cacataaaag tgtagacttt   1500
tttaacatga ttgattcgaa aaaaattaca caacttccgt tagtaaaggc atataattta   1560
caatctggtg cttccgttgt cgcaggtcct aggtttacag gaggagatat cattcaatgc   1620
acagaaaatg gaagtgcggc aactatttac gttacaccgg atgtgtcgta ctctcaaaaa   1680
tatcgagcta gaattcatta tgcttctaca tctcagataa catttacact cagtttagac   1740
ggggcaccat ttaatcaata ctatttcgat aaaacgataa ataaaggaga cacattaacg   1800
tataattcat ttaatttagc aagtttcagc acaccattcg aattatcagg aataacttaa   1860
caaataggcg tcacaggatt aagtgctgga gataaagttt atatagacaa aattgaattt   1920
attccagtga at                                                       1932

<210> SEQ ID NO 19
<211> LENGTH: 644
<212> TYPE: PRT
<213> ORGANISM: Artificial Sequence
<220> FEATURE:
<223> OTHER INFORMATION: variant of Axmi-R1 (Axmi-R1(L61E11))

<400> SEQUENCE: 19

Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
             20                  25                  30

Pro Asn Pro Thr Leu Glu Asp Leu Asn Tyr Lys Glu Phe Leu Arg Met
         35                  40                  45

Thr Ala Asp Asn Asn Thr Glu Ala Leu Asp Ser Ser Thr Thr Lys Asp
     50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160
```

```
His Ser Gln Gly Arg Ile Arg Glu Leu Phe Ser Gln Ala Glu Ser His
                165                 170                 175
Phe Arg Asn Ser Met Pro Ser Phe Ala Ile Ser Gly Tyr Glu Val Leu
            180                 185                 190
Phe Leu Thr Thr Tyr Ala Gln Ala Ala Asn Thr His Leu Phe Leu Leu
        195                 200                 205
Lys Asp Ala Gln Ile Tyr Gly Glu Glu Trp Gly Tyr Glu Lys Glu Asp
    210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
                245                 250                 255
Ser Ser Tyr Glu Ser Trp Val Asn Phe Asn Arg Tyr Arg Arg Glu Met
            260                 265                 270
Thr Leu Thr Val Leu Asp Leu Ile Ala Leu Phe Pro Leu Tyr Asp Val
        275                 280                 285
Arg Leu Tyr Pro Lys Glu Val Lys Thr Glu Leu Thr Arg Asp Val Leu
    290                 295                 300
Thr Asp Pro Ile Val Gly Val Asn Asn Leu Arg Gly Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
        355                 360                 365
Ser Ile Gly Ser Asn Asp Ile Ile Thr Ser Pro Phe Tyr Gly Asn Lys
    370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
        435                 440                 445
Ser Trp Asp Ser Ile Asp Gln Leu Pro Pro Glu Thr Thr Asp Glu Pro
    450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
            500                 505                 510
Pro Leu Val Lys Ala Tyr Asn Leu Gln Ser Gly Ala Ser Val Val Ala
        515                 520                 525
Gly Pro Arg Phe Thr Gly Gly Asp Ile Ile Gln Cys Thr Glu Asn Gly
    530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
            580                 585                 590
```

-continued

```
Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
            610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 20
<211> LENGTH: 4
<212> TYPE: PRT
<213> ORGANISM: Artificial Sequence
<220> FEATURE:
<223> OTHER INFORMATION: synthetic tetrapeptide

<400> SEQUENCE: 20

Ala Ala Pro Phe
 1

<210> SEQ ID NO 21
<211> LENGTH: 644
<212> TYPE: PRT
<213> ORGANISM: Artificial Sequence
<220> FEATURE:
<223> OTHER INFORMATION: variant Axmi-R1 (D4F11)

<400> SEQUENCE: 21

Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Ala Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240
```

```
Asp His Cys Val Lys Trp Tyr Asn Val Gly Leu Asp Lys Leu Arg Gly
            245                 250                 255
Ser Ser Tyr Glu Ser Trp Val Asn Phe Asn Arg Tyr Arg Arg Glu Met
        260                 265                 270
Thr Leu Thr Val Leu Asp Leu Ile Ala Leu Phe Pro Leu Tyr Asp Val
    275                 280                 285
Arg Leu Tyr Pro Lys Glu Val Lys Thr Glu Leu Thr Arg Asp Val Leu
290                 295                 300
Thr Asp Pro Ile Val Gly Val Asn Asn Leu Arg Gly Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
        355                 360                 365
Ser Ile Gly Ser Asn Asp Ile Ile Thr Ser Pro Phe Tyr Gly Asn Lys
    370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
        435                 440                 445
Ser Trp Asp Ser Ile Asp Gln Leu Pro Pro Glu Thr Thr Asp Glu Pro
    450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
            500                 505                 510
Pro Leu Val Lys Ala Tyr Lys Leu Gln Ser Gly Ala Ser Val Val Ala
        515                 520                 525
Gly Pro Arg Phe Thr Gly Gly Asp Ile Ile Gln Cys Thr Glu Asn Gly
    530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
            580                 585                 590
Ile Asn Lys Gly Asp Thr Leu Thr Tyr Asn Ser Phe Asn Leu Ala Ser
        595                 600                 605
Phe Ser Thr Pro Phe Glu Leu Ser Gly Asn Asn Leu Gln Ile Gly Val
    610                 615                 620
Thr Gly Leu Ser Ala Gly Asp Lys Val Tyr Ile Asp Lys Ile Glu Phe
625                 630                 635                 640

Ile Pro Val Asn

<210> SEQ ID NO 22
<211> LENGTH: 644
```

```
<212> TYPE: PRT
<213> ORGANISM: Artificial Sequence
<220> FEATURE:
<223> OTHER INFORMATION: variant Axmi-R1 (H9)

<400> SEQUENCE: 22
```

Met Asn Pro Asn Asn Arg Ser Glu His Asp Thr Ile Lys Thr Thr Glu
1               5

```
                385                 390                 395                 400
Arg Ala Val Ala Asn Thr Asn Leu Ala Val Trp Pro Ser Ala Val Tyr
                    405                 410                 415

Ser Gly Val Thr Lys Val Glu Phe Ser Gln Tyr Asn Asp Gln Thr Asp
                    420                 425                 430

Glu Ala Ser Thr Gln Thr Tyr Asp Ser Lys Arg Asn Val Gly Ala Val
                    435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                    485                 490                 495

Ser Val Asp Phe Phe Asn Met Ile Asp Ser Lys Lys Ile Thr Gln Leu
                    500                 505                 510

Pro Leu Val Lys Ala Tyr Lys Leu Gln Ser Gly Ala Ser Val Val Ala
                    515                 520                 525

Gly Pro Arg Phe Thr Gly Gly Asp Ile Ile Gln Cys Thr Glu Asn Gly
    530                 535                 540

Ser Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                    565                 570                 575

Leu Ser Leu Asp Gly Ala Pro Phe Asn Gln Tyr Tyr Phe Asp Lys Thr
                    580                 585                 590

Ile Asn Lys Gly Asp Thr Leu Thr Tyr Asn Ser Phe Asn Leu Ala Ser
                    595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 23
<211> LENGTH: 644
<212> TYPE: PRT
<213> ORGANISM: Artificial Sequence
<220> FEATURE:
<223> OTHER INFORMATION: variant Axmi-R1 (G5)

<400> SEQUENCE: 23

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
                 20                  25                  30

Pro Asn Pro Thr Leu Glu Asp Leu Asn Tyr Lys Glu Phe Leu Arg Met
             35                  40                  45

Thr Ala Asp Asn Asn Thr Glu Ala Leu Asp Ser Ser Thr Thr Lys Asp
 50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
            100                 105                 110
```

```
Val Glu Ala Leu Met Asp Gln Lys Ile Ala Asp Tyr Ala Lys Asn Lys
        115                 120                 125
Ala Leu Ala Glu Leu Gln Gly Leu Gln Asn Asn Val Glu Asp Tyr Val
130                 135                 140
Ser Ala Leu Ser Ser Trp Gln Lys Asn Pro Val Ser Ser Arg Asn Ala
145                 150                 155                 160
His Ser Gln Gly Arg Ile Arg Glu Leu Phe Ser Gln Ala Glu Ser His
                165                 170                 175
Phe Arg Asn Ser Met Pro Ser Phe Ala Ile Ser Gly Tyr Glu Val Leu
            180                 185                 190
Phe Leu Thr Thr Tyr Ala Gln Ala Ala Asn Thr His Leu Phe Leu Leu
        195                 200                 205
Lys Asp Ala Gln Ile Tyr Gly Glu Glu Trp Gly Tyr Glu Lys Glu Asp
210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
                245                 250                 255
Ser Ser Tyr Glu Ser Trp Val Asn Phe Asn Arg Tyr Arg Arg Glu Met
            260                 265                 270
Thr Leu Thr Val Leu Asp Leu Ile Ala Leu Phe Pro Leu Tyr Asp Val
        275                 280                 285
Arg Leu Tyr Pro Lys Glu Val Lys Thr Glu Leu Thr Arg Asp Val Leu
290                 295                 300
Thr Asp Pro Ile Val Gly Val Asn Asn Leu Arg Gly Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
        355                 360                 365
Ser Ile Gly Ser Asn Asp Ile Ile Thr Ser Pro Phe Tyr Gly Asn Lys
370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
        435                 440                 445
Ser Trp Asp Ser Ile Asp Gln Leu Pro Pro Glu Thr Thr Asp Glu Pro
450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
            500                 505                 510
Pro Leu Val Lys Ala Tyr Lys Leu Gln Ser Gly Ala Ser Val Val Ala
        515                 520                 525
Gly Pro Arg Phe Thr Gly Gly Asp Ile Ile Gln Cys Thr Glu Asn Gly
530                 535                 540
```

```
Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 24
<211> LENGTH: 644
<212> TYPE: PRT
<213> ORGANISM: Artificial Sequence
<220> FEATURE:
<223> OTHER INFORMATION: variant Axmi-R1 (H4)

<400> SEQUENCE: 24

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Phe
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
```

```
                260               265                 270
Thr Leu Thr Val Leu Asp Leu Ile Ala Leu Phe Pro Leu Tyr Asp Val
            275                 280                 285
Arg Leu Tyr Pro Lys Glu Val Lys Thr Glu Leu Thr Arg Asp Val Leu
            290                 295                 300
Thr Asp Pro Ile Val Gly Val Asn Asn Leu Arg Gly Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
                340                 345                 350
Asn Asp Ser Phe Asn Tyr Trp Ser Gly Asn Tyr Val Ser Thr Arg Pro
            355                 360                 365
Ser Ile Gly Ser Asn Asp Ile Ile Thr Ser Pro Phe Tyr Gly Asn Lys
            370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
            435                 440                 445
Ser Trp Asp Ser Ile Asp Gln Leu Pro Pro Glu Thr Thr Asp Glu Pro
450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
                485                 490                 495
Ser Val Asp Phe Phe Asn Met Ile Asp Ser Lys Lys Ile Thr Gln Leu
                500                 505                 510
Pro Leu Val Lys Ala Tyr Lys Leu Gln Ser Gly Ala Ser Val Val Ala
            515                 520                 525
Gly Pro Arg Phe Thr Gly Gly Asp Ile Ile Gln Cys Thr Glu Asn Gly
            530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                565                 570                 575
Leu Ser Leu Asp Gly Ala Pro Phe Asn Gln Tyr Tyr Phe Asp Lys Thr
            580                 585                 590
Ile Asn Lys Gly Asp Thr Leu Thr Tyr Asn Ser Phe Asn Leu Ala Ser
            595                 600                 605
Phe Ser Thr Pro Phe Glu Leu Ser Gly Asn Asn Leu Gln Ile Gly Val
            610                 615                 620
Thr Gly Leu Ser Ala Gly Asp Lys Val Tyr Ile Asp Lys Ile Glu Phe
625                 630                 635                 640
Ile Pro Val Asn

<210> SEQ ID NO 25
<211> LENGTH: 644
<212> TYPE: PRT
<213> ORGANISM: Artificial Sequence
<220> FEATURE:
<223> OTHER INFORMATION: variant Axmi-R1 (D4A2)
```

<400> SEQUENCE: 25

```
Met Asn Pro Asn Asn Arg Ser Glu His Asp Thr Ile Lys Thr Thr Glu
 1               5                  10                  15
Asn Asn Glu Val Pro Thr Asn His Val Gln Tyr Pro Leu Ala Glu Thr
             20                  25                  30
Pro Asn Pro Thr Leu Glu Asp Leu Asn Tyr Lys Glu Phe Leu Arg Met
         35                  40                  45
Thr Ala Asp Asn Asn Thr Glu Ala Leu Asp Ser Ser Thr Thr Lys Asp
     50                  55                  60
Val Ile Gln Lys Gly Ile Ser Val Val Gly Asp Leu Leu Gly Val Val
 65                  70                  75                  80
Gly Phe Pro Phe Gly Gly Ala Leu Val Ser Phe Tyr Thr Asn Phe Leu
                 85                  90                  95
Asn Thr Ile Trp Pro Ser Glu Asp Pro Trp Lys Ala Phe Met Glu Gln
            100                 105                 110
Val Glu Ala Leu Met Asp Gln Lys Ile Ala Asp Tyr Ala Lys Asn Lys
        115                 120                 125
Ala Leu Ala Glu Leu Gln Gly Leu Gln Asn Asn Val Glu Asp Tyr Val
    130                 135                 140
Ser Ala Leu Ser Ser Trp Gln Lys Asn Pro Val Ser Ser Arg Asn Pro
145                 150                 155                 160
His Ser Gln Gly Arg Ile Arg Glu Leu Phe Ser Gln Ala Glu Ser His
                165                 170                 175
Phe Arg Asn Ser Met Pro Ser Phe Ala Ile Ser Gly Tyr Glu Val Leu
            180                 185                 190
Phe Leu Thr Thr Tyr Ala Gln Ala Ala Asn Thr His Leu Phe Leu Leu
        195                 200                 205
Lys Asp Ala Gln Ile Tyr Gly Glu Glu Trp Gly Tyr Glu Lys Glu Asp
    210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
                245                 250                 255
Ser Ser Tyr Glu Ser Trp Val Asn Phe Asn Arg Tyr Arg Arg Glu Met
            260                 265                 270
Thr Leu Thr Val Leu Asp Leu Ile Ala Leu Phe Pro Leu Tyr Asp Val
        275                 280                 285
Arg Leu Tyr Pro Lys Glu Val Lys Thr Glu Leu Thr Arg Asp Val Leu
    290                 295                 300
Thr Asp Pro Ile Val Gly Val Asn Asn Leu Arg Gln Tyr Gly Thr Thr
305                 310                 315                 320
Phe Ser Asn Ile Glu Asn Tyr Ile Arg Lys Pro His Leu Phe Asp Tyr
                325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
        355                 360                 365
Ser Ile Gly Ser Asn Asp Ile Ile Thr Ser Pro Phe Tyr Gly Asn Lys
    370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                405                 410                 415
```

```
Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
            435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
            485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
            515                 520                 525

Gly Pro Arg Phe Thr Gly Gly Asp Ile Ile Gln Cys Thr Glu Asn Gly
530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
            565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 26
<211> LENGTH: 644
<212> TYPE: PRT
<213> ORGANISM: Artificial Sequence
<220> FEATURE:
<223> OTHER INFORMATION: variant Axmi-R1 (H4+D5D8)

<400> SEQUENCE: 26

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
            35                  40                  45

Thr Ala Asp Asn Asn Thr Glu Ala Leu Asp Ser Ser Thr Thr Lys Asp
50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
            85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
```

-continued

```
            130                 135                 140
Ser Ala Leu Ser Ser Trp Gln Lys Asn Pro Val Ser Ser Arg Asn Phe
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
                195                 200                 205

Lys Asp Ala Gln Ile Tyr Gly Glu Glu Trp Gly Tyr Glu Lys Glu Asp
            210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                    245                 250                 255

Ser Ser Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
                275                 280                 285

Arg Leu Tyr Pro Lys Glu Val Lys Thr Glu Leu Thr Arg Asp Val Leu
            290                 295                 300

Thr Asp Pro Ile Val Gly Val Asn Asn Leu Arg Thr Tyr Gly Thr Thr
305                 310                 315                 320

Phe Ser Asn Ile Glu Asn Tyr Ile Arg Lys Pro His Leu Phe Asp Tyr
                    325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
                370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                    405                 410                 415

Ser Gly Val Thr Lys Val Glu Phe Ser Gln Tyr Asn Asp Gln Thr Asp
                420                 425                 430

Glu Ala Ser Thr Gln Thr Tyr Asp Ser Lys Arg Asn Val Gly Ala Val
            435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                    485                 490                 495

Ser Val Asp Phe Phe Asn Met Ile Asp Ser Lys Lys Ile Thr Gln Leu
                500                 505                 510

Pro Leu Val Lys Ala Tyr Lys Leu Gln Ser Gly Ala Ser Val Val Ala
            515                 520                 525

Gly Pro Arg Phe Thr Gly Gly Asp Ile Ile Gln Cys Thr Glu Asn Gly
            530                 535                 540

Ser Ala Ala Thr Ile Tyr Val Thr Pro Asp Val Ser Tyr Ser Gln Lys
545                 550                 555                 560
```

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 27
<211> LENGTH: 644
<212> TYPE: PRT
<213> ORGANISM: Artificial Sequence
<220> FEATURE:
<223> OTHER INFORMATION: variant Axmi-R1 (H9+D4A2)

<400> SEQUENCE: 27

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Ile
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

```
Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gln Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
                420                 425                 430

Glu Ala Ser Thr Gln Thr Tyr Asp Ser Lys Arg Asn Val Gly Ala Val
            435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
                500                 505                 510

Pro Leu Val Lys Ala Tyr Lys Leu Gln Ser Gly Ala Ser Val Val Ala
            515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
    595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 28
<211> LENGTH: 644
<212> TYPE: PRT
<213> ORGANISM: Artificial Sequence
<220> FEATURE:
<223> OTHER INFORMATION: variant Axmi-R1 (G5+D4A2)

<400> SEQUENCE: 28

Met Asn Pro Asn Asn Arg Ser Glu His Asp Thr Ile Lys Thr Thr Glu
```

-continued

```
                1               5                  10                 15
Asn Asn Glu Val Pro Thr Asn His Val Gln Tyr Pro Leu Ala Glu Thr
                20                  25                  30

Pro Asn Pro Thr Leu Glu Asp Leu Asn Tyr Lys Glu Phe Leu Arg Met
                35                  40                  45

Thr Ala Asp Asn Asn Thr Glu Ala Leu Asp Ser Ser Thr Thr Lys Asp
                50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                    85                  90                  95

Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
                115                 120                 125

Ala Leu Ala Glu Leu Gln Gly Leu Gln Asn Asn Val Glu Asp Tyr Val
                130                 135                 140

Ser Ala Leu Ser Ser Trp Gln Lys Asn Pro Val Ser Ser Arg Asn Ala
145                 150                 155                 160

His Ser Gln Gly Arg Ile Arg Glu Leu Phe Ser Gln Ala Glu Ser His
                    165                 170                 175

Phe Arg Asn Ser Met Pro Ser Phe Ala Ile Ser Gly Tyr Glu Val Leu
                180                 185                 190

Phe Leu Thr Thr Tyr Ala Gln Ala Ala Asn Thr His Leu Phe Leu Leu
                195                 200                 205

Lys Asp Ala Gln Ile Tyr Gly Glu Glu Trp Gly Tyr Glu Lys Glu Asp
                210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                    245                 250                 255

Ser Ser Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
                275                 280                 285

Arg Leu Tyr Pro Lys Glu Val Lys Thr Glu Leu Thr Arg Asp Val Leu
                290                 295                 300

Thr Asp Pro Ile Val Gly Val Asn Asn Leu Arg Gln Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
                355                 360                 365

Ser Ile Gly Ser Asn Asp Ile Ile Thr Ser Pro Phe Tyr Gly Asn Lys
                370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                    405                 410                 415

Ser Gly Val Thr Lys Val Glu Phe Ser Gln Tyr Asn Asp Gln Thr Asp
                420                 425                 430
```

-continued

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
            485                 490                 495

Ser Val Asp Phe Phe Asn Met Ile Asp Ser Lys Lys Ile Thr Gln Leu
                500                 505                 510

Pro Leu Val Lys Ala Tyr Lys Leu Gln Ser Gly Ala Ser Val Val Ala
                515                 520                 525

Gly Pro Arg Phe Thr Gly Gly Asp Ile Ile Gln Cys Thr Glu Asn Gly
530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 29
<211> LENGTH: 644
<212> TYPE: PRT
<213> ORGANISM: Artificial Sequence
<220> FEATURE:
<223> OTHER INFORMATION: variant Axmi-R1 (R315M)

<400> SEQUENCE: 29

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

```
His Ser Gln Gly Arg Ile Arg Glu Leu Phe Ser Gln Ala Glu Ser His
            165                 170                 175
Phe Arg Asn Ser Met Pro Ser Phe Ala Ile Ser Gly Tyr Glu Val Leu
            180                 185                 190
Phe Leu Thr Thr Tyr Ala Gln Ala Ala Asn Thr His Leu Phe Leu Leu
            195                 200                 205
Lys Asp Ala Gln Ile Tyr Gly Glu Glu Trp Gly Tyr Glu Lys Glu Asp
210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
            245                 250                 255
Ser Ser Tyr Glu Ser Trp Val Asn Phe Asn Arg Tyr Arg Arg Glu Met
            260                 265                 270
Thr Leu Thr Val Leu Asp Leu Ile Ala Leu Phe Pro Leu Tyr Asp Val
            275                 280                 285
Arg Leu Tyr Pro Lys Glu Val Lys Thr Glu Leu Thr Arg Asp Val Leu
            290                 295                 300
Thr Asp Pro Ile Val Gly Val Asn Asn Leu Met Gly Tyr Gly Thr Thr
305                 310                 315                 320
Phe Ser Asn Ile Glu Asn Tyr Ile Arg Lys Pro His Leu Phe Asp Tyr
            325                 330                 335
Leu His Arg Ile Gln Phe His Thr Arg Phe Gln Pro Gly Tyr Tyr Gly
            340                 345                 350
Asn Asp Ser Phe Asn Tyr Trp Ser Gly Asn Tyr Val Ser Thr Arg Pro
            355                 360                 365
Ser Ile Gly Ser Asn Asp Ile Ile Thr Ser Pro Phe Tyr Gly Asn Lys
            370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
            405                 410                 415
Ser Gly Val Thr Lys Val Glu Phe Ser Gln Tyr Asn Asp Gln Thr Asp
            420                 425                 430
Glu Ala Ser Thr Gln Thr Tyr Asp Ser Lys Arg Asn Val Gly Ala Val
            435                 440                 445
Ser Trp Asp Ser Ile Asp Gln Leu Pro Pro Glu Thr Thr Asp Glu Pro
450                 455                 460
Leu Glu Lys Gly Tyr Ser His Gln Leu Asn Tyr Val Met Cys Phe Leu
465                 470                 475                 480
Met Gln Gly Ser Arg Gly Thr Ile Pro Val Leu Thr Trp Thr His Lys
            485                 490                 495
Ser Val Asp Phe Phe Asn Met Ile Asp Ser Lys Lys Ile Thr Gln Leu
            500                 505                 510
Pro Leu Val Lys Ala Tyr Lys Leu Gln Ser Gly Ala Ser Val Val Ala
            515                 520                 525
Gly Pro Arg Phe Thr Gly Gly Asp Ile Ile Gln Cys Thr Glu Asn Gly
            530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
            565                 570                 575
Leu Ser Leu Asp Gly Ala Pro Phe Asn Gln Tyr Tyr Phe Asp Lys Thr
```

580                 585                 590
Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 30
<211> LENGTH: 644
<212> TYPE: PRT
<213> ORGANISM: Artificial Sequence
<220> FEATURE:
<223> OTHER INFORMATION: variant Axmi-R1 (R315W)

<400> SEQUENCE: 30

Met Asn Pro Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
290                 295                 300

```
Thr Asp Pro Ile Val Gly Val Asn Asn Leu Trp Gly Tyr Gly Thr Thr
305                 310                 315                 320

Phe Ser Asn Ile Glu Asn Tyr Ile Arg Lys Pro His Leu Phe Asp Tyr
            325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 31
<211> LENGTH: 644
<212> TYPE: PRT
<213> ORGANISM: Artificial Sequence
<220> FEATURE:
<223> OTHER INFORMATION: variant Axmi-R1 (3c6)

<400> SEQUENCE: 31

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30
```

-continued

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
        130                 135                 140

Ser Ala Leu Ser Ser Trp Gln Lys Asn Gln Glu Ser Ser Arg Asn Leu
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
                180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
        290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
        370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
                420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro

```
                    450                 455                 460
Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                    485                 490                 495

Ser Val Asp Phe Phe Asn Met Ile Asp Ser Lys Lys Ile Thr Gln Leu
                500                 505                 510

Pro Leu Val Lys Ala Tyr Lys Leu Gln Ser Gly Ala Ser Val Val Ala
                515                 520                 525

Gly Pro Arg Phe Thr Gly Gly Asp Ile Ile Gln Cys Thr Glu Asn Gly
530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
                580                 585                 590

Ile Asn Lys Gly Asp Thr Leu Thr Tyr Asn Ser Phe Asn Leu Ala Ser
                595                 600                 605

Phe Ser Thr Pro Phe Glu Leu Ser Gly Asn Asn Leu Gln Ile Gly Val
            610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 32
<211> LENGTH: 644
<212> TYPE: PRT
<213> ORGANISM: Artificial Sequence
<220> FEATURE:
<223> OTHER INFORMATION: variant Axmi-R1 (3a11)

<400> SEQUENCE: 32

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
                 20                  25                  30

Pro Asn Pro Thr Leu Glu Asp Leu Asn Tyr Lys Glu Phe Leu Arg Met
             35                  40                  45

Thr Ala Asp Asn Asn Thr Glu Ala Leu Asp Ser Ser Thr Thr Lys Asp
         50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Lys Ser Ser Gly Asn Pro
145                 150                 155                 160

His Ser Gln Gly Arg Ile Arg Glu Leu Phe Ser Gln Ala Glu Ser His
                165                 170                 175
```

-continued

```
Phe Arg Asn Ser Met Pro Ser Phe Ala Ile Ser Gly Tyr Glu Val Leu
                180                 185                 190

Phe Leu Thr Thr Tyr Ala Gln Ala Ala Asn Thr His Leu Phe Leu Leu
            195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
            275                 280                 285

Arg Leu Tyr Pro Lys Glu Val Lys Thr Glu Leu Thr Arg Asp Val Leu
            290                 295                 300

Thr Asp Pro Ile Val Gly Val Asn Asn Leu Thr Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
            370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
                420                 425                 430

Glu Ala Ser Thr Gln Thr Tyr Asp Ser Lys Arg Asn Val Gly Ala Val
            435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
            515                 520                 525

Gly Pro Arg Phe Thr Gly Gly Asp Ile Ile Gln Cys Thr Glu Asn Gly
            530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
            595                 600                 605
```

```
Phe Ser Thr Pro Phe Glu Leu Ser Gly Asn Asn Leu Gln Ile Gly Val
        610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 33
<211> LENGTH: 644
<212> TYPE: PRT
<213> ORGANISM: Artificial Sequence
<220> FEATURE:
<223> OTHER INFORMATION: variant Axmi-R1 (2b11)

<400> SEQUENCE: 33

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
                 20                  25                  30

Pro Asn Pro Thr Leu Glu Asp Leu Asn Tyr Lys Glu Phe Leu Arg Met
             35                  40                  45

Thr Ala Asp Asn Asn Thr Glu Ala Leu Asp Ser Ser Thr Thr Lys Asp
 50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Ala Tyr Gly Thr Thr
305                 310                 315                 320

Phe Ser Asn Ile Glu Asn Tyr Ile Arg Lys Pro His Leu Phe Asp Tyr
```

```
                    325                 330                 335
Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
        370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Leu Lys Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 34
<211> LENGTH: 644
<212> TYPE: PRT
<213> ORGANISM: Artificial Sequence
<220> FEATURE:
<223> OTHER INFORMATION: variant Axmi-R1 (Q482I)

<400> SEQUENCE: 34

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
                 20                  25                  30

Pro Asn Pro Thr Leu Glu Asp Leu Asn Tyr Lys Glu Phe Leu Arg Met
             35                  40                  45

```
Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480
```

```
Met Ile Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
            515                 520                 525

Gly Pro Arg Phe Thr Gly Gly Asp Ile Ile Gln Cys Thr Glu Asn Gly
        530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
                580                 585                 590

Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
            610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 35
<211> LENGTH: 644
<212> TYPE: PRT
<213> ORGANISM: Artificial Sequence
<220> FEATURE:
<223> OTHER INFORMATION: variant Axmi-R1 (G483K)

<400> SEQUENCE: 35

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
                20                  25                  30

Pro Asn Pro Thr Leu Glu Asp Leu Asn Tyr Lys Glu Phe Leu Arg Met
            35                  40                  45

Thr Ala Asp Asn Asn Thr Glu Ala Leu Asp Ser Thr Thr Lys Asp
 50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
        130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
```

```
            195                 200                 205
Lys Asp Ala Gln Ile Tyr Gly Glu Glu Trp Gly Tyr Glu Lys Glu Asp
    210                 215                 220
Ile Ala Glu Phe Tyr Lys Arg Gln Leu Lys Leu Thr Gln Glu Tyr Thr
225                 230                 235                 240
Asp His Cys Val Lys Trp Tyr Asn Val Gly Leu Asp Lys Leu Arg Gly
                    245                 250                 255
Ser Ser Tyr Glu Ser Trp Val Asn Phe Asn Arg Tyr Arg Arg Glu Met
                260                 265                 270
Thr Leu Thr Val Leu Asp Leu Ile Ala Leu Phe Pro Leu Tyr Asp Val
            275                 280                 285
Arg Leu Tyr Pro Lys Glu Val Lys Thr Glu Leu Thr Arg Asp Val Leu
        290                 295                 300
Thr Asp Pro Ile Val Gly Val Asn Asn Leu Arg Gly Tyr Gly Thr Thr
305                 310                 315                 320
Phe Ser Asn Ile Glu Asn Tyr Ile Arg Lys Pro His Leu Phe Asp Tyr
                    325                 330                 335
Leu His Arg Ile Gln Phe His Thr Arg Phe Gln Pro Gly Tyr Tyr Gly
                340                 345                 350
Asn Asp Ser Phe Asn Tyr Trp Ser Gly Asn Tyr Val Ser Thr Arg Pro
            355                 360                 365
Ser Ile Gly Ser Asn Asp Ile Ile Thr Ser Pro Phe Tyr Gly Asn Lys
        370                 375                 380
Ser Ser Glu Pro Val Gln Asn Leu Glu Phe Asn Gly Glu Lys Val Tyr
385                 390                 395                 400
Arg Ala Val Ala Asn Thr Asn Leu Ala Val Trp Pro Ser Ala Val Tyr
                    405                 410                 415
Ser Gly Val Thr Lys Val Glu Phe Ser Gln Tyr Asn Asp Gln Thr Asp
                420                 425                 430
Glu Ala Ser Thr Gln Thr Tyr Asp Ser Lys Arg Asn Val Gly Ala Val
            435                 440                 445
Ser Trp Asp Ser Ile Asp Gln Leu Pro Pro Glu Thr Thr Asp Glu Pro
        450                 455                 460
Leu Glu Lys Gly Tyr Ser His Gln Leu Asn Tyr Val Met Cys Phe Leu
465                 470                 475                 480
Met Gln Lys Ser Arg Gly Thr Ile Pro Val Leu Thr Trp Thr His Lys
                    485                 490                 495
Ser Val Asp Phe Phe Asn Met Ile Asp Ser Lys Lys Ile Thr Gln Leu
                500                 505                 510
Pro Leu Val Lys Ala Tyr Lys Leu Gln Ser Gly Ala Ser Val Val Ala
            515                 520                 525
Gly Pro Arg Phe Thr Gly Gly Asp Ile Ile Gln Cys Thr Glu Asn Gly
        530                 535                 540
Ser Ala Ala Thr Ile Tyr Val Thr Pro Asp Val Ser Tyr Ser Gln Lys
545                 550                 555                 560
Tyr Arg Ala Arg Ile His Tyr Ala Ser Thr Ser Gln Ile Thr Phe Thr
                    565                 570                 575
Leu Ser Leu Asp Gly Ala Pro Phe Asn Gln Tyr Tyr Phe Asp Lys Thr
                580                 585                 590
Ile Asn Lys Gly Asp Thr Leu Thr Tyr Asn Ser Phe Asn Leu Ala Ser
            595                 600                 605
Phe Ser Thr Pro Phe Glu Leu Ser Gly Asn Asn Leu Gln Ile Gly Val
        610                 615                 620
```

```
Thr Gly Leu Ser Ala Gly Asp Lys Val Tyr Ile Asp Lys Ile Glu Phe
625                 630                 635                 640

Ile Pro Val Asn

<210> SEQ ID NO 36
<211> LENGTH: 644
<212> TYPE: PRT
<213> ORGANISM: Artificial Sequence
<220> FEATURE:
<223> OTHER INFORMATION: variant Axmi-R1 (G483S)

<400> SEQUENCE: 36

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
             20                  25                  30

Pro Asn Pro Thr Leu Glu Asp Leu Asn Tyr Lys Glu Phe Leu Arg Met
         35                  40                  45

Thr Ala Asp Asn Asn Thr Glu Ala Leu Asp Ser Ser Thr Thr Lys Asp
     50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350
```

-continued

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
        370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Ser Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 37
<211> LENGTH: 644
<212> TYPE: PRT
<213> ORGANISM: Artificial Sequence
<220> FEATURE:
<223> OTHER INFORMATION: variant Axmi-R1 (G483Q)

<400> SEQUENCE: 37

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
             20                  25                  30

Pro Asn Pro Thr Leu Glu Asp Leu Asn Tyr Lys Glu Phe Leu Arg Met
         35                  40                  45

Thr Ala Asp Asn Asn Thr Glu Ala Leu Asp Ser Ser Thr Thr Lys Asp
     50                  55                  60

Val Ile Gln Lys Gly Ile Ser Val Val Gly Asp Leu Leu Gly Val Val

-continued

```
                65                  70                  75                  80
Gly Phe Pro Phe Gly Ala Leu Val Ser Phe Tyr Thr Asn Phe Leu
                    85                  90                  95

Asn Thr Ile Trp Pro Ser Glu Asp Pro Trp Lys Ala Phe Met Glu Gln
                    100                 105                 110

Val Glu Ala Leu Met Asp Gln Lys Ile Ala Asp Tyr Ala Lys Asn Lys
                    115                 120                 125

Ala Leu Ala Glu Leu Gln Gly Leu Gln Asn Asn Val Glu Asp Tyr Val
                    130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                    165                 170                 175

Phe Arg Asn Ser Met Pro Ser Phe Ala Ile Ser Gly Tyr Glu Val Leu
                    180                 185                 190

Phe Leu Thr Thr Tyr Ala Gln Ala Ala Asn Thr His Leu Phe Leu Leu
                    195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                    245                 250                 255

Ser Ser Tyr Glu Ser Trp Val Asn Phe Asn Arg Tyr Arg Arg Glu Met
                    260                 265                 270

Thr Leu Thr Val Leu Asp Leu Ile Ala Leu Phe Pro Leu Tyr Asp Val
                    275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                    325                 330                 335

Leu His Arg Ile Gln Phe His Thr Arg Phe Gln Pro Gly Tyr Tyr Gly
                    340                 345                 350

Asn Asp Ser Phe Asn Tyr Trp Ser Gly Asn Tyr Val Ser Thr Arg Pro
                    355                 360                 365

Ser Ile Gly Ser Asn Asp Ile Ile Thr Ser Pro Phe Tyr Gly Asn Lys
                    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                    405                 410                 415

Ser Gly Val Thr Lys Val Glu Phe Ser Gln Tyr Asn Asp Gln Thr Asp
                    420                 425                 430

Glu Ala Ser Thr Gln Thr Tyr Asp Ser Lys Arg Asn Val Gly Ala Val
                    435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gln Ser Arg Gly Thr Ile Pro Val Leu Thr Trp Thr His Lys
                    485                 490                 495
```

```
Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
            515                 520                 525

Gly Pro Arg Phe Thr Gly Gly Asp Ile Ile Gln Cys Thr Glu Asn Gly
            530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
            610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 38
<211> LENGTH: 644
<212> TYPE: PRT
<213> ORGANISM: Artificial Sequence
<220> FEATURE:
<223> OTHER INFORMATION: variant Axmi-R1 (3c7+1g8)

<400> SEQUENCE: 38

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
            35                  40                  45

Thr Ala Asp Asn Asn Thr Glu Ala Leu Asp Ser Ser Thr Thr Lys Asp
        50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
        130                 135                 140

Ser Ala Leu Ser Ser Trp Gln Lys Asn Ala Lys Ser Ser Val Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
            195                 200                 205

Lys Asp Ala Gln Ile Tyr Gly Glu Glu Trp Gly Tyr Glu Lys Glu Asp
        210                 215                 220
```

-continued

```
Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
            245                 250                 255

Ser Ser Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Glu Tyr Gly Thr Thr
305                 310                 315                 320

Phe Ser Asn Ile Glu Asn Tyr Ile Arg Lys Pro His Leu Phe Asp Tyr
            325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
            405                 410                 415

Ser Gly Val Thr Lys Val Glu Phe Ser Gln Tyr Asn Asp Gln Thr Asp
                420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Leu Lys Ser Arg Gly Thr Ile Pro Val Leu Thr Trp Thr His Lys
            485                 490                 495

Ser Val Asp Phe Phe Asn Met Ile Asp Ser Lys Lys Ile Thr Gln Leu
                500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
            565                 570                 575

Leu Ser Leu Asp Gly Ala Pro Phe Asn Gln Tyr Tyr Phe Asp Lys Thr
                580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn
```

<210> SEQ ID NO 39
<211> LENGTH: 644
<212> TYPE: PRT
<213> ORGANISM: Artificial Sequence
<220> FEATURE:
<223> OTHER INFORMATION: variant Axmi-R1 (3c7+2b11)

<400> SEQUENCE: 39

```
Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
             20                  25                  30

Pro Asn Pro Thr Leu Glu Asp Leu Asn Tyr Lys Glu Phe Leu Arg Met
         35                  40                  45

Thr Ala Asp Asn Asn Thr Glu Ala Leu Asp Ser Ser Thr Thr Lys Asp
     50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Ala Lys Ser Ser Val Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
    290                 295                 300

Thr Asp Pro Ile Val Gly Val Asn Asn Leu Arg Ala Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365
```

```
Ser Ile Gly Ser Asn Asp Ile Ile Thr Ser Pro Phe Tyr Gly Asn Lys
        370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
                435                 440                 445

Ser Trp Asp Ser Ile Asp Gln Leu Pro Pro Glu Thr Thr Asp Glu Pro
        450                 455                 460

Leu Glu Lys Gly Tyr Ser His Gln Leu Asn Tyr Val Met Cys Phe Leu
465                 470                 475                 480

Met Leu Lys Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
                515                 520                 525

Gly Pro Arg Phe Thr Gly Gly Asp Ile Ile Gln Cys Thr Glu Asn Gly
        530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
                595                 600                 605

Phe Ser Thr Pro Phe Glu Leu Ser Gly Asn Asn Leu Gln Ile Gly Val
        610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 40
<211> LENGTH: 644
<212> TYPE: PRT
<213> ORGANISM: Artificial Sequence
<220> FEATURE:
<223> OTHER INFORMATION: variant Axmi-R1 (G5+D5D8)

<400> SEQUENCE: 40

Met Asn Pro Asn Asn Arg Ser Glu His Asp Thr Ile Lys Thr Thr Glu
  1               5                  10                  15

Asn Asn Glu Val Pro Thr Asn His Val Gln Tyr Pro Leu Ala Glu Thr
                 20                  25                  30

Pro Asn Pro Thr Leu Glu Asp Leu Asn Tyr Lys Glu Phe Leu Arg Met
             35                  40                  45

Thr Ala Asp Asn Asn Thr Glu Ala Leu Asp Ser Ser Thr Thr Lys Asp
         50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                 85                  90                  95
```

```
Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
        130                 135                 140

Ser Ala Leu Ser Ser Trp Gln Lys Asn Pro Val Ser Ser Arg Asn Ala
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
            260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
        290                 295                 300

Thr Asp Pro Ile Val Gly Val Asn Asn Leu Arg Thr Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
            355                 360                 365

Ser Ile Gly Ser Asn Asp Ile Ile Thr Ser Pro Phe Tyr Gly Asn Lys
        370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
```

-continued

```
                515                 520                 525
Gly Pro Arg Phe Thr Gly Gly Asp Ile Ile Gln Cys Thr Glu Asn Gly
530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
                580                 585                 590

Ile Asn Lys Gly Asp Thr Leu Thr Tyr Asn Ser Phe Asn Leu Ala Ser
                595                 600                 605

Phe Ser Thr Pro Phe Glu Leu Ser Gly Asn Asn Leu Gln Ile Gly Val
610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 41
<211> LENGTH: 644
<212> TYPE: PRT
<213> ORGANISM: Artificial Sequence
<220> FEATURE:
<223> OTHER INFORMATION: variant Axmi-R1 (D4F11+D5D8)

<400> SEQUENCE: 41

Met Asn Pro Asn Asn Arg Ser Glu His Asp Thr Ile Lys Thr Thr Glu
1               5                   10                  15

Asn Asn Glu Val Pro Thr Asn His Val Gln Tyr Pro Leu Ala Glu Thr
                20                  25                  30

Pro Asn Pro Thr Leu Glu Asp Leu Asn Tyr Lys Glu Phe Leu Arg Met
            35                  40                  45

Thr Ala Asp Asn Asn Thr Glu Ala Leu Asp Ser Ser Thr Thr Lys Asp
        50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110

Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
    130                 135                 140

Ser Ala Leu Ser Ser Trp Gln Lys Asn Ala Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
            180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
    210                 215                 220

Ile Ala Glu Phe Tyr Lys Arg Gln Leu Lys Leu Thr Gln Glu Tyr Thr
225                 230                 235                 240
```

```
Asp His Cys Val Lys Trp Tyr Asn Val Gly Leu Asp Lys Leu Arg Gly
            245                 250                 255

Ser Ser Tyr Glu Ser Trp Val Asn Phe Asn Arg Tyr Arg Arg Glu Met
        260                 265                 270

Thr Leu Thr Val Leu Asp Leu Ile Ala Leu Phe Pro Leu Tyr Asp Val
    275                 280                 285

Arg Leu Tyr Pro Lys Glu Val Lys Thr Glu Leu Thr Arg Asp Val Leu
290                 295                 300

Thr Asp Pro Ile Val Gly Val Asn Asn Leu Arg Thr Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
            340                 345                 350

Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 42
<211> LENGTH: 644
```

```
<212> TYPE: PRT
<213> ORGANISM: Artificial Sequence
<220> FEATURE:
<223> OTHER INFORMATION: variant Axmi-R1 (H4+D4A2)

<400> SEQUENCE: 42
```

Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
             20                  25                  30

Pro Asn Pro Thr Leu Glu Asp Leu Asn Tyr Lys Glu Phe Leu Arg Met
         35                  40                  45

Thr Ala Asp Asn Asn Thr Glu Ala Leu Asp Ser Ser Thr Thr Lys Asp
     50                  55                  60

Val

-continued

```
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
            420                 425                 430

Glu Ala Ser Thr Gln Thr Tyr Asp Ser Lys Arg Asn Val Gly Ala Val
        435                 440                 445

Ser Trp Asp Ser Ile Asp Gln Leu Pro Pro Glu Thr Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 43
<211> LENGTH: 644
<212> TYPE: PRT
<213> ORGANISM: Artificial Sequence
<220> FEATURE:
<223> OTHER INFORMATION: variant Axmi-R1 (D4F11+D4A2)

<400> SEQUENCE: 43

Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
    50                  55                  60

Val Ile Gln Lys Gly Ile Ser Val Val Gly Asp Leu Leu Gly Val Val
65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
            100                 105                 110
```

```
Val Glu Ala Leu Met Asp Gln Lys Ile Ala Asp Tyr Ala Lys Asn Lys
        115                 120                 125

Ala Leu Ala Glu Leu Gln Gly Leu Gln Asn Asn Val Glu Asp Tyr Val
130                 135                 140

Ser Ala Leu Ser Ser Trp Gln Lys Asn Ala Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
                180                 185                 190

Phe Leu Thr Thr Tyr Ala Gln Ala Ala Asn Thr His Leu Phe Leu Leu
        195                 200                 205

Lys Asp Ala Gln Ile Tyr Gly Glu Glu Trp Gly Tyr Glu Lys Glu Asp
210                 215                 220

Ile Ala Glu Phe Tyr Lys Arg Gln Leu Lys Leu Thr Gln Glu Tyr Thr
225                 230                 235                 240

Asp His Cys Val Lys Trp Tyr Asn Val Gly Leu Asp Lys Leu Arg Gly
                245                 250                 255

Ser Ser Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
        275                 280                 285

Arg Leu Tyr Pro Lys Glu Val Lys Thr Glu Leu Thr Arg Asp Val Leu
        290                 295                 300

Thr Asp Pro Ile Val Gly Val Asn Asn Leu Arg Gln Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350

Asn Asp Ser Phe Asn Tyr Trp Ser Gly Asn Tyr Val Ser Thr Arg Pro
                355                 360                 365

Ser Ile Gly Ser Asn Asp Ile Ile Thr Ser Pro Phe Tyr Gly Asn Lys
        370                 375                 380

Ser Ser Glu Pro Val Gln Asn Leu Glu Phe Asn Gly Glu Lys Val Tyr
385                 390                 395                 400

Arg Ala Val Ala Asn Thr Asn Leu Ala Val Trp Pro Ser Ala Val Tyr
                405                 410                 415

Ser Gly Val Thr Lys Val Glu Phe Ser Gln Tyr Asn Asp Gln Thr Asp
                420                 425                 430

Glu Ala Ser Thr Gln Thr Tyr Asp Ser Lys Arg Asn Val Gly Ala Val
                435                 440                 445

Ser Trp Asp Ser Ile Asp Gln Leu Pro Pro Glu Thr Thr Asp Glu Pro
450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
                500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
530                 535                 540
```

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
            565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
            595                 600                 605

Phe Ser Thr Pro Phe Glu Leu Ser Gly Asn Asn Leu Gln Ile Gly Val
            610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 44
<211> LENGTH: 1166
<212> TYPE: PRT
<213> ORGANISM: Bacillus thuringiensis

<400> SEQUENCE: 44

Met Ser Pro Asn Asn Gln Asn Glu Tyr Glu Ile Lys Asp Ala Thr Pro
1               5                   10                  15

Ser Thr Ser Val Ser Ser Asp Ser Ala Arg Tyr Pro Phe Ala Asn Glu
                20                  25                  30

Pro Thr Asn Ala Leu Gln Asn Met Asn Tyr Lys Glu Tyr Leu Arg Met
            35                  40                  45

Ser Glu Gly His Asp Ala Ala Tyr Phe Ser Asn Pro Glu Ala Phe Val
    50                  55                  60

Asp Thr Lys Ser Ile Gln Ala Ile Asn Val Ile Gly Lys Ala Leu
65                  70                  75                  80

Gly Ala Leu Gly Val Pro Gly Ala Gly Ile Ile Ala Ser Phe Tyr Ser
                85                  90                  95

Phe Ile Val Gly Gln Leu Trp Pro Ser Asn Ser Val Ser Leu Trp Glu
            100                 105                 110

Gln Ile Met Glu Gln Val Glu Glu Leu Ile Asp Gln Lys Ile Thr Glu
        115                 120                 125

Tyr Ala Arg Asn Lys Ala Leu Thr Glu Leu Lys Gly Leu Gly Asp Ala
    130                 135                 140

Leu Asp Val Tyr Gln Glu Ser Leu Glu Ala Trp Leu Glu Asn Arg Asn
145                 150                 155                 160

Asp Thr Arg Ala Arg Ser Val Val Ser Lys Gln Phe Ile Ala Leu Glu
                165                 170                 175

Leu Asp Phe Val Gly Ala Ile Pro Ser Phe Ala Val Ser Asn Gln Glu
            180                 185                 190

Val Pro Leu Leu Ala Val Tyr Ala Gln Ala Ala Asn Leu His Leu Leu
        195                 200                 205

Leu Leu Arg Asp Ala Ser Ile Phe Gly Ala Asp Trp Gly Phe Ser Ser
    210                 215                 220

Ser Glu Ile Ser Thr Tyr Tyr Asn Arg Gln Val Arg Leu Thr Ser Gln
225                 230                 235                 240

Tyr Ser Asp Tyr Cys Val Lys Trp Tyr Asn Thr Gly Leu Asp Lys Leu
                245                 250                 255

Lys Gly Thr Asn Ser Ala Ser Trp Leu Lys Tyr His Gln Phe Arg Arg
            260                 265                 270

-continued

```
Glu Met Thr Leu Met Val Leu Asp Val Val Ala Leu Phe Pro Asn Tyr
        275                 280                 285
Asn Thr Gln Thr Tyr Pro Ile Glu Thr Arg Ala Gln Leu Thr Arg Asp
    290                 295                 300
Val Tyr Thr Asp Pro Ala Ala Phe Asn Asn Val Ser Asp Tyr Gly Phe
305                 310                 315                 320
Cys Asn Pro Trp Ser Thr His Ser Gly Ile Leu Phe Ser Glu Val Glu
                325                 330                 335
Asn Ala Val Ile Arg Ser Pro His Leu Phe Asp Ile Leu Ser Ser Ile
                340                 345                 350
Glu Ile Asn Thr Ala Arg Gly Gly Ile Ala Leu Asn Asn Thr Ala Tyr
                355                 360                 365
Ile Asn Tyr Trp Ser Gly His Ser Leu Lys Tyr His Glu Thr Asn Asn
    370                 375                 380
Pro Thr Ile Arg Ala Val Asn Tyr Gly Arg Ile Thr Ser Glu Lys Asn
385                 390                 395                 400
Ser Leu Val Leu Glu Asp Arg Glu Ile Phe Glu Thr Ile Ser Val Val
                405                 410                 415
Ala Asn Leu Ala Asn Val Tyr Gln Lys Ala Tyr Gly Val Pro Glu Ser
                420                 425                 430
Tyr Phe Asn Met Thr Arg Arg Gly Thr Ser Ser Thr Ser Tyr Tyr Phe
                435                 440                 445
Tyr Ser Lys Thr His Thr Thr Pro Tyr Gly Cys Ser Asp Val Tyr Pro
                450                 455                 460
Ser Tyr Ser Asp Ile Pro Ile Asp Arg Asn Val Pro Val Ala Glu Ser
465                 470                 475                 480
Tyr Ser His Arg Leu Ser His Ile Thr Phe His Ser Phe Ser Lys Asn
                485                 490                 495
Ser Asn Ala Ile Tyr Gly Ser Phe Pro Val Phe Val Trp Thr His Val
                500                 505                 510
Ser Ala Asp Leu Thr Asn Thr Ile Tyr Pro Asp Ala Ile Thr Gln Leu
                515                 520                 525
Pro Met Val Lys Ala Asn Ala Leu Leu Ser Gly Thr Ser Val Ile Lys
530                 535                 540
Gly Pro Gly Ser Thr Gly Gly Asp Ile Leu Arg Arg Thr Ser Val Gly
545                 550                 555                 560
Arg Val Gly Asn Phe Lys Val Asn Val Asn Gly Pro Leu Thr Gln Arg
                565                 570                 575
Tyr Leu Val Arg Ile Arg Tyr Ala Ser Thr Thr Asp Leu Asp Phe Tyr
                580                 585                 590
Val Tyr Arg Gly Gly Thr Thr Val Ser Asn Tyr Arg Phe Asn Lys Thr
                595                 600                 605
Met Asn Lys Gly Ala Ser Leu Thr Tyr Asp Ile Phe Lys Phe Ala Ser
    610                 615                 620
Phe Ser Thr Pro Phe Thr Phe Thr Lys Thr Gln Asp Glu Leu Gly Ile
625                 630                 635                 640
Ser Ile Gln Asn Phe Ser Ser Gly Glu Glu Val Tyr Ile Asp Arg Ile
                645                 650                 655
Glu Val Ile Pro Val Gly Thr Thr Tyr Glu Ala Glu Thr Asp Leu Glu
                660                 665                 670
Ile Ala Lys Arg Ala Val Asn Thr Leu Phe Thr Asn Thr Lys Asp Gly
                675                 680                 685
Leu Arg Pro Gly Val Thr Asp Tyr Glu Val Asn Gln Ala Ala Asn Leu
            690                 695                 700
```

```
Val Glu Cys Leu Ser Asp Asp Leu Tyr Pro Asn Glu Lys Arg Leu Leu
705                 710                 715                 720

Phe Asp Ala Val Lys Glu Ala Lys Arg Leu Ser Gly Val Arg Asn Leu
            725                 730                 735

Leu Gln Asp Ser Asp Phe Gln Glu Ile Asn Gly Glu Asn Gly Trp Thr
        740                 745                 750

Gly Ser Thr Gly Ser Thr Gly Ile Glu Ile Val Glu Gly Asp Ala Leu
    755                 760                 765

Phe Lys Gly Arg Tyr Leu Arg Leu Pro Gly Ala Pro Glu Ile Asp Thr
        770                 775                 780

Glu Thr Tyr Pro Thr Tyr Leu Tyr Gln Lys Ile Asp Glu Gly Leu Leu
785                 790                 795                 800

Lys Pro Tyr Thr Arg Tyr Arg Leu Arg Gly Phe Val Gly Ser Ser Gln
                805                 810                 815

Gly Leu Glu Ile Tyr Thr Ile Arg His Gln Thr Asn Arg Ile Val Lys
                820                 825                 830

Asn Val Pro Asp Asp Leu Leu Pro Asp Val Ser Leu Val Ser Ala Gly
            835                 840                 845

Asp Gly Ile Asn Arg Cys Ser Glu Gln Lys Tyr Val Asn Ser Arg Leu
        850                 855                 860

Glu Gly Glu Arg Gly Leu Pro Asn Gly Asn Arg Ser Ala Asp Ala His
865                 870                 875                 880

Glu Phe Ser Ile Gln Ile Asp Thr Gly Glu Ile Asp Leu Asn Gly Asn
            885                 890                 895

Glu Gly Ile Trp Val Gly Phe Lys Val Ala Thr Pro Asp Gly Tyr Ala
        900                 905                 910

Thr Leu Gly Asn Leu Glu Leu Val Glu Glu Gly Pro Leu Ser Gly Asp
        915                 920                 925

Ala Leu Glu Arg Val Gln Arg Glu Glu Gln Trp Lys Ile Arg Met
930                 935                 940

Thr Lys Arg Arg Glu Glu Thr Asp Arg Lys Tyr Thr Ala Ala Lys Gln
945                 950                 955                 960

Ala Val Asp Arg Leu Tyr Ala Asp Tyr Gln Asp Gln Leu Asn Pro
                965                 970                 975

Asn Val Glu Ile Thr Asp Ile Thr Ala Ala Gln Asn Leu Ile Gln Ser
            980                 985                 990

Ile Pro Tyr Val Tyr Asn Asp Val Phe Pro Gly Leu Pro Gly Met Asn
        995                 1000                1005

Tyr Ala Lys Tyr Thr Glu Leu Thr Asn Arg Leu Gln Gln Ala Trp Ser
    1010                1015                1020

Leu Tyr Glu Gln Arg Asn Val Ile Pro Asn Gly Asp Phe Arg Asn Glu
1025                1030                1035                1040

Leu Asn Asn Trp Asn Thr Thr Ser Gly Val Asn Val Gln Gln Ile Asn
            1045                1050                1055

Asp Arg Ser Val Leu Val Ile Pro Asn Trp Asp Glu Gln Val Ser Gln
        1060                1065                1070

Gln Phe Thr Val Gln Pro Asn Gln Arg Tyr Val Leu Arg Val Thr Ala
        1075                1080                1085

Arg Lys Glu Gly Val Gly Asn Gly Tyr Val Ser Ile Arg Asp Gly Gly
        1090                1095                1100

Asn Gln Thr Glu Thr Leu Thr Phe Ser Ala Asn Glu Tyr Asp Thr Asn
1105                1110                1115                1120

Gly Val Tyr Asn Asp Gln Ile Gly Tyr Ile Thr Lys Thr Val Ala Phe
```

```
                    1125                1130                1135
Ile Pro Tyr Thr Asp Gln Val Trp Met Asp Ile Ser Glu Thr Glu Gly
                1140                1145                1150

Val Leu Tyr Ile Glu Gly Val Lys Leu Val Val Asp Val Glu
                1155                1160                1165

<210> SEQ ID NO 45
<211> LENGTH: 1168
<212> TYPE: PRT
<213> ORGANISM: Bacillus thuringiensis

<400> SEQUENCE: 45

Met Lys Val Arg Leu Leu Met Asn Lys Asn Tyr Leu Ser Lys Ser Gln
  1               5                  10                  15

Asp Leu Thr Gln Ile Ser Glu Ile Phe Gly Tyr Asp Pro Ile His Pro
             20                  25                  30

Leu Val Asn Pro Lys Asn His Ile Glu Ser Leu Arg Val Asn Arg Asn
         35                  40                  45

Glu Leu Arg Thr Leu Pro Glu Gly Phe Ala Ser Ser Thr Glu Ser Ala
 50                  55                  60

Ile Thr Asn Thr Leu Asn Ile Ile Ser Ile Leu Leu Asp Ala Ser Gly
 65                  70                  75                  80

His Pro Ala Ala Ala Arg Val Leu Gly Val Ile Thr Gly Ile Ile Gly
                 85                  90                  95

Ile Leu Trp Pro Gly Gly Ser Gln Lys Thr Trp Glu Glu Phe Met Ala
            100                 105                 110

Ala Val Glu Ala Leu Ile Asp Glu Lys Ile Thr Glu Ser Phe Lys Asn
        115                 120                 125

Glu Ala Ile Ser Lys Leu Asn Gly Leu Ala Asp Leu Tyr Thr Val Tyr
    130                 135                 140

Leu Ser Glu Leu Glu Leu Trp Leu Glu His Pro His Asp Pro Ser Ile
145                 150                 155                 160

Ile Gln Ser Val Arg Thr Arg Phe Leu Asp Leu Asp Ser Glu Phe Ile
                165                 170                 175

Ser Ser Met Pro Gln Phe Ala Ile Ser Gly Phe Glu Val Ser Phe Leu
            180                 185                 190

Pro Val Tyr Ala Gln Ala Ala Asn Leu His Leu Leu Leu Leu Arg Asp
        195                 200                 205

Leu Ser Tyr Tyr Gly Asn Asp Trp Gly Leu Gln Gln Pro Glu Ile Glu
    210                 215                 220

Asn Tyr Tyr Asn Arg Gln Ile Asn Asn Ile Gln Lys Tyr Thr Asp His
225                 230                 235                 240

Cys Val Lys Trp Tyr Gln Leu Gly Leu Gln Asp Val Tyr Asn Lys Tyr
                245                 250                 255

Asn Ser Thr Ile Ile Asn Glu Asp Gly Gly Leu Pro Trp Thr His Tyr
            260                 265                 270

Asn Arg Tyr Arg Arg Glu Met Thr Ile Leu Val Leu Asp Leu Val Ala
        275                 280                 285

Thr Phe Ser Thr Asn Asp Trp Lys Lys Tyr Tyr Leu Glu Thr Asn Val
    290                 295                 300

Glu Leu Ser Arg Glu Ile Tyr Thr Asp Pro Leu Gly Tyr Glu Asp Ser
305                 310                 315                 320

Asp Glu Gly Asn Ile Thr Asp Val Asp Trp Tyr Ser Glu Gly Val Ser
                325                 330                 335

Phe Ser Thr Ile Glu Asn Leu His Ser Pro Lys Leu Val Glu Trp Leu
```

```
                340             345             350
Lys Arg Ile Thr Ile Gln Thr Asp Tyr Phe Ser Ala Gly Ser Asp Glu
            355             360             365
Ser Tyr Cys Trp Ala Gly His Tyr Ile Tyr Thr Thr Phe Thr Asp Ser
        370             375             380
Asp Lys Glu Tyr Ser Arg Tyr Gly Asn Pro Glu Asn Val Glu Ser
385             390             395             400
Thr Thr Ser Tyr Thr Phe Ala Pro Ala Glu Val Tyr Lys Val Glu Ser
                405             410             415
Val Val Gly Ser Glu Arg Asn Ala Thr Tyr Asp Asn Tyr Val Asn Ser
            420             425             430
Ala Asn Thr Phe Tyr Gln Val Thr Pro Thr Asn Glu Leu Lys Lys Phe
            435             440             445
Ile Tyr Ser Tyr Arg Asn Asp Tyr Asp Lys Lys Thr Leu Tyr Ser Asp
        450             455             460
Asp Gln Leu Pro Leu Glu Thr Asp Pro Lys Tyr Gly Glu Tyr Ser
465             470             475             480
His Arg Leu Ser Asn Ile Thr Cys Ala Pro Leu Asn Ser Asp Asp Phe
                485             490             495
Gly Leu Val Pro Ile Leu Gly Trp Thr His Thr Ser Leu Lys Arg Glu
            500             505             510
Asn Ile Ile Tyr Pro Asp Lys Ile Thr Gln Ile Pro Ala Val Lys Ser
            515             520             525
Phe Ser Thr Glu Gly Thr Trp Glu Arg Val Ala Ala Gly Pro Gly Phe
        530             535             540
Thr Gly Gly Asn Val Thr Gln Ala Thr Asn Thr Val Thr Ser Gly Ile
545             550             555             560
Lys Thr Thr Asp Leu Val Lys Ile Arg Val Arg Ile Asp Ser Thr Ala
                565             570             575
Ser Ser Lys Gln Tyr Arg Val Arg Leu Arg Tyr Ala Ser Asn Gln Asp
            580             585             590
Phe Ser His Ala His Phe Tyr Thr Gly Thr Gly Ser Asn Glu Thr Thr
            595             600             605
Phe Ser Leu Lys Lys Thr Thr Asp Phe Pro Phe Ala Asn Tyr Asn Ser
        610             615             620
Phe Gly Tyr Val Glu Ile Pro Arg Val Leu Lys Phe Ser Ser Gly Ser
625             630             635             640
Glu Ile Ile Asn Val Tyr Val Tyr Pro Glu Asn Gly Leu Lys Val Gln
                645             650             655
Val Asp Lys Ile Glu Phe Ile Pro Val Asp Asp Asn Tyr Glu Asp Arg
            660             665             670
Val Thr Leu Glu Lys Ala Gln Lys Ala Val Asn Thr Leu Phe Thr Val
            675             680             685
Gly Arg Asn Ala Leu Gln Thr Asp Val Thr Asp Tyr Lys Val Asp Gln
        690             695             700
Val Ser Ile Leu Val Asp Cys Val Ser Glu Glu Leu Tyr Pro Asn Glu
705             710             715             720
Lys Lys Glu Leu Gln Asn Leu Val Lys Tyr Ala Lys Arg Leu Ser Ile
                725             730             735
Ser Arg Asn Leu Leu Asp Pro Asn Phe Thr Ser Ile Asn Ala Pro
            740             745             750
Lys Ile Arg Gly Trp His Gly Ser Gln Gly Ile Phe Val Gly Asn Gly
            755             760             765
```

```
Asn Tyr Ile Phe Lys Gly Pro Tyr Val His Leu Gln Gly Thr Asn Asp
        770                 775                 780

Ala Gln Tyr Pro Thr Tyr Leu Tyr Gln Lys Ile Asp Glu Ser Lys Leu
785                 790                 795                 800

Lys Glu Tyr Ile Arg Tyr Lys Leu Arg Gly Phe Ile Glu Ser Ser Gln
                805                 810                 815

Asp Leu Glu Val Tyr Val Ile Arg Tyr Asp Val Lys Arg Glu Thr Leu
            820                 825                 830

Asp Val Ser Asn Asn Leu Ser Ser Asp Asp Thr Pro Ala Asn Ala Cys
        835                 840                 845

Gly Gly Pro Asn Arg Cys Ile Glu Gln Gln Tyr Leu Asp Asp Asn Pro
    850                 855                 860

Thr Leu Glu Cys Ser Ser Ile Gln Asp Gly Ile Leu Phe Asp Ser His
865                 870                 875                 880

Ser Phe Ser Leu Asn Ile Asp Thr Gly Ser Ile Asp Tyr Asn Glu Asn
                885                 890                 895

Val Gly Ile Trp Val Val Phe Lys Ile Ser Thr Leu Glu Gly Tyr Ala
            900                 905                 910

Lys Leu Gly Asn Val Glu Val Ile Glu Asp Gly Pro Leu Val Gly Glu
        915                 920                 925

Ala Leu Ala Arg Val Lys Arg Gln Glu Thr Lys Trp Arg Asn Lys Leu
    930                 935                 940

Ala Gln Leu Arg Thr Glu Thr Gln Ala Ile Tyr Thr Arg Ala Lys Gln
945                 950                 955                 960

Ser Leu Asp Asn Leu Phe Ile Asp Ala Gln Asp Ala His Leu Lys Ile
                965                 970                 975

Gly Thr Pro Phe Ala Ala Ile Val Ala Ala Arg Glu Ala Val Gln Ser
            980                 985                 990

Ile Arg Glu Val Tyr Met Pro Trp Leu Ser Val Val Ala Gly Val Asn
        995                 1000                1005

Tyr Pro Ile Phe Thr Glu Leu Asn Leu Arg Val Arg Arg Ala Leu Gln
    1010                1015                1020

Leu Tyr Asp Leu Arg Asn Val Val Arg Asn Gly Arg Phe Arg Asn Gly
1025                1030                1035                1040

Leu Ser Asn Trp Asn Val Thr Ser Asp Val Glu Val Gln Glu Glu Asn
                1045                1050                1055

Gly Asn Asn Val Leu Val Leu Ser Asn Trp Asp Ala Gln Val Leu Gln
            1060                1065                1070

Cys Ile Lys Leu Tyr Gln Asp Arg Gly Tyr Ile Leu Arg Val Thr Ala
        1075                1080                1085

Arg Lys Glu Gly Leu Gly Glu Gly Tyr Ile Thr Ile Thr Asp Glu Glu
    1090                1095                1100

Gly Asn Thr Asp Gln Leu Thr Phe Gly Ser Cys Glu Glu Ile Asp Ala
1105                1110                1115                1120

Ser Asn Ser Phe Val Ser Thr Gly Tyr Met Thr Lys Glu Leu Glu Phe
                1125                1130                1135

Phe Pro Asp Thr Glu Lys Val Arg Ile Glu Ile Gly Thr Glu Gly
            1140                1145                1150

Thr Phe Lys Val Glu Ser Val Glu Leu Phe Leu Met Glu Asp Leu Cys
        1155                1160                1165

<210> SEQ ID NO 46
<211> LENGTH: 1134
<212> TYPE: PRT
<213> ORGANISM: Bacillus thuringiensis
```

<400> SEQUENCE: 46

```
Met Met Asp Val Asn Lys Phe Tyr Gly Ser Arg Asn Val Asn Arg Met
 1               5                   10                  15

Leu Asn Asn Pro Phe Asn Asn Ser Thr Gln Lys Glu Leu Leu Pro Val
             20                  25                  30

Val Thr Gln Asn Pro Cys Val Asp Asn Pro Phe Val Asn Lys Ile Asn
         35                  40                  45

Gln Thr Glu Met Leu Thr Asn Thr Ser Ile Ala Leu Asn Thr Val Ala
     50                  55                  60

Gly Val Thr Gly Ala Val Leu Gly Ser Leu Gly Val Pro Gly Ala Ser
 65                  70                  75                  80

Leu Ile Thr Ser Phe Tyr Gln Lys Val Leu Gly Leu Leu Trp Pro Thr
                 85                  90                  95

Asn Ser Arg Ala Glu Ile Trp Asp Ser Phe Ile Ser Val Val Glu Asp
             100                 105                 110

Leu Ile Lys Lys Glu Val Glu Asn Tyr Ala Arg Glu Lys Ala Ile Thr
         115                 120                 125

Glu Leu Glu Gly Leu Gly Asp Asn Met Lys Asp Tyr Lys Ser Lys Leu
     130                 135                 140

Gln Gln Trp Leu Asp Thr Pro Asn Asp Asp Thr Lys Arg Ser Leu Lys
145                 150                 155                 160

His Tyr Met Glu Ser Leu Asp Met Asp Phe Lys Glu His Met Pro Gln
                165                 170                 175

Phe Arg Ile Lys Gly Tyr Glu Val Gln Leu Leu Pro Val Phe Ala His
            180                 185                 190

Ala Ala Asn Leu His Leu Ser Leu Phe Arg Asp Met Val Leu Tyr Gly
        195                 200                 205

Pro Asp Leu Gly Phe Thr Pro Glu Asp Leu Ser Glu Asp Tyr Gln Gln
    210                 215                 220

Leu Gln Gln Arg Ile Ile Asp Tyr Thr Asn His Cys Asn Leu Tyr Phe
225                 230                 235                 240

Glu Gln Gly Leu Ser Ser Leu Lys Lys Ser Ser Tyr Glu Glu Trp Val
                245                 250                 255

Ile Tyr Asn Arg Phe Arg Arg Glu Met Thr Leu Met Val Leu Asp Ile
            260                 265                 270

Ile Ala Gln Phe Pro Tyr Tyr Asp Val Lys Lys Tyr Pro Lys Pro Val
        275                 280                 285

Ser Thr Gln Leu Thr Arg Glu Val Tyr Thr Asp Pro Leu Ile Thr Ser
    290                 295                 300

Phe Phe Gln Pro Gly Gln Gly Pro Asn Phe Ser Phe Met Glu Ser Asn
305                 310                 315                 320

Ala Ile Arg Asn Pro His Leu Val Thr Tyr Leu Asp Ser Leu Tyr Ile
                325                 330                 335

Tyr Thr Ala Lys Phe Arg Ala Tyr Ser Gln Glu Ile Gln Pro Asp Leu
            340                 345                 350

Tyr Phe Trp Thr Ala His Lys Gly Lys Tyr Lys Leu Ser Ala Ser Thr
        355                 360                 365

Asp Val His Asp Thr Ala Leu Tyr Gly Ser Thr Ser Gly Ser Ile Ser
    370                 375                 380

Glu Lys Asn Tyr Ser Phe Asn Gly Asn Ile Tyr Gln Thr Leu Ala
385                 390                 395                 400

Ala Pro Ser Ala Val Phe Thr Thr Ser Lys Gln Tyr Tyr Gly Ile Glu
                405                 410                 415
```

```
Gln Val Glu Phe Tyr Gly Asp Lys Gly Lys Ile His Tyr Tyr Gly Asp
            420                 425                 430
Arg Lys Tyr Pro Leu Ser Val Asp Ser Ala Asn Gln Leu Pro Pro Asp
            435                 440                 445
Glu Glu Pro Ile Ser Glu Asn Tyr Asp His Ile Leu Thr His Ala Ser
            450                 455                 460
Ala Val Asn Val Leu Asp Gly Gly Thr Val Pro Ile Phe Ala Trp Thr
465                 470                 475                 480
His Arg Ser Ala Asp Tyr Tyr Asn Thr Ile Tyr Ser Asp Lys Ile Thr
                485                 490                 495
Gln Ile Pro Ala Val Lys Ile Asn Lys Leu Glu Asn Pro Ser Thr Val
                500                 505                 510
Val Lys Gly Pro Gly Phe Thr Gly Gly Asp Leu Val Lys Arg Gly Ser
                515                 520                 525
Thr Gly Ile Leu Gly Tyr Leu Asn Val Thr Val Asn Ser Pro Leu Ser
            530                 535                 540
Gln Arg Tyr Ala Val Lys Ile Arg Tyr Ala Ser Thr Ile Ser Gly Asp
545                 550                 555                 560
Phe His Val Gln Ile Asp Gly Val Ala Thr Leu Glu Gly His Cys Glu
                565                 570                 575
Ser Thr Ile Asn Ser Gly Asp Glu Leu Ser Phe Glu Ser Phe Ser Tyr
            580                 585                 590
Lys Glu Phe Ser Thr Thr Val Gln Phe Thr Gly Asn Lys Pro Arg Leu
            595                 600                 605
Arg Leu Ser Leu Asp Lys Val Ala Gly Thr Gly Val Phe Tyr Phe Asp
            610                 615                 620
Lys Ile Glu Phe Ile Pro Val Asp Val Asn Tyr Asp Glu Arg Val Gln
625                 630                 635                 640
Leu Glu Lys Ala Gln Lys Ser Val Asn Ala Leu Phe Thr Ala Gly Arg
                645                 650                 655
His Ala Leu Gln Thr Asp Val Thr Asp Phe Lys Val Asp Gln Val Ser
                660                 665                 670
Ile Leu Val Asp Cys Val Ser Gly Glu Leu Tyr Pro Asn Glu Lys Arg
            675                 680                 685
Glu Leu Leu Ser Leu Val Lys Tyr Ala Lys Arg Leu Ser Tyr Ser Arg
            690                 695                 700
Asn Leu Leu Leu Asp Pro Thr Phe Asp Ser Ile Asn Ser Ser Glu Glu
705                 710                 715                 720
Asn Gly Trp His Gly Ser Asn Gly Ile Val Ile Gly Asn Gly Asn Phe
                725                 730                 735
Val Phe Lys Gly Asn Tyr Leu Ile Phe Ser Gly Thr Asn Asp Thr Gln
                740                 745                 750
Tyr Pro Thr Tyr Leu Tyr Gln Lys Ile Asp Glu Ser Lys Leu Lys Glu
            755                 760                 765
Tyr Thr Arg Tyr Lys Leu Arg Gly Phe Ile Glu Asn Ser Gln Asp Leu
            770                 775                 780
Glu Ala Tyr Val Val Arg Tyr Asp Ala Lys His Glu Thr Leu Asp Val
785                 790                 795                 800
Ser Asp Asn Leu Tyr Pro Asp Ile Ser Pro Val Asn Ala Cys Gly Glu
                805                 810                 815
Pro Asn Arg Cys Ala Ala Leu Pro Tyr Leu Asp Glu Asn Pro Arg Leu
                820                 825                 830
Glu Cys Ser Ser Ile Gln Asp Gly Ile Leu Ser Asp Ser His Ser Phe
```

```
                 835                 840                 845
Ser Leu Asn Ile Asp Thr Gly Ser Ile Asp Ser Asn Glu Asn Val Gly
    850                 855                 860

Ile Trp Val Leu Phe Lys Ile Ser Thr Pro Glu Gly Tyr Ala Lys Phe
865                 870                 875                 880

Gly Asn Leu Glu Val Ile Glu Asp Gly Pro Val Ile Gly Glu Ala Leu
                885                 890                 895

Ala Arg Val Lys Arg Gln Glu Thr Lys Trp Arg Asn Lys Leu Ala Gln
            900                 905                 910

Leu Arg Thr Glu Thr Gln Ala Ile Tyr Thr Arg Ala Lys Gln Ala Ile
        915                 920                 925

Asp Asn Leu Phe Thr Asn Ala Gln Asp Ser His Leu Lys Ile Gly Ala
    930                 935                 940

Thr Phe Ala Ser Ile Val Ala Ala Arg Lys Ile Val Gln Ser Ile Arg
945                 950                 955                 960

Glu Ala Tyr Met Ser Trp Leu Ser Ile Val Pro Gly Val Asn Tyr Pro
                965                 970                 975

Ile Phe Thr Glu Leu Asn Glu Arg Val Gln Gln Ala Phe Gln Leu Tyr
            980                 985                 990

Asp Val Arg Asn Val Val Arg Asn Gly Arg Phe Leu Asn Gly Val Ser
        995                 1000                1005

Asp Trp Ile Val Thr Ser Asp Val Lys Val Gln Glu Asn Gly Asn
    1010                1015                1020

Asn Val Leu Val Leu Ser Asn Trp Asp Ala Gln Val Leu Gln Cys Leu
1025                1030                1035                1040

Lys Leu Tyr Gln Asp Arg Gly Tyr Ile Leu Arg Val Thr Ala Arg Lys
            1045                1050                1055

Glu Gly Leu Gly Glu Gly Tyr Ile Thr Ile Thr Asp Glu Ala Gly His
        1060                1065                1070

Thr Asp Gln Leu Thr Phe Gly Thr Cys Glu Glu Ile Asp Ala Ser Asn
    1075                1080                1085

Thr Phe Val Ser Thr Gly Tyr Met Thr Lys Glu Leu Glu Phe Phe Pro
    1090                1095                1100

Asp Thr Glu Lys Val Arg Ile Glu Ile Gly Glu Thr Glu Gly Ile Phe
1105                1110                1115                1120

Gln Val Glu Ser Val Glu Leu Phe Leu Met Glu Asp Leu Cys
                1125                1130

<210> SEQ ID NO 47
<211> LENGTH: 1144
<212> TYPE: PRT
<213> ORGANISM: Bacillus thuringiensis

<400> SEQUENCE: 47

Met Asp Gln Gln Asn Glu Tyr Glu Ile Ile Gln Ala Gly Val Ser Asn
 1               5                  10                  15

Ala Ile Thr Asp Thr Phe Gln Arg Tyr Pro Leu Ala Asn Asn Pro Asn
            20                  25                  30

Thr Ser Phe Gln Asn Met Asn Tyr Lys Asp Tyr Leu Asn Asp Pro Met
        35                  40                  45

Phe Leu Gly Glu Thr Arg Asp Ala Gln Thr Ala Ile Thr Thr Ser Leu
    50                  55                  60

Glu Ile Ile Ser Glu Ile Leu Gly Phe Leu Gly Val Pro Phe Val Gly
65                  70                  75                  80

Pro Ile Ile Gly Phe Thr Asn Arg Leu Ile Asn Leu Leu Trp Pro Arg
```

-continued

```
                    85                  90                  95
Asn Thr Thr Asp Ile Trp Asn Ala Phe Met Asp Glu Val Gln Ala Leu
                100                 105                 110

Ile Asn Glu Ser Ile Thr Lys Ala Val Arg Ser Lys Ala Ile Ser Glu
            115                 120                 125

Leu Glu Gly Ile His Gln Val Tyr Arg Leu Tyr Ile Glu Ala Leu Asn
        130                 135                 140

Glu Trp Lys Asp Thr Pro Asp Asn Pro Phe Val Gln Glu Arg Val Arg
145                 150                 155                 160

Thr Thr Phe Arg Asp Val Asn Ser Ile Ile Asn Tyr Ala Met Pro Ser
                165                 170                 175

Phe Arg Val Gln Gly Phe Glu Ile Pro Leu Leu Val Val Tyr Ala Gln
                180                 185                 190

Ala Ala Asn Leu His Leu Val Leu Leu Arg Asp Ala Thr Leu Phe Gly
            195                 200                 205

Ala Gly Trp Gly Phe Thr Glu Thr Asn Ile Asn Asp Arg Tyr Asn Glu
        210                 215                 220

Gln Val Arg Val Thr Asn Gly Tyr Ile Asp His Cys Thr Lys Trp Tyr
225                 230                 235                 240

Asn Glu Gly Leu Thr Arg Leu Lys Asn Asn Trp Ser Lys Tyr His Gln
                245                 250                 255

Phe Arg Arg Glu Met Thr Leu Met Val Leu Asp Leu Ile Ala Leu Phe
                260                 265                 270

Pro Ser His Asp Ala Arg Arg Tyr Pro Met Glu Thr Ser Ala Gln Leu
            275                 280                 285

Thr Arg Asp Val Tyr Thr Asp Pro Ile Gly Tyr Arg Gly Asn Ala Asn
        290                 295                 300

Phe Ser Asp Pro Trp Thr Asn His Val Ser Phe Ser Lys Ala Glu Ser
305                 310                 315                 320

Glu Thr Ile Arg Pro Pro His Leu Phe Asp Thr Leu Glu Ser Val Glu
                325                 330                 335

Ile Asn Thr Ala Lys Ala Met Leu Pro Leu Asn Asp Lys Ser Tyr Met
            340                 345                 350

Tyr Tyr Trp Ala Gly His Thr Val Thr Ser Arg Leu Leu Asp Ser Ser
        355                 360                 365

Gly Asn Pro Leu Lys Tyr Thr Tyr Gly Ser Met Thr Ser Glu Lys Asn
    370                 375                 380

Leu Val Ser Leu Pro Gly Lys Asp Val Tyr Arg Ile Asn Ser Val Ala
385                 390                 395                 400

Ser Gly Phe Ser Asn Tyr Tyr Ala Lys Leu Tyr Gly Val Ser Lys Val
                405                 410                 415

Asp Phe Ser Ile Val Asp Arg Asn Asn Ser Asn Lys Thr Thr Tyr Ser
            420                 425                 430

Tyr Ser Lys Ser Ser Thr Val Pro Ser Asp Asn Lys Glu Asn Arg Asp
        435                 440                 445

Ser Glu Asn Glu Leu Pro Gln Thr Thr Thr Asp Gln Pro Asp Tyr Lys
    450                 455                 460

Gly Tyr Ser His Arg Leu Ser His Ile Thr Phe Ile Ser Ser Ala Ile
465                 470                 475                 480

Pro Thr Tyr Val Trp Thr Arg Lys Ser Ala Asp Leu Thr Asn Thr Ile
                485                 490                 495

Tyr Pro Asp Lys Ile Thr Gln Ile Pro Ala Val Lys Met Tyr Glu Leu
            500                 505                 510
```

-continued

```
Gly Ser Ser Ala Val Val Lys Gly Pro Gly Phe Thr Gly Gly Asp
        515                 520                 525
Leu Val Lys Arg Thr Asn Asn Gly Ser Leu Gly Arg Phe Lys Ile Thr
    530                 535                 540
Ile Asp Ser Pro Gly Ala His Arg Tyr Arg Leu Arg Val Arg Tyr His
545                 550                 555                 560
Ser Asp Val Ser Gly Val Phe His Met Gln Ile Asn Asn Val Glu Thr
                565                 570                 575
Ile Gln Gly Glu Phe Lys Ser Thr Val Asp Ser Thr Ser Thr Met Ser
            580                 585                 590
Asn Asp Ser Phe Gln Leu Arg Glu Phe Thr Thr Thr Phe Arg Phe Pro
        595                 600                 605
Ser Asn Val Thr Asp Ile Lys Val Ser Leu Gly Ala Ile Asn Gly Gln
    610                 615                 620
Gly Asn Phe Tyr Leu Asp Arg Ile Glu Phe Ala Pro Val Asp Thr Asn
625                 630                 635                 640
Tyr Asp Glu Arg Ile Thr Leu Glu Lys Ala Gln Lys Ala Val Asn Ala
                645                 650                 655
Leu Phe Thr Glu Gly Arg Asn Ala Leu Gln Thr Asp Met Thr Asp Tyr
            660                 665                 670
Lys Val Asp Gln Val Ser Ile Leu Val Asp Cys Val Ser Gly Glu Val
        675                 680                 685
Tyr Pro Asn Glu Lys Arg Glu Leu Leu Asn Leu Val Lys Tyr Ala Lys
    690                 695                 700
Arg Leu Ser Ile Ala Arg Asn Leu Leu Val Asp Pro Asn Phe Thr Ser
705                 710                 715                 720
Ile His Ala Ser Met Tyr Ser Glu Asp Val Lys Gly Trp Tyr Gly Ser
                725                 730                 735
Asn Gly Ile Ala Thr Gly Ser Gly Asp Val Val Leu Lys Glu Asn Tyr
            740                 745                 750
Val Ser Leu Pro Ser Thr Ser Asp Ala Gln Tyr Pro Thr Tyr Leu Tyr
        755                 760                 765
Gln Lys Ile Asp Glu Ser Lys Leu Lys Ala Tyr Thr Arg Tyr Lys Leu
    770                 775                 780
Arg Gly Phe Ile Glu Asn Ser Gln Asp Leu Glu Ala Tyr Val Val Arg
785                 790                 795                 800
Tyr Asp Ala Lys His Glu Thr Leu Asp Val Ser Asn Asn Leu Leu Pro
                805                 810                 815
Asp Val Leu Pro Val Asn Ala Cys Gly Glu Pro Asp Arg Cys Ala Ala
            820                 825                 830
Leu Gln Tyr Leu Asp Glu Asn Pro Arg Leu Glu Cys Ser Ser Ile Gln
        835                 840                 845
Asp Gly Ile Leu Ser Asp Ser His Ser Phe Ser Leu Asn Ile Asp Thr
    850                 855                 860
Gly Ser Met Asp Leu Asn Glu Asn Leu Gly Ile Trp Val Leu Phe Lys
865                 870                 875                 880
Ile Ser Thr Pro Glu Gly Tyr Ala Lys Phe Gly Asn Leu Glu Val Ile
                885                 890                 895
Glu Asp Gly Thr Val Ser Gly Glu Ala Leu Ala Arg Val Lys Arg Gln
            900                 905                 910
Glu Thr Lys Trp Arg Asn Lys Leu Ala Gln Leu Arg Thr Glu Thr Gln
        915                 920                 925
Ala Ile Tyr Thr Arg Ala Lys Gln Ala Leu Asp Asn Leu Phe Thr Asp
    930                 935                 940
```

```
Ala Gln Asp Ser Tyr Leu Lys Ile Gly Ala Thr Phe Ala Ala Ile Val
945                 950                 955                 960

Ala Ala Arg Lys Ile Val Gln Ser Ile Arg Glu Ala Tyr Met Ser Trp
            965                 970                 975

Leu Ser Val Val Pro Gly Val Asn Tyr Pro Ile Phe Thr Glu Leu Asn
        980                 985                 990

Glu Arg Val Gln Arg Ala Phe Gln Leu Tyr Asp Gly Arg Asn Val Val
    995                 1000                1005

Arg Asn Gly Arg Phe Leu Asn Gly Val Leu Asp Trp Ile Val Thr Ser
    1010                1015                1020

Asp Val Ser Val Gln Glu Glu Asn Gly Asn Asn Val Leu Val Leu Ser
1025                1030                1035                1040

Asn Trp Asp Ala Gln Val Leu Gln Cys Leu Lys Leu Tyr Gln Asp Arg
            1045                1050                1055

Gly Tyr Ile Leu Arg Val Thr Ala Arg Lys Glu Gly Leu Gly Glu Gly
            1060                1065                1070

Tyr Ile Thr Ile Thr Asp Glu Glu Gly Asn Thr Asp Gln Leu Thr Phe
            1075                1080                1085

Gly Ser Cys Glu Glu Ile Asp Thr Ser Asn Ser Phe Val Ser Thr Gly
            1090                1095                1100

Tyr Met Thr Lys Glu Leu Glu Phe Phe Pro Asp Thr Glu Lys Val Arg
1105                1110                1115                1120

Ile Glu Ile Glu Glu Thr Glu Gly Thr Phe Lys Val Glu Ser Val Glu
            1125                1130                1135

Leu Phe Leu Met Glu Asp Leu Cys
            1140

<210> SEQ ID NO 48
<211> LENGTH: 1196
<212> TYPE: PRT
<213> ORGANISM: Bacillus thuringiensis

<400> SEQUENCE: 48

Met Ser Pro Asn Gln Asn Glu Tyr Glu Ile Ile Asp Thr Pro Ser
 1               5                  10                  15

Ser Asn Ser Leu Asp Asn Gln Phe Val Arg Tyr Pro Leu Ala Lys Glu
            20                  25                  30

Pro Thr Gln Val Arg Gln Asn Leu Asn Tyr Lys Asp Trp Leu Asn Ser
        35                  40                  45

Leu Asp Glu Asn Asn Asn Gln Ser Phe Gly Val Thr Pro Arg Arg Ala
    50                  55                  60

Ser Val Val Gly Ala Val Gly Ser Ile Leu Gly Ala Thr Leu Gly Thr
65                  70                  75                  80

Ile Pro Tyr Val Gly Asp Ile Leu Ala Leu Ile Val Gly Ile Phe Trp
                85                  90                  95

Pro Glu Gly Ser Asp Pro Glu Asp Tyr Ser Glu Leu Ile Asn Ala Ile
            100                 105                 110

Met Glu Gln Val Glu Leu Leu Ile Asp Gln Lys Ile Ser Glu Gln Val
            115                 120                 125

Arg Asn Asp Ala Leu Ala Thr Leu Glu Ser Ser Gly Ile Ala Leu Gln
    130                 135                 140

Ala Tyr Leu Asn Ala Leu Glu Asp Trp Lys Ile Asn Pro Asn Asn Ala
145                 150                 155                 160

Arg Ser Thr Gln Leu Val Arg Glu Arg Phe Thr Phe Ala Glu Ala Gln
                165                 170                 175
```

```
Val Arg Thr Asn Ile Ala Tyr Val Ser Arg Lys Asp Tyr Glu Ile Leu
            180                 185                 190

Leu Leu Pro Ile Tyr Ala Gln Val Ala Asn Ile His Leu Leu Leu Leu
            195                 200                 205

Lys Gln Val Gln Leu Tyr Gly Thr Lys Leu Gly Tyr Thr Gln Asn Asp
            210                 215                 220

Ile Asp Leu Ile Tyr Glu Glu Gln Lys Lys Phe Thr Ala Gln Tyr Thr
225                 230                 235                 240

Asn His Cys Thr Asn Trp Tyr Asn Ile Gly Leu Asn Asn Ile Trp Glu
                245                 250                 255

Ser Ile Ala Gly Thr Ser Tyr Ser Gly Ser Arg Trp Asp Glu Phe Asn
                260                 265                 270

Asp Phe Arg Arg Asp Leu Thr Leu Thr Val Leu Asp Ile Val Ser Thr
                275                 280                 285

Phe Pro Ile His Asp Thr Arg Leu Tyr Pro Glu Lys Val Asn Gly Gln
                290                 295                 300

Leu Thr Arg Glu Ile Tyr Thr Arg Ser Ile Asn Val Asn Tyr Phe Asn
305                 310                 315                 320

Gln Val Ser Ala Arg Thr Ile Glu Asp Ala Glu Arg Leu Leu Thr Asn
                325                 330                 335

Pro Pro Arg Leu Leu Pro Trp Ile Glu Gln Leu Glu Phe Asn Thr Asn
                340                 345                 350

Val Asn Phe Ser Val Asn Trp Lys Phe Leu Thr Ser Thr Arg Arg Arg
                355                 360                 365

Phe Ile Tyr Thr Asn Ser Ser Asp Leu Asn Tyr Asp Gly Tyr Ala Gly
                370                 375                 380

Tyr His Leu Asp Gly Thr Ser Asn Ser Phe Leu Tyr Pro Ser Asn Asn
385                 390                 395                 400

Glu Arg Ile Tyr Thr Ile Thr Ala Gln Arg Phe Gly Glu Gln Arg Asn
                405                 410                 415

Ile Pro Gln Ala Ile Thr Gly Leu Thr Phe Ser Met Asn Thr Gly Arg
                420                 425                 430

Thr Tyr Arg Tyr Ser Ser Asn Thr Pro Ala Gly Pro Ser Ile Ile Thr
                435                 440                 445

Glu Asp Tyr His Leu Pro Gly Leu Asn Gly Glu Glu Val Pro Asn Ser
                450                 455                 460

Asn Asn Phe Ser His Phe Leu Arg Ser Ile Asn Gly Tyr Ser Asn Gly
465                 470                 475                 480

Asn Gln Arg Ile Phe His Ser Phe Gly Trp Thr His Ala Ser Val Asp
                485                 490                 495

Phe Glu Asn Lys Ile Tyr Pro Thr Ile Thr Gln Ile Pro Ala Val
                500                 505                 510

Lys Ala Ile Gln Gly Thr Met Pro Tyr Pro Val Val Lys Gly Pro Gly
                515                 520                 525

Phe Thr Gly Gly Asp Ile Ala Arg Leu Pro Asn Asn Pro Thr Leu Gly
                530                 535                 540

Leu Trp Phe Asn Gly Thr Met Glu Ser Leu Gly Ser Gly His Asp Pro
545                 550                 555                 560

Ala Pro Arg Tyr Arg Val Arg Ile Arg Tyr Ala Ser Gln Ser Gly Gly
                565                 570                 575

Ser Ala Asn Phe Arg Phe Met Ser Ser Asn Gly Gln Asn Ser Ser Gln
                580                 585                 590

Gln Asn Phe Ser Phe Thr Ser Thr Met Thr Thr Gly Glu Pro Ser Lys
```

```
                    595                 600                 605
Tyr Glu Asp Phe Arg Phe Ser Val Leu Pro Asn Ile Val Thr Pro Leu
610                 615                 620

Ser Phe Asn Val Ser Trp His Leu Val Ala Ser Asn Ala Asn Pro Asn
625                 630                 635                 640

Asn Asn Val Tyr Ile Asp Arg Ile Glu Phe Ile Pro Glu Phe Leu Met
                    645                 650                 655

Ala Arg Ser Asp Leu Glu Thr Ala Lys Lys Ala Val Asn Glu Leu Phe
                660                 665                 670

Thr Asn Thr Lys Asn Ser Leu Arg Arg Glu Val Thr Asp Tyr Gln Val
            675                 680                 685

Ser Gln Ala Val Ser Leu Val Glu Cys Leu Ser Asp Glu Leu Tyr Pro
        690                 695                 700

Asn Glu Lys Arg Met Leu Ile Asp Ala Val Lys Glu Ala Lys Arg Leu
705                 710                 715                 720

Ser Glu Ala Arg Asn Leu Leu Gly Asp Ile Asp Leu Lys Val Ile Ser
                    725                 730                 735

Glu Tyr Gly Glu Asp Gly Trp Ile Gly Ser Lys Gly Ile Glu Val Ala
                740                 745                 750

Lys Ser Asn Pro Leu Tyr Lys Asn Asp Leu Leu Arg Leu Pro Lys Val
            755                 760                 765

Arg Glu Ile Glu Gly Glu Ile Tyr Pro Thr Tyr Leu Tyr Tyr Lys Val
        770                 775                 780

Asp Glu Ser Leu Leu Lys Pro Tyr Thr Arg Tyr Lys Phe Arg Gly Phe
785                 790                 795                 800

Ile Glu Ser Ser Arg Asp Leu Glu Ile Phe Val Ile Arg His Gln Ala
                    805                 810                 815

Tyr Arg Val Val Lys Asn Val Pro Ser Asn Leu Leu Ser Asp Ile Gly
                820                 825                 830

Pro Val Asn Ala Cys Gly Gly Phe Asp Arg Cys Ser Glu Gln Lys Tyr
            835                 840                 845

Val Asn Ser Met Leu Glu Leu Asp Asn Asp Leu Ser Asn Glu Asn Arg
        850                 855                 860

Ser Ser Glu Ala His Glu Phe Ser Ile His Val Asp Thr Gly Glu Leu
865                 870                 875                 880

Asn Tyr Ser Glu Asn Pro Gly Ile Trp Val Ala Phe Lys Ile Thr Lys
                    885                 890                 895

Met Asp Gly Tyr Ala Thr Val Gly Asn Leu Glu Leu Val Glu Val Glu
                900                 905                 910

Thr Leu Ser Gly Glu Ala Leu Glu Arg Val Gln Arg Gln Lys Gln
            915                 920                 925

Trp Gln Gly Gln Leu Ala Thr Arg Arg Lys Glu Thr Glu Thr Arg Tyr
        930                 935                 940

Gly Pro Ala Lys Gln Ala Ile Asp Arg Leu Phe Val Asp Tyr Gln Asp
945                 950                 955                 960

Arg Gln Leu Tyr Ser Gly Thr Lys Ile Ser Asp Leu Ile Ala Ala Gln
                    965                 970                 975

Asn Leu Val Gln Ser Ile Pro Tyr Val Tyr Asn Asp Met Leu Pro Glu
                980                 985                 990

Ile Pro Gly Met Asn Tyr Thr Ser Val Thr Glu Leu Thr Asn Arg Leu
            995                 1000                1005

Gln Gln Ala Trp Asn Leu Tyr Asp Gln Arg Asn Ser Ile Gln Asn Gly
        1010                1015                1020
```

```
Asp Phe Arg Lys Asp Ile Asn Asn Trp Asn Val Thr Asn Gly Val Asn
1025                1030                1035                1040

Ile Gln Gln Met Asn Asp Thr Ser Val Leu Val Ile Pro Asn Trp Asp
            1045                1050                1055

Ser Gln Val Ser Gln Gln Ile Thr Val Gln Pro Asn Arg Arg Tyr Val
        1060                1065                1070

Leu Arg Val Thr Ala Arg Lys Glu Gly Ser Gly Asp Gly Tyr Val Thr
            1075                1080                1085

Ile Arg Asp Gly Ala Lys Tyr Thr Glu Thr Leu Thr Phe Asn Thr Cys
        1090                1095                1100

Asp Tyr Asn Gly Ser Asn Val Tyr Gln Glu Gln Ala Leu Tyr Thr Asn
1105                1110                1115                1120

Asp Val Tyr Asn Thr Gln Ser Ala Asn Ile His Gly Ser Asn Ser Ala
            1125                1130                1135

Tyr His Thr Gln Ala Ser Asn Thr Asp Arg Tyr Asn Met Asn Gly Met
                1140                1145                1150

Tyr Asn Asp Gln Thr Ser Tyr Val Thr Lys Thr Val Glu Phe Ile Pro
            1155                1160                1165

Asn Thr Glu Gln Val Trp Ile Glu Met Ser Glu Thr Gly Val Phe
            1170                1175                1180

Tyr Ile Glu Ser Val Glu Leu Ile Val Glu Glu Asn
1185                1190                1195

<210> SEQ ID NO 49
<211> LENGTH: 1226
<212> TYPE: PRT
<213> ORGANISM: Bacillus thuringiensis

<400> SEQUENCE: 49

Met Lys Asn Val Trp Lys Val Ile Leu Cys Ser Lys Cys Ile Gly Gly
1               5                   10                  15

Lys Lys Met Ser Pro Asn Asn Gln Asn Glu Phe Asp Ile Ile Asp Val
                20                  25                  30

Pro Ser Asn Thr Ser Ile Ser Thr Asn Phe Val Arg Tyr Pro Phe Val
            35                  40                  45

Asn Asp Pro Asn Ser Asn Thr Leu Gln Asn Lys Asn Tyr Lys Asp Phe
50                  55                  60

Leu Thr Met Ser Glu Lys Ser Asn Ser Gly Tyr Leu Thr Asp Pro Glu
65                  70                  75                  80

Ala Phe Asp Asp Val Gly Ser Ala Ile Phe Ala Gly Leu Ser Ile Thr
                85                  90                  95

Ala Lys Ile Met Asp Ala Phe Asp Val Pro Gly Gly Asp Ile Phe Asn
            100                 105                 110

Gly Leu Leu Glu Ile Ile Gly Ile Leu Trp Asp Leu Gln Asp Asp Thr
        115                 120                 125

Trp Glu Ala Phe Met Glu Gln Val Glu Val Leu Ile Asp Gln Lys Ile
    130                 135                 140

Ala Glu Tyr Ala Arg Asn Leu Ala Leu Thr Asn Leu Lys Gly Leu Glu
145                 150                 155                 160

Asn Ser Tyr Lys Leu Tyr Leu Glu Ala Leu Ala Asp Trp Lys Gln Asn
                165                 170                 175

Pro Thr Ser Pro Ser Ser Gln Glu Arg Val Arg Thr Arg Phe Arg Asp
            180                 185                 190

Thr Asp Asp Ser Leu Thr Val Phe Met Pro Ser Phe Ala Val Lys Gly
        195                 200                 205
```

```
Tyr Glu Ile Pro Leu Leu Ala Val Tyr Ala Gln Ala Ala Asn Leu His
    210                 215                 220

Leu Leu Leu Leu Arg Asp Ser Ala Ala Tyr Gly Leu Gly Trp Gly Leu
225                 230                 235                 240

Ser Gln Leu Asn Val Asn Asp Asn Tyr Asn Arg Gln Val Arg Leu Thr
                245                 250                 255

Gly Glu Tyr Thr Asn His Cys Val Ser Trp Tyr Thr Thr Gly Leu Glu
                260                 265                 270

Lys Leu Arg Gly Ser Asn Ala Gln Ser Trp Ile Lys Phe Asn Arg Tyr
            275                 280                 285

Arg Arg Glu Met Thr Val Met Val Leu Asp Ile Val Ala Leu Phe Pro
        290                 295                 300

Asn Tyr Asp Ala Arg Arg Tyr Pro Gln Ala Thr Thr Thr Glu Leu Thr
305                 310                 315                 320

Arg Leu Ile Tyr Thr Asp Pro His Gly Tyr Thr Ile Tyr Ser Pro Thr
                325                 330                 335

Ser Gln Thr Thr Ile Pro Trp Tyr Glu Tyr Gly Gln Ser Phe Ser Glu
                340                 345                 350

Ile Glu Asn Val Ala Ile Gln Ala Pro Arg Leu Phe Arg Trp Ala Gln
            355                 360                 365

Lys Leu Gln Ile Tyr Ser Lys Phe Val Arg His Ala Pro Gln Glu Ser
        370                 375                 380

His Tyr Trp Ser Gly His Thr Phe Thr Phe His His Thr Arg Asp Asp
385                 390                 395                 400

Thr Lys Thr Ser Leu Thr Tyr Gly Asp Ile Ile Asp Tyr Lys Tyr Leu
                405                 410                 415

Ser Glu Ala Asp Leu Ser Asn Thr Asp Ile Tyr Lys Val Ser Ser Leu
            420                 425                 430

Val Ala Ser Ser Trp Gly Ser Gly Val Arg Leu Leu Val Thr Lys Ala
        435                 440                 445

Ile Phe Glu Thr Ile Asn Thr Ser Asn Lys Leu Ile Asp Tyr Glu Tyr
        450                 455                 460

Asp Leu Gln Leu Leu Ser Asn Phe Phe Asn Glu Trp Lys Asn Thr Glu
465                 470                 475                 480

Ala Glu Leu Pro Ile Gln Ile Val Asn Pro Pro Ile Phe Gly Asp Phe
                485                 490                 495

Asn Gln Tyr Ser His Arg Val Ala Tyr Ile Ser His Ala Pro Ile Gln
            500                 505                 510

Pro Tyr Ser Gly Ala Phe Arg Asn Tyr Gly Leu Val Pro Val Tyr Gly
        515                 520                 525

Trp Ser His Val Ser Val Asp Arg Asn Asn Thr Ile Tyr Ala Asp Arg
530                 535                 540

Ile Ser Gln Ile Pro Ala Val Lys Ala Val Gln Gly Ser Gly Glu Pro
545                 550                 555                 560

Tyr Pro Val Val Arg Gly Pro Gly Phe Thr Gly Gly Asp Ile Ala Arg
                565                 570                 575

Leu Pro Asn Asn Pro Asn Val Gly Leu Trp Phe Asn Ser Lys Val Glu
            580                 585                 590

Ser Thr Ala Leu Asn Lys Arg Phe Arg Val Arg Ile Arg Tyr Ala Cys
        595                 600                 605

Ala Thr Gly Ala Arg Ala Asp Phe Gly Gly Leu Thr Leu Pro Ile Thr
        610                 615                 620

Val Gln Phe Asn Gln Thr Met Ser Thr Thr Thr Pro Thr Arg Tyr Glu
625                 630                 635                 640
```

```
Asp Phe Gln Tyr Val Asp Ile Ser Gly Ser Phe Leu Leu Thr Asn Thr
                645                 650                 655

Asn Ser Gly Phe Ser Leu Val Ala Gln Ser Ala Asn Gln Thr Asn Asn
            660                 665                 670

Leu Phe Ile Asp Lys Ile Glu Phe Ile Pro Glu Asn Pro Ala Leu Glu
                675                 680                 685

Ala Glu Ser Asp Leu Glu Ala Ala Lys Lys Ala Val Asn Ala Leu Phe
        690                 695                 700

Thr Asn Arg Lys Asn Val Leu Gln Thr Gly Val Thr Asp Tyr Gln Ile
705                 710                 715                 720

Asn Gln Ala Ala Asn Leu Ile Glu Cys Val Ser Asp Glu Val Tyr Pro
                725                 730                 735

Asn Glu Lys Arg Leu Leu Phe Asp Ala Val Lys Glu Ala Lys Arg Leu
            740                 745                 750

Ser Ala Thr Arg Asn Leu Leu Glu Asp Thr Asp Phe His Ala Ile Asn
                755                 760                 765

Gly Gly Asn Gly Trp Thr Gly Ser Thr Gly Ile Glu Ile Val Glu Gly
        770                 775                 780

Asp Ile Leu Phe Lys Asp Arg Ser Leu Arg Leu Pro Ser Ala Arg Glu
785                 790                 795                 800

Thr Asp Arg Glu Ile Tyr Pro Thr Tyr Ile Tyr Gln Lys Ile Asp Glu
                805                 810                 815

Ser Arg Leu Lys Gln Asn Thr Arg Tyr Ser Leu Arg Gly Phe Ile Gly
            820                 825                 830

Ser Ser Gln Asp Leu Glu Ile Tyr Val Leu Arg His Gln Ala Tyr Arg
        835                 840                 845

Val Ile Lys Asn Val Ser Asp Asn Leu Leu Pro Asn Ile Arg Pro Ile
850                 855                 860

Asn Ala Cys Gly Gly Val Asp Arg Cys Ser Gln Gln Lys Tyr Val Asn
865                 870                 875                 880

Asn Ser Leu Glu Val Asn Ser Gly Leu Ser Asn Gly Ile Gly Ala Ser
                885                 890                 895

Asp Ser His Glu Phe Ser Ile His Val Asp Thr Gly Glu Leu Asn Tyr
        900                 905                 910

Asn Glu Asn Thr Gly Ile Trp Val Val Phe Lys Ile Ala Thr Thr Asn
            915                 920                 925

Gly Tyr Ala Thr Leu Gly Asn Leu Glu Leu Val Glu Glu Gly Pro Leu
        930                 935                 940

Ser Gly Asp Ala Leu Glu Arg Val Lys Asn Gln Glu Lys Gln Trp Gln
945                 950                 955                 960

Asp Gln Met Thr Arg Arg Arg Ala Glu Thr Asn Arg Tyr Gly Leu
                965                 970                 975

Ala Lys Gln Ala Val Asp Arg Leu Phe Val Asp Tyr Gln Asp Gln Gln
        980                 985                 990

Val Ser Pro Ile Ile Glu Ile Ser Asp Leu Thr Ala Ala Gln Asn Val
            995                 1000                1005

Val Gln Ser Ile Pro Tyr Val Tyr Asn Asp Met Leu Pro Glu Ile Pro
        1010                1015                1020

Gly Met Asn Tyr Thr Ser Val Thr Glu Leu Thr Asn Arg Leu Gln Gln
1025                1030                1035                1040

Ala Trp Asp Leu Tyr Asp Gln Arg Asn Ser Ile Gln Asn Gly Asp Phe
                1045                1050                1055

Arg Asn Asp Val Ser Asn Trp Asn Val Thr Pro Glu Val Asn Ile Gln
```

```
                1060            1065            1070
Gln Met Asn Asp Thr Ser Val Leu Val Ile Pro Asn Trp Asp Ser Gln
        1075            1080            1085

Ala Ser Gln Gln Ile Thr Val Gln Pro Asn Arg Arg Tyr Val Leu Arg
        1090            1095            1100

Val Thr Ala Arg Lys Glu Gly Ser Gly Asp Gly Tyr Val Thr Ile Arg
1105            1110            1115            1120

Asp Gly Ala Lys Tyr Thr Glu Thr Leu Thr Phe Asn Thr Cys Asp Tyr
            1125            1130            1135

Asn Gly Ser Ser Val Tyr Gln Glu Gln Ala Leu Tyr Thr Asn Asp Val
            1140            1145            1150

Tyr Asn Thr Gln Ser Ala Asn Ile His Gly Ser Asn Ser Ala Tyr His
            1155            1160            1165

Thr Gln Ala Ser Asn Thr Asp Arg Tyr Asn Met Asn Gly Met Tyr Asn
        1170            1175            1180

Asp Gln Thr Ser Tyr Val Thr Lys Thr Val Glu Phe Ile Pro Asn Thr
1185            1190            1195            1200

Glu Gln Val Trp Ile Glu Met Ser Glu Thr Glu Gly Val Phe Tyr Ile
            1205            1210            1215

Glu Ser Val Glu Leu Ile Val Glu Glu Asn
            1220            1225

<210> SEQ ID NO 50
<211> LENGTH: 1169
<212> TYPE: PRT
<213> ORGANISM: Bacillus thuringiensis

<400> SEQUENCE: 50

Met Ser Pro Asn Asn Gln Asn Glu Tyr Glu Ile Ile Asp Ala Thr Pro
  1               5                  10                  15

Ser Thr Ser Val Ser Asn Asp Ser Thr Lys Tyr Pro Tyr Ala Asn Glu
                20                  25                  30

Pro Thr Asn Ala Leu Gln Asn Met Asn Tyr Lys Asp Tyr Leu Arg Met
            35                  40                  45

Ser Glu Gly Tyr Asp Asn Lys Tyr Phe Ala Asn Pro Glu Val Phe Ala
 50                  55                  60

Ala Pro Gly Gly Ile Thr Thr Gly Ile Thr Val Thr Lys Leu Leu
 65                  70                  75                  80

Gly Trp Leu Gly Leu Pro Phe Ala Gly Glu Thr Gly Met Ala Leu Asn
                85                  90                  95

Phe Ile Leu Gly Leu Leu Trp Pro Thr Ser Gly Asn Pro Trp Ala Glu
            100                 105                 110

Leu Met Ile Leu Val Glu Glu Leu Ile Asn Gln Lys Ile Glu Glu Ala
            115                 120                 125

Val Arg Asn Lys Ala Leu Ala Asp Leu Ala Asn Ser Gly Arg Ala Leu
130                 135                 140

Gln Ser Tyr Leu Asn Ala Phe Glu Asp Trp Gln Lys Asn Pro Asn Ile
145                 150                 155                 160

Phe Arg Ser Lys Glu Leu Val Arg Glu Arg Phe Ala Asn Ala Glu His
                165                 170                 175

Ser Leu Arg Thr Glu Met Ser Ser Phe Ala Ile Arg Gly Phe Glu Ile
            180                 185                 190

Pro Leu Leu Ala Thr Tyr Ala Gln Ala Ala Asn Leu His Leu Phe Leu
            195                 200                 205

Ile Lys Asp Val Gln Ile Tyr Gly Lys Glu Trp Gly Tyr Thr Gln Ala
```

```
                210                 215                 220
Asp Ile Asp Leu Phe Tyr Arg Glu Gln Val Glu Phe Thr Lys Glu Tyr
225                 230                 235                 240

Thr Glu His Cys Ile Asn Ile Tyr Asn Asp Gly Leu Asn Gln Leu Lys
                245                 250                 255

Gly Ser Asn Ala Lys Gln Trp Ile Ala Phe Asn Arg Phe Arg Arg Glu
                260                 265                 270

Met Thr Leu Thr Val Leu Asp Val Ala Leu Phe Ser Asn Tyr Asp
                275                 280                 285

Val Arg Met Tyr Pro Ile Lys Thr Thr Thr Glu Leu Thr Arg Thr Ile
290                 295                 300

Tyr Thr Asp Pro Leu Gly Tyr Thr Lys Thr Gly Ser Ser Ser Thr Pro
305                 310                 315                 320

Pro Trp Tyr Asn Tyr Gly Ser Ser Phe Ser Tyr Ile Glu Ser Val Ala
                325                 330                 335

Ile Pro Ala Pro Ser Leu Val Lys Trp Leu Ser Gln Ile Glu Ile Tyr
                340                 345                 350

Ser Lys Ser Ala Lys Ala Thr Pro Gln Ser Ala Asp Tyr Trp Ala Gly
                355                 360                 365

His Thr Ile Thr Tyr His Tyr Gly Gly Asp Asn Gly Gln Ala Val Ala
                370                 375                 380

Asn Tyr Gly Asp Arg Thr Asn Pro Val Ala Val Asp Arg Tyr Asn Phe
385                 390                 395                 400

Glu Gln Ala Asp Ile Tyr Arg Val Ser Ser Val Ala Ser Ser Thr
                405                 410                 415

Thr Ser Gly Val Lys Leu Leu Thr Thr Lys Ala Ile Phe Asp Gly Ile
                420                 425                 430

Asn Thr Lys Asn Gly Leu Val Ser Tyr Arg Tyr Glu Lys Ser Ser Asn
                435                 440                 445

Phe Phe Asn Glu Leu Lys Asp Thr Ile Thr Glu Leu Pro Val Gln Leu
                450                 455                 460

Ser Ser Pro Pro Thr Tyr Gly Asp Ala Glu Gln Tyr Ser His Arg Leu
465                 470                 475                 480

Ser Tyr Val Ser Asn Ala Pro Thr Glu Tyr Ser Ser Gly Gly His Leu
                485                 490                 495

Ile Leu Gly Leu Ile Pro Val Leu Gly Trp Thr His Thr Ser Leu Thr
                500                 505                 510

Gln Thr Asn Gln Ile His Ser Asp Ser Ile Thr Gln Ile Pro Ala Val
                515                 520                 525

Lys Val Ser Asn Leu Glu Ser Gly Thr Ser Val Val Ala Asn Pro Gly
530                 535                 540

Phe Thr Gly Gly Asp Leu Leu Lys Arg Thr Ser Thr Gly Arg Met Gly
545                 550                 555                 560

Thr Leu Lys Leu Thr Val Ala Gly Ile Leu Ser Arg Glu Met Thr Ile
                565                 570                 575

Arg Ile Arg Tyr Ala Ala Thr Thr Asp Phe Lys Leu Gln Val Ile Tyr
                580                 585                 590

Lys Gly Ile Leu Gln Ser Ser Tyr Asn Ser Asn Lys Thr Met Asn Lys
                595                 600                 605

Gly Glu Asn Leu Thr Tyr Gly Lys Phe Lys Phe Ala Asn Phe Thr Leu
                610                 615                 620

Pro Ile Ser Leu Leu Ile Pro Ser Asp Leu Ser Ile Asp Val Gln Asn
625                 630                 635                 640
```

-continued

```
Leu Ser Ser Gly Glu Glu Val Tyr Ile Asp Arg Ile Glu Phe Ile Pro
            645                 650                 655
Val Gly Ala Thr Tyr Glu Ala Glu Gln Asp Leu Glu Asn Ala Lys Lys
        660                 665                 670
Ala Val Asn Ala Leu Phe Thr Asn Thr Lys Asp Gly Leu Arg Pro Gly
            675                 680                 685
Val Thr Asp Tyr Glu Val Asn Gln Ala Ala Asn Leu Val Glu Cys Leu
        690                 695                 700
Ser Asp Asp Leu Tyr Pro Asn Glu Lys Arg Leu Leu Phe Asp Ala Val
705                 710                 715                 720
Arg Glu Ala Lys Arg Leu Ser Glu Ala Arg Asn Leu Leu Gln Asp Pro
                725                 730                 735
Asp Phe Gln Glu Ile Asn Gly Glu Asn Gly Trp Thr Ala Ser Thr Gly
            740                 745                 750
Ile Glu Val Ile Glu Gly Asp Ala Val Phe Lys Gly Arg Tyr Leu His
            755                 760                 765
Leu Pro Gly Ala Arg Glu Ile Asp Thr Glu Thr Tyr Pro Thr Tyr Leu
    770                 775                 780
Tyr Gln Lys Val Glu Glu Gly Val Leu Lys Pro Tyr Thr Arg Tyr Arg
785                 790                 795                 800
Leu Arg Gly Phe Val Gly Ser Ser Gln Gly Leu Glu Ile Tyr Thr Ile
                805                 810                 815
Arg His Gln Thr Asn Arg Ile Val Lys Asn Val Pro Asp Asp Leu Leu
            820                 825                 830
Pro Asp Val Pro Pro Val Asn Asn Asp Gly Arg Ile Asn Arg Cys Ser
            835                 840                 845
Glu Gln Lys Tyr Val Asn Ser Arg Leu Glu Val Glu Asn Arg Ser Gly
    850                 855                 860
Glu Ala His Glu Phe Ser Ile Pro Ile Asp Thr Gly Glu Ile Asp Tyr
865                 870                 875                 880
Asn Glu Asn Ala Gly Ile Trp Val Gly Phe Lys Ile Thr Asp Pro Glu
                885                 890                 895
Gly Tyr Ala Thr Leu Gly Asn Leu Glu Leu Val Glu Glu Gly Pro Leu
            900                 905                 910
Ser Gly Asp Ala Leu Glu Arg Leu Gln Arg Glu Glu Gln Trp Lys
            915                 920                 925
Ile Gln Met Thr Lys Arg Arg Glu Glu Thr Asp Arg Lys Tyr Met Ile
    930                 935                 940
Ala Lys Gln Ala Val Asp Arg Leu Tyr Ala Asp Tyr Gln Asp Gln Gln
945                 950                 955                 960
Leu Asn Pro Asn Val Glu Ile Thr Asp Ile Thr Ala Ala Gln Asn Val
                965                 970                 975
Ile Gln Ser Ile Pro Tyr Val Tyr Asn Asp Ala Phe Pro Gly Leu Pro
            980                 985                 990
Gly Met Asn Tyr Thr Lys Phe Thr Glu Leu Thr Asp Arg Leu Gln Gln
            995                1000                1005
Ala Trp Ser Leu Tyr Asp Gln Arg Asn Ala Ile Pro Asn Gly Asp Phe
    1010                1015                1020
Arg Asn Glu Leu Ser Asn Trp Asn Thr Thr Ala Gly Val Asn Val Gln
1025                1030                1035                1040
Gln Leu Asn Gly Thr Ser Val Leu Val Ile Pro Asn Trp Asp Ala Gln
                1045                1050                1055
Val Ser Gln Gln Phe Thr Val Gln Pro Asn Gln Arg Tyr Val Leu Arg
            1060                1065                1070
```

Val Thr Ala Arg Lys Glu Gly Val Gly Asn Gly Tyr Val Ser Ile Arg
        1075                1080                1085

Asp Gly Gly Asn Gln Thr Glu Thr Leu Thr Phe Ser Ala Ser Asp Tyr
        1090                1095                1100

Asp Thr Asn Gly Val Tyr Asn Ile Gln Ala Ser Asn Thr Asn Gly Tyr
1105                1110                1115                1120

Asn Thr Asn Gly Val Tyr Asn Asp Gln Thr Gly Tyr Ile Thr Lys Thr
                1125                1130                1135

Ala Glu Phe Ile Pro His Thr Asn Gln Val Trp Ile Glu Met Ser Glu
                1140                1145                1150

Thr Glu Gly Thr Phe Tyr Ile Glu Ser Val Glu Leu Ile Val Asp Val
                1155                1160                1165

Glu

<210> SEQ ID NO 51
<211> LENGTH: 1212
<212> TYPE: PRT
<213> ORGANISM: Bacillus thuringiensis

<400> SEQUENCE: 51

Met Lys Asn Val Trp Lys Val Ile Leu Cys Asn Lys Cys Ile Gly Gly
1               5                   10                  15

Lys Arg Met Ser Pro Asn Gln Asn Glu Phe Asp Ile Ile Asp Val
            20                  25                  30

Pro Ser Asn Ile Ser Val Ser Asn Ser Phe Val Arg Tyr Pro Phe Ala
            35                  40                  45

Asn Asp Pro Asn Arg Thr Leu Gln Asn Thr Asn Tyr Lys Asp Phe Leu
50                  55                  60

Thr Met Ser Glu Lys Ser Asn Ser Gly Tyr Leu Thr Asp Pro Glu Ala
65                  70                  75                  80

Phe Asp Asp Val Gly Ser Ala Ile Phe Ala Gly Leu Ser Ile Thr Ala
                85                  90                  95

Lys Ile Met Asp Ala Phe Asp Val Pro Gly Gly Asp Ile Phe Asn Gly
            100                 105                 110

Leu Leu Glu Ile Ile Gly Ile Leu Trp Asp Leu Gln Asp Asp Thr Trp
        115                 120                 125

Glu Ala Phe Met Glu Gln Val Glu Val Leu Ile Asp Gln Lys Ile Ala
    130                 135                 140

Glu Tyr Ala Arg Asn Leu Ala Leu Thr His Leu Lys Gly Leu Glu Asn
145                 150                 155                 160

Ser Tyr Lys Leu Tyr Leu Glu Ala Leu Ala Asp Trp Lys Gln Asn Pro
                165                 170                 175

Thr Ser Pro Ser Ser Gln Glu Arg Val Arg Thr Arg Phe Arg Asp Thr
            180                 185                 190

Asp Asp Ser Leu Thr Val Phe Met Pro Ser Phe Ala Val Lys Gly Tyr
        195                 200                 205

Glu Val Pro Leu Leu Ala Val Tyr Ala Gln Ala Ala Asn Leu His Leu
    210                 215                 220

Leu Leu Leu Arg Asp Ser Val Ala Tyr Gly Leu Gly Trp Gly Leu Ser
225                 230                 235                 240

Gln Leu Asn Val Asn Asp Asn Tyr Asn Arg His Val Arg Leu Thr Gly
                245                 250                 255

Glu Tyr Thr Asn His Cys Val Ser Trp Tyr Thr Thr Gly Leu Glu Lys
            260                 265                 270

```
Leu Arg Gly Ser Asn Ala Gln Ser Trp Ile Lys Phe Asn Arg Tyr Arg
        275                 280                 285

Arg Glu Met Thr Val Met Val Leu Asp Ile Val Ala Leu Phe Pro Asn
    290                 295                 300

Tyr Asp Ala Arg Arg Tyr Pro Gln Ala Thr Thr Thr Glu Leu Thr Arg
305                 310                 315                 320

Leu Ile Tyr Thr Asp Pro His Gly Tyr Thr Ile Tyr Ser Pro Thr Ser
                325                 330                 335

Gln Thr Thr Ile Pro Trp Tyr Glu Tyr Gly Gln Ser Phe Ser Glu Ile
                    340                 345                 350

Glu Asn Val Ala Ile Gln Ala Pro Arg Leu Phe Arg Trp Ala Gln Glu
                355                 360                 365

Met Gln Ile Tyr Thr Lys Phe Val Arg His Ala Pro Gln Glu Ser His
    370                 375                 380

Tyr Trp Ala Ala His Thr Phe Ser Phe His His Thr Arg Asp Asn Thr
385                 390                 395                 400

Lys Thr Thr Leu Thr Tyr Gly Asp Thr Ser Asn Pro Ile Ser Val Gly
                405                 410                 415

Thr Ala Asp Leu Ser Asp Leu Asp Ile Tyr Lys Val Ser Ser Leu Val
                420                 425                 430

Ala Ser Ser Trp Gly Ser Gly Val Arg Leu Leu Val Thr Lys Ala Lys
                435                 440                 445

Phe Glu Val Ile Tyr Thr Phe Asn Gln Leu Trp Glu Phe Asn Tyr Glu
    450                 455                 460

Pro Pro Gly Ile Ser Asn Phe Phe Asn Gln Trp Lys Asn Thr Asp Thr
465                 470                 475                 480

Glu Leu Pro Ile Gln Ile Val Asp Pro Pro Thr Phe Gly Asp Pro Asn
                485                 490                 495

Gln Tyr Ser His Arg Val Ala Tyr Ile Ser His Ala Pro Ile Gln Pro
                500                 505                 510

Tyr Ser Gly Ala Phe Arg Asn Tyr Gly Leu Val Pro Val Phe Gly Trp
            515                 520                 525

Ser His Val Ser Val Asp Arg Asn Asn Thr Leu Tyr Ala Asp Arg Ile
    530                 535                 540

Thr Gln Ile Pro Ala Val Lys Ala Val Gln Leu Ser Gly Glu Pro Tyr
545                 550                 555                 560

Pro Val Val Arg Gly Pro Gly Phe Thr Gly Gly Asp Ile Ala Arg Leu
                565                 570                 575

Pro Asn Asn Pro Asn Val Gly Leu Leu Phe Asn Ser Lys Val Glu Ser
                580                 585                 590

Pro Ser Glu Asn Lys Arg Tyr Arg Val Arg Ile Arg Tyr Ala Cys Ala
                595                 600                 605

Ser Gly Ala Arg Ala Ile Phe Gly Gly Leu Tyr Leu Pro Ile Thr Val
610                 615                 620

Gln Phe Asn Gln Thr Met Ser Thr Thr Thr Pro Thr Arg Tyr Glu Asp
625                 630                 635                 640

Phe Gln Tyr Val Asp Val Ser Gly Thr Phe Ile Leu Gly Asn Thr Asn
                645                 650                 655

Val Ser Phe Ser Leu Val Pro Gln Ser Ala Asn Gln Thr Asn Asn Leu
                660                 665                 670

Phe Ile Asp Lys Ile Glu Phe Ile Pro Glu Asn Pro Ala Leu Glu Ala
                675                 680                 685

Glu Ser Asp Leu Glu Ala Ala Lys Lys Ala Val Asn Ala Leu Phe Thr
                690                 695                 700
```

```
Asn Ser Lys Asp Thr Leu Gln Ile Gly Val Thr Asp Tyr Gln Ile Asn
705                 710                 715                 720

Gln Ala Ala Asn Leu Ile Glu Cys Val Ser Asp Val Tyr Pro Asn
            725                 730                 735

Glu Lys Arg Leu Leu Phe Asp Ala Val Lys Glu Ala Lys Arg Leu Ser
                740                 745                 750

Thr Ala Arg Asn Leu Leu Glu Asp Thr Asp Phe His Thr Ile Asn Gly
            755                 760                 765

Gly Asn Gly Trp Thr Gly Ser Thr Gly Ile Glu Ile Val Glu Gly Asp
            770                 775                 780

Ile Leu Phe Lys Asp Arg Ser Leu Arg Leu Pro Ser Ala Arg Glu Ile
785                 790                 795                 800

Glu Arg Glu Thr Tyr Pro Thr Tyr Ile Tyr Gln Lys Ile Glu Glu Ser
                805                 810                 815

Arg Leu Lys Pro Asn Thr Arg Tyr Ser Leu Arg Gly Phe Ile Gly Ser
            820                 825                 830

Ser Gln Asp Leu Glu Ile Tyr Val Leu Arg His Gln Ala Tyr Arg Val
            835                 840                 845

Ile Lys Asn Val Ser Asp Asn Leu Leu Pro Asn Met Arg Pro Ile Asn
850                 855                 860

Ala Cys Gly Gly Val Asp Arg Cys Ser Gln Gln Lys Tyr Val Asn Asn
865                 870                 875                 880

Ser Leu Glu Val Asn Ser Gly Leu Ser Asn Gly Ile Gly Ala Ala Asp
            885                 890                 895

Ser His Glu Phe Ser Ile His Val Asp Thr Gly Glu Leu Asn Tyr Asn
            900                 905                 910

Glu Asp Met Gly Ile Trp Val Val Phe Lys Ile Thr Thr Thr Asp Gly
            915                 920                 925

Tyr Ala Thr Val Gly Asn Ile Glu Leu Val Glu Val Glu Thr Leu Ser
            930                 935                 940

Gly Glu Ala Leu Glu Arg Val Gln Arg Gln Glu Lys Gln Trp Gln Gly
945                 950                 955                 960

Gln Leu Ala Thr Arg Arg Lys Glu Thr Glu Thr Arg Tyr Gly Pro Ala
                965                 970                 975

Lys Gln Ala Ile Asp Arg Leu Phe Val Asp Phe Gln Asp Gln Gln Leu
            980                 985                 990

Ser Arg Ser Thr Glu Ile Ser Asp Leu Thr Glu Ala Gln Asn Leu Val
            995                 1000                1005

Gln Ser Ile Pro Tyr Val Tyr Asn Asp Met Leu Pro Glu Ile Pro Gly
    1010                1015                1020

Met Asn Tyr Thr Ser Val Thr Glu Leu Thr Asn Arg Leu Gln Gln Ala
1025                1030                1035                1040

Trp Asn Leu Tyr Asp Gln Arg Asn Ser Ile Gln Asn Gly Asp Phe Arg
                1045                1050                1055

Asn Asp Val Ser Asn Trp Asn Val Thr Thr Glu Val Asn Ile Gln Gln
                1060                1065                1070

Met Asn Asp Thr Ser Val Leu Val Ile Pro Asn Trp Asp Ser Gln Val
            1075                1080                1085

Ser Gln Gln Ile Thr Val Gln Pro Asn Arg Arg Tyr Val Leu Arg Val
            1090                1095                1100

Thr Ala Arg Lys Glu Gly Asn Gly Asp Gly Tyr Val Thr Ile Arg Asp
1105                1110                1115                1120

Gly Ala Asn His Thr Glu Thr Leu Thr Phe Asn Thr Cys Asp Tyr Asp
```

```
                1125                1130                1135

Gly Asn Ser Val Tyr Asn Asn Gln Pro Leu Asn Ala Asn Asn Asn Val
            1140                1145                1150

Tyr Thr Thr Lys Ser Ser Asn Thr Asn Ser Tyr His Thr Asn Gly Val
        1155                1160                1165

Tyr His Asp Gln Thr Ser Tyr Val Thr Lys Thr Met Glu Phe Thr Pro
    1170                1175                1180

Tyr Thr Glu Gln Val Trp Val Glu Met Ser Glu Thr Glu Gly Val Phe
1185                1190                1195                1200

Tyr Ile Asp Ser Val Glu Leu Ile Val Glu Glu Met
                1205                1210

<210> SEQ ID NO 52
<211> LENGTH: 1231
<212> TYPE: PRT
<213> ORGANISM: Bacillus thuringiensis

<400> SEQUENCE: 52

Met Val Met Ser Ser Val Ser Ile Gly Gly Lys Lys Met Ser Gln Asn
 1               5                  10                  15

Asn Gln Asn Glu Tyr Asp Ile Ile Asp Val Ser Ser Gly Asn Phe Ile
            20                  25                  30

Ser Asn Asp Ser Val Arg Tyr Pro Leu Ala Asn Asn Pro Asn His Thr
        35                  40                  45

Leu Gln Asn Ile Asn Tyr Lys Asp Tyr Leu Asn Met Ser Glu Gly Asn
    50                  55                  60

Ser Val Glu Leu Phe Gly Asp Ser Gln Ala Phe Asn Arg Val Ala Thr
65                  70                  75                  80

Ala Gln Thr Gly Leu Ala Ile Val Gly Gly Ala Leu Gly Ala Leu Gly
                85                  90                  95

Val Pro Phe Ala Gly Glu Ile Ala Gly Leu Phe Ser Phe Ile Leu Asp
            100                 105                 110

Leu Phe Trp Pro Ser Gln Glu Thr Asp Val Trp Glu Met Ile Met Asp
        115                 120                 125

Gln Val Gln Gly Leu Ile Asp Gln Ser Ile Thr Ala Asn Val Arg Ser
    130                 135                 140

Gln Ala Ile Ala Lys Leu Glu Gly Leu Gly Arg Gly Leu Glu Ala Tyr
145                 150                 155                 160

Gln Glu Leu Leu Val Ala Trp Leu Glu Asn Arg Asn Asn Ala Arg Thr
                165                 170                 175

Arg Ser Leu Ile Lys Gln Gln Tyr Val Ala Leu Glu Gln Ile Phe Thr
            180                 185                 190

Thr Gly Leu Pro Glu Phe Ser Val Gln Asn Gln Glu Val Pro Leu Leu
        195                 200                 205

Gly Val Tyr Ala Gln Ala Ala Asn Leu His Leu Leu Leu Leu Arg Asp
    210                 215                 220

Val Ser Ile Phe Gly Ala Glu Trp Gly Phe Glu Asp Tyr Glu Ile Asp
225                 230                 235                 240

Val Phe Tyr Asn Arg Gln Met Arg Tyr Thr Ala Glu Tyr Ala Asn Tyr
                245                 250                 255

Cys Val Glu Trp Tyr Asn Lys Gly Leu Asp Arg Leu Lys Gly Thr Asp
            260                 265                 270

Arg Ile Ser Trp Met Lys Tyr His Gln Phe Arg Arg Glu Met Thr Leu
        275                 280                 285

Leu Val Leu Asp Ile Val Ala Leu Phe Pro Asn Tyr Asp Ala Arg Arg
```

```
                290                 295                 300
Tyr Pro Leu Glu Thr Glu Ala Gln Leu Thr Arg Glu Val Tyr Thr Asp
305                 310                 315                 320

Pro Ile Val Tyr Asn Pro Glu Glu Phe Leu Gly Gly Phe Cys Asn Ser
                325                 330                 335

Trp Thr Ser Asp Asn Gln Ser Asp Phe Ser Gln Ile Glu Asn Ala Val
                340                 345                 350

Ile Arg Pro Pro His Val Phe Asp Thr Ile Ala Ser Leu Glu Ile Asn
                355                 360                 365

Thr Ala Arg Gly Arg Ile Ala Leu Asn Asn Thr Ala Tyr Ile Asp Phe
370                 375                 380

Trp Ala Gly His Ser Leu Thr Phe Arg Tyr Pro Asn Asp Ser Ala Arg
385                 390                 395                 400

His Gln Val Gln Tyr Gly Thr Ile Thr Ser Glu Lys Asn Ser Phe Pro
                405                 410                 415

Phe Glu Val Thr Asp Val Val Gln Val Asn Thr Thr Ala Ala Asn Leu
                420                 425                 430

Ala Asn Ala Tyr Gln Gln Ala Tyr Gly Ala Pro Arg Ala Val Phe Gln
            435                 440                 445

Leu Val Asn Arg Leu Asn Gly Ala Val Gly Ser Leu Thr Tyr Ser Lys
450                 455                 460

Thr His Thr Ala Ile Gln Ala Cys Thr Gln Ser Leu Asn Thr Asn Ser
465                 470                 475                 480

Glu Ile Pro Arg Leu Pro Val Ser Pro Gly Val Thr Asn Leu Ser Thr
                485                 490                 495

Leu Tyr Thr His Arg Ile Ser His Ile Thr Ser Tyr Asn Phe Ser Asn
            500                 505                 510

Asn Leu Ala Gly Asn Arg Asn Arg Tyr Gly Asn Phe Pro Val Phe Val
            515                 520                 525

Trp Thr His Arg Ser Ala Glu Ile Asp Asn Lys Ile Tyr Ala Asn Lys
            530                 535                 540

Ile Thr Gln Ile Pro Ala Val Lys Ala Leu Trp Ala Ser Ser Glu Pro
545                 550                 555                 560

Tyr Pro Val Val Arg Gly Pro Gly Phe Thr Gly Gly Asp Ile Ala Arg
                565                 570                 575

Leu Pro Asn Asn Pro Asn Ile Gly Leu Arg Phe Leu Leu Asp Pro Glu
                580                 585                 590

Pro Gly Val Leu Phe Asn Arg Arg Phe Arg Val Arg Ile Arg Phe Ala
                595                 600                 605

Cys Asp Ser Gly Ala Arg Val Ile Leu Thr Asp Glu Thr Gly Ile Asn
610                 615                 620

Ser Glu Thr Ile Val Leu Asn Gln Thr Met Thr Thr Glu Asn Pro Arg
625                 630                 635                 640

Lys Tyr Asp Asp Phe Gln Tyr Ile Glu Ser Arg Asn Val Tyr Thr Leu
                645                 650                 655

Thr Arg Phe Pro Gly Pro Trp Ile Trp Arg Leu Gly Ala Gln Ser Ala
                660                 665                 670

Asp Gln Thr Arg Asn Val Tyr Ile Asp Arg Ile Glu Phe Ile Pro Leu
            675                 680                 685

Asn Pro Ala Leu Glu Ala Glu Asn Asp Leu Glu Thr Ala Lys Lys Ala
                690                 695                 700

Val Asn Ala Leu Phe Thr Asn Arg Lys Asp Thr Leu Gln Ile Ser Val
705                 710                 715                 720
```

```
Thr Asp Tyr Gln Ile Asn Gln Ala Ala Asn Leu Ile Glu Cys Val Ser
            725                 730                 735

Asp Glu Val Tyr Pro Asn Glu Lys Arg Leu Leu Phe Asp Ala Val Lys
            740                 745                 750

Glu Ala Lys Arg Leu Ser Thr Ala Arg Asn Leu Leu Glu Asp Thr Asp
            755                 760                 765

Phe His Ala Ile Asn Gly Gly Asn Gly Trp Thr Gly Ser Thr Gly Ile
            770                 775                 780

Glu Ile Val Glu Gly Asp Leu Leu Phe Lys Asp Arg Ser Leu Arg Leu
785                 790                 795                 800

Pro Ser Ala Arg Glu Ile Glu Arg Glu Thr Tyr Pro Thr Tyr Ile Tyr
            805                 810                 815

Gln Lys Ile Glu Glu Ser Arg Leu Lys Pro Asn Thr Arg Tyr Ser Leu
            820                 825                 830

Arg Gly Phe Ile Gly Ser Ser Gln Asp Leu Glu Ile Tyr Val Leu Arg
            835                 840                 845

His Gln Ala Tyr Arg Val Ile Lys Asn Val Ser Asp Asn Leu Leu Pro
            850                 855                 860

Asn Met Arg Pro Ile Asn Ala Cys Gly Gly Val Asp Arg Cys Ser Gln
865                 870                 875                 880

Gln Lys Tyr Val Asn Asn Ser Leu Glu Leu Asn Ser Ser Leu Ser Asn
            885                 890                 895

Gly Ile Gly Ala Ala Asp Ser His Glu Phe Ser Ile His Met Asp Thr
            900                 905                 910

Gly Glu Leu Asn Tyr Asn Glu Asp Thr Gly Ile Trp Val Val Phe Lys
            915                 920                 925

Ile Thr Thr Thr Asp Gly Tyr Ala Thr Leu Gly Asn Leu Glu Leu Val
            930                 935                 940

Glu Glu Gly Pro Leu Ser Gly Asp Thr Leu Glu Arg Val Arg Lys Gln
945                 950                 955                 960

Glu Lys Gln Trp Gln Asp Gln Met Ala Arg Arg Ala Glu Thr Glu
            965                 970                 975

Thr Arg Tyr Gly Ala Ala Lys Gln Ala Ile Asp Arg Leu Phe Ile Asp
            980                 985                 990

Tyr Gln Asp Gln Gln Leu Ser Pro Gly Thr Asp Ile Ser Asp Leu Thr
            995                 1000                1005

Ala Ala Gln Asn Val Val Gln Ser Ile Pro Tyr Val Tyr Asn Asp Met
            1010                1015                1020

Leu Pro Glu Ile Pro Gly Met Asn Tyr Thr Ser Val Thr Glu Leu Thr
1025                1030                1035                1040

Asn Arg Leu Gln Gln Ala Trp Asp Leu Tyr Asp Gln Arg Asn Ser Ile
            1045                1050                1055

Pro Asn Gly Asp Phe Arg Tyr Gly Leu Asn Asp Trp Asn Ala Lys Ser
            1060                1065                1070

Gly Ala Asn Val Gln Gln Val Asn His Thr Ser Val Leu Val Ile Pro
            1075                1080                1085

Asn Trp Asp Ser Gln Ala Ser Gln Glu Ile Thr Val Gln Pro Asn Arg
            1090                1095                1100

Arg Tyr Val Leu Arg Val Thr Ala Arg Lys Glu Gly Ser Gly Asp Gly
1105                1110                1115                1120

Tyr Val Thr Ile Arg Asp Gly Ala Lys Tyr Thr Glu Thr Leu Thr Phe
            1125                1130                1135

Asn Thr Cys Asp Tyr Asn Gly Ser Asn Val Tyr Gln Glu Gln Ala Leu
            1140                1145                1150
```

```
Tyr Thr Asn Asp Val Tyr Asn Thr Gln Ser Ala Asn Ile Gln Gly Ser
            1155                1160                1165

Asn Ser Ala Tyr His Thr Gln Ala Ser Asn Thr Asp Arg Tyr Asn Met
        1170                1175                1180

Asn Gly Met Tyr Asn Asp Gln Thr Ser Tyr Val Thr Lys Thr Val Glu
1185                1190                1195                1200

Phe Ile Pro His Thr Glu Gln Val Trp Ile Glu Met Ser Glu Thr Glu
                1205                1210                1215

Gly Val Phe Tyr Ile Glu Ser Val Glu Leu Ile Val Lys Glu Asn
            1220                1225                1230

<210> SEQ ID NO 53
<211> LENGTH: 1168
<212> TYPE: PRT
<213> ORGANISM: Bacillus thuringiensis

<400> SEQUENCE: 53

Met Thr Leu Asn Asn Glu Tyr Glu Ile Ile Asp Thr Pro Ser Arg
1               5                   10                  15

Thr Ser Val Ser Asn Glu Ser Phe Arg Tyr Pro Leu Ala Ser Asn Gln
            20                  25                  30

Ser Thr Ser Leu Gln Asn Arg Asn Tyr Lys Asp Trp Leu Asn Thr Leu
        35                  40                  45

Glu Gly Gly Asn Asn Gln Gly Phe Ile Asn Ile Glu Gly Arg Leu Ser
    50                  55                  60

Leu Glu Gln Val Leu Ala Val Ser Ala Gly Val Ala Ser Tyr Ile Leu
65                  70                  75                  80

Ser Asn Leu Gly Pro Phe Gly Val Phe Phe Ser Tyr Ile Ile Gly Ala
                85                  90                  95

Phe Trp Pro Thr Ala Pro Ser Asp Thr Arg Val Trp Glu Ala Phe Met
            100                 105                 110

Glu Leu Ile Glu Ala Arg Ile Asp Gln Lys Ile Gln Glu Ser Thr Arg
        115                 120                 125

Lys Asp Ala Ile Ala Arg Leu Gln Gly Leu Gly Ala Ala Ser Glu Val
    130                 135                 140

Tyr Gln Glu Ser Leu Glu Ser Trp Leu Glu Asn Gln Asn Asp Ala Arg
145                 150                 155                 160

Ala Met Ser Val Val Arg Gln Gln Phe Val Ala Phe Glu Leu Asp Phe
                165                 170                 175

Val Thr Ala Met Pro Phe Phe Glu Arg Ser Gly Asp Glu Ile Leu Leu
            180                 185                 190

Leu Ala Val Tyr Ala Gln Ala Ala Asn Leu His Leu Leu Leu Leu Arg
        195                 200                 205

Asp Ala Ser Leu Tyr Gly Ala Asp Trp Gly Met Glu Pro Tyr Asp Ile
    210                 215                 220

Ala Asn Tyr Tyr Asn Arg Gln Lys Glu Arg Thr Ala Thr Tyr Ser Asn
225                 230                 235                 240

His Cys Met Glu Trp Tyr Lys Lys Gly Leu Asp Glu Leu Trp Ser Ala
                245                 250                 255

Gly Gly Tyr Gly Gly Asp Val Trp Gln Asp Tyr Asn Asp Phe Arg Arg
            260                 265                 270

Glu Met Thr Leu Ser Val Leu Asp Phe Val Ala Leu Phe Pro Asn Tyr
        275                 280                 285

Asp Thr His Leu Tyr Pro Ile Glu Val Lys Gly Glu Leu Thr Arg Glu
    290                 295                 300
```

```
Ile Tyr Thr Pro Gly Ile Asn Ile Asp Ile Asp Arg Gly Arg Leu Gly
305                 310                 315                 320

Lys Val Thr Leu Glu Asn Ala Leu Val Asn Ser Pro Arg Leu Phe Ser
                325                 330                 335

Trp Leu Lys Glu Ile Gln Leu Phe Thr Asn Ile Asn Phe Asn Pro Arg
            340                 345                 350

Trp Lys Phe Leu Ser Ala Thr Arg Ile Gly Tyr Lys Leu Thr Gly Tyr
        355                 360                 365

Arg Ser Val Asn Phe Glu Pro Tyr Glu Gly Phe Tyr Phe Glu Gly Leu
    370                 375                 380

Phe Gln Ser Asn Phe Thr Leu Asn Asp Tyr Gln Glu Ile Tyr Ile Val
385                 390                 395                 400

Asp Val Thr Arg Phe Gly Ser Leu Tyr Asp Thr Pro Thr Ala Ile Thr
                405                 410                 415

Ala Met Thr Phe Phe Lys Asp Asp Asn Thr Thr Phe Asn Tyr Ser Ser
            420                 425                 430

Asn Thr Pro Ser Gly Glu Pro Met Ile Thr Ser Gly Phe Tyr Leu Pro
        435                 440                 445

Gly Ile Asp Gly Ser Glu Glu Pro Thr Ser Asn Asn Phe Ser His Arg
    450                 455                 460

Leu Ser Thr Ile Asn Thr Tyr Asn Thr Thr Asn Gln Thr Phe Tyr His
465                 470                 475                 480

Thr Phe Gly Trp Thr His Val Ser Val Asp Arg Asn Asn Thr Ile Val
                485                 490                 495

Ser Asn Lys Ile Thr Gln Ile Pro Phe Val Lys Ala Asn Thr Gly Asn
            500                 505                 510

Val Val Arg Gly Pro Gly His Thr Gly Gly Asp Leu Val Val Phe Lys
        515                 520                 525

Pro Ala Ala Arg Pro Asp Ile Val Leu Arg Val Gly Asn Thr Arg Leu
    530                 535                 540

Gln Ser Tyr Arg Val Arg Val Arg Tyr Ala Ser Asn Ala Asp Ile Ser
545                 550                 555                 560

Leu Glu Leu Asp Thr Thr Tyr Glu Lys Thr Asn Ile His Leu Gln Lys
                565                 570                 575

Thr Phe Asn Ser Ser Glu Ala Glu Asp Leu Thr Tyr Asn Phe Gln
            580                 585                 590

Tyr Ala Glu Ala Asp Asn Ile Val Trp Leu Gly Gln Asp Leu Ser Gln
        595                 600                 605

Tyr Ile Glu Phe Gln Asn Ala Ile Thr Asn Asp Ser Thr Ala Ile Ala
    610                 615                 620

Tyr Phe Glu Arg Val Glu Phe Leu Pro Val Gly Ala Thr Tyr Glu Ala
625                 630                 635                 640

Glu Gln Asp Leu Glu Thr Ala Lys Lys Val Val Asn Ala Leu Phe Thr
                645                 650                 655

Asn Thr Lys Asn Ala Leu Gln Met Ser Val Thr Asp Tyr Glu Val Thr
            660                 665                 670

Gln Ala Ala Asn Leu Val Glu Cys Val Ser Asp Glu Leu Phe Pro Asn
        675                 680                 685

Glu Lys Arg Leu Leu Phe Asp Ala Val Lys Glu Ala Lys Arg Leu Ser
    690                 695                 700

Gly Ile Arg Asn Leu Leu Gln Asp Ser Asp Phe Gln Glu Ile Asn Gly
705                 710                 715                 720

Glu Asn Gly Trp Val Gly Ser Ile Glu Ile Glu Ile Arg Glu Gly Asp
```

```
                725                 730                 735
Thr Leu Phe Lys Gly Tyr Ser Leu Arg Leu Pro Ser Ala Arg Glu Ile
            740                 745                 750

Tyr Met Glu Met Phe Pro Thr Tyr Leu His Gln Lys Ile Glu Glu Ser
            755                 760                 765

Arg Leu Lys Pro Tyr Thr Arg Tyr Arg Leu Arg Gly Phe Val Ser Ser
            770                 775                 780

Ser Gln Asp Leu Glu Ile Phe Ser Ile Arg His Glu Thr Asn Arg Ile
785                 790                 795                 800

Val Lys Asn Val Ser Asp Asp Leu Leu Pro Asn Leu Ser Ser Tyr Tyr
                805                 810                 815

Thr Cys Gly Gly Val Asn Arg Cys Ser Thr Gln Lys Tyr Val Tyr Asn
                820                 825                 830

Arg Leu Glu Phe Gln Asn Ser Leu Ser Ser Gly Asn Arg Tyr Ser Asp
                835                 840                 845

Ala His Ser Phe Ser Ile Pro Ile Asp Thr Gly Lys Ile Asp Leu Asn
            850                 855                 860

Asp Asn Thr Gly Ile Trp Ile Ala Phe Lys Leu Ala Thr Thr Gly Gly
865                 870                 875                 880

Tyr Ala Thr Leu Gly Asn Leu Glu Leu Val Glu Glu Ala Pro Leu Ile
                885                 890                 895

Gly Asp Thr Leu Glu Arg Val Gln Arg Glu Asp Gln Gln Trp Lys Ser
                900                 905                 910

Gln Met Thr Arg Lys Arg Glu Glu Ala Glu Arg Lys Tyr Met Ala Ala
            915                 920                 925

Lys Gln Ala Ile Asp Arg Leu Tyr Ala Asp Tyr Gln Asp Gln Gln Leu
            930                 935                 940

Asn Pro Asn Val Glu Ile Thr Asp Ile Thr Ala Thr Gln His Leu Val
945                 950                 955                 960

Gln Ser Leu Pro Tyr Val Asn Asn Asp Val Leu Gln Glu Ile Pro Gly
                965                 970                 975

Met Asn Tyr Thr Arg Phe Thr Glu Leu Thr Asn Arg Leu Gln Gln Ala
            980                 985                 990

Trp Glu Leu Tyr Gly Leu Arg Asn Met Ile Ala Asn Gly Asp Phe Arg
            995                 1000                1005

Asn Gly Leu Asn Asp Trp Asp Ala Thr Ser Gly Val Asn Ile Gln Gln
                1010                1015                1020

Ile Asn His Thr Ser Val Leu Val Ile Ser Asn Trp Asp Ala Gln Ile
1025                1030                1035                1040

Ser Lys Gln Phe Thr Val Gln Pro Asn Gln Lys Tyr Val Leu Arg Val
                1045                1050                1055

Thr Val Arg Lys Glu Gly Ser Gly Asp Gly Tyr Val Thr Ile Arg Asp
                1060                1065                1070

Gly Gly Asn His Thr Glu Thr Leu Thr Phe Asn Thr Cys Asp Tyr Glu
                1075                1080                1085

Arg Ser Asn Val Tyr Asn Glu Lys Val Phe Gln Ser Asn Asp Tyr Gly
                1090                1095                1100

Thr Asn Asn Val Tyr His Thr Gln Thr Thr Asn Ala Asn Arg Tyr Thr
1105                1110                1115                1120

Thr Asn Ser Leu Tyr Asn Asp Gly Thr Gly Tyr Val Thr Lys Thr Val
                1125                1130                1135

Glu Phe Ile Pro Tyr Thr Glu Gln Val Trp Ile Glu Met Ser Glu Thr
                1140                1145                1150
```

-continued

Glu Gly Val Phe Tyr Val Glu Ser Ile Glu Phe Ile Leu Glu Glu Val
            1155                1160                1165

<210> SEQ ID NO 54
<211> LENGTH: 1204
<212> TYPE: PRT
<213> ORGANISM: Bacillus thuringiensis

<400> SEQUENCE: 54

Met Asn Ile Gln Asn Ser Asn Asp Ala Asn Thr Asn Arg Ile Leu Asn
  1               5                  10                  15

Asn Gly Leu Ser Val Ser Ser Thr Ala Asn Leu Leu Glu Leu Val Gln
                 20                  25                  30

Gln Gly Arg Ser Asp Tyr Ala Gly Lys Cys Tyr Ser Gly Tyr Ile Asp
             35                  40                  45

Leu Ile Gly Glu Pro Arg Ser Thr Pro Ile Ser Asn Arg Phe Ser Asn
 50                  55                  60

Ser Ile Leu Pro Asn Thr Ile Thr Asn Asp Pro Arg Ile Val Glu Thr
 65                  70                  75                  80

Cys Gly Asn Gly Ser Ile Val Asp Asn Thr Val Gln Asp Ser Ile Thr
                 85                  90                  95

Thr Val Ile Asp Ile Thr Asn Ile Ile Leu Asp Leu Phe Asn Val Pro
                100                 105                 110

Ile Val Gly Pro Val Leu Ser Ile Val Asn Arg Leu Ile Asn Arg Leu
            115                 120                 125

Trp Pro Ser Asn Tyr Gly Thr Ala Ile Trp Glu Ala Leu Met Ala Glu
130                 135                 140

Val Glu Lys Ile Val Asp Lys Lys Ile Asp Glu Ala Val Lys Ser Lys
145                 150                 155                 160

Ala Leu Ser Glu Leu Glu Gly Leu Gln Arg Ile Tyr Ser Ser Tyr Gln
                165                 170                 175

Ser Asp Leu Glu Arg Trp Leu Gly Asp Arg Asp Asn Pro Glu Tyr Gln
            180                 185                 190

Glu Ile Ile Arg Gln Gln Phe Asn Val Val Asn Asn Phe Phe Ala Tyr
         195                 200                 205

Gln Met Pro Ser Phe Ala Val Ser Gly Phe Glu Ile Leu Leu Leu Ser
210                 215                 220

Val Tyr Thr Gln Ala Ala Asn Leu His Leu Asn Leu Leu Arg Asp Ile
225                 230                 235                 240

Thr Val His Gly Thr Gly Trp Gly Tyr Ser Glu Gly Thr Val Glu Arg
                245                 250                 255

Tyr Asn Gln Leu Gln Arg Cys Leu Ile Thr Ala Tyr Val Asp Tyr Cys
            260                 265                 270

Val Asp Gln Tyr Asn Leu Glu Leu Glu Lys Leu Pro Lys Glu Thr Leu
        275                 280                 285

Lys Asn Trp Val Asp Tyr Asn Arg Tyr Arg Arg Glu Met Thr Leu Ser
290                 295                 300

Val Leu Asp Ile Val Ser Leu Phe Pro Asn Tyr Asp Ala Ser Val Tyr
305                 310                 315                 320

Asp Leu Pro Ile Asn Ala Glu Leu Ser Arg Gln Val Tyr Thr Asp Pro
                325                 330                 335

Leu Gly Ser Tyr Leu Pro Tyr Asn Thr Ala Asn Pro Ile Ser Trp Tyr
            340                 345                 350

Asp Met Lys Ser Tyr Ile His Pro Asn Phe Trp Gln Ile Asp Lys Tyr
        355                 360                 365

-continued

```
Phe Ile Lys Pro Pro Asn Leu Phe Thr Phe Ala Glu Lys Leu Ile Met
        370                 375                 380

Tyr Ser Gly Tyr Arg Thr Asp Val Asp Pro Ile Phe Tyr Tyr Tyr Trp
385                 390                 395                 400

Ser Gly Ser Lys Leu Glu Ser Arg Arg Val His Gly Asn Glu Ile Ile
                405                 410                 415

Thr Thr Ile Ser Gly Asp Ile Ser Gln Ser Ile Thr Leu Val Asn Val
            420                 425                 430

Asp Phe Lys Asp Ser Asp Ile Tyr Lys Ile Thr Thr Asn Tyr Ile Gly
        435                 440                 445

Gln Tyr Thr Gly Ser Leu Leu Gly Thr Asn Pro Ile Thr Phe Ser Leu
    450                 455                 460

Thr Asn Ser Asn Gly Gln Thr Glu Arg Lys Tyr Glu Tyr Ser Lys Leu
465                 470                 475                 480

Leu Met Pro Gly Lys Glu Lys Ile Tyr Tyr Ser Gln Asp Glu Ile Pro
                485                 490                 495

Pro Asn Ile Glu Thr Gly Glu Pro Asp Tyr Val Ala Tyr Ser His Arg
            500                 505                 510

Leu Ser Tyr Val Ser Ala Phe Asn Pro Asn Phe Thr Ser Gly Lys Lys
        515                 520                 525

Ile Gly Thr Val Pro Ile Tyr Gly Trp Thr His Thr Ser Val Ser Arg
    530                 535                 540

Asp Asn Leu Ile Tyr Pro Asp Lys Ile Thr Gln Ile Pro Ile Val Lys
545                 550                 555                 560

Ser Tyr Glu Ile Gly Tyr Tyr Lys Val Met Gln Gly Pro Gly Phe
                565                 570                 575

Thr Gly Gly Asp Ile Leu Thr Lys Thr Tyr Pro Val Gln Asn Pro Ser
            580                 585                 590

Gly Ser Thr Leu Ala Ala Arg Ile Arg Val Ser Thr Ala Gly Ile His
        595                 600                 605

Leu Asn Gln Arg Tyr Thr Leu Arg Met His Tyr Ala Ala Ser Gly Ser
    610                 615                 620

Val Tyr Asp Ala Met Ile Ile Lys Pro Gly Gln Ser Glu Gly Gly Tyr
625                 630                 635                 640

His Met Arg Leu Asn Pro Thr Met Glu Asn Gly Glu Thr Leu Thr Phe
                645                 650                 655

Asn Ser Phe Thr Ser Ile Gly Met Asn Ser Gln Val Leu Thr Ser Ser
            660                 665                 670

Gln Thr Asp Leu Thr Leu Tyr Ile Lys Ser Met Ser Pro Ser Thr Pro
        675                 680                 685

Gly Thr Ile Tyr Ile Asp Arg Ile Glu Phe Ile Pro Val Asp Asn Asn
    690                 695                 700

Tyr Glu Ala Glu Gln Asn Leu Glu Lys Ala Gln Lys Ala Val Asn Ala
705                 710                 715                 720

Leu Phe Thr Ala Gly Arg Asn Ala Leu Gln Thr Asp Val Thr Asp Tyr
                725                 730                 735

Lys Val Asp Gln Val Ser Ile Val Val Asp Cys Val Ser Lys Glu Val
            740                 745                 750

Tyr Pro Asn Glu Lys Arg Glu Leu Gln Asn Leu Val Lys Tyr Ala Lys
        755                 760                 765

Arg Leu Thr Asn Ser Arg Asn Leu Leu Val Asp Pro Asn Phe Thr Ser
    770                 775                 780

Ile Asn Ser Glu Gly Val Asn Gly Trp Tyr Gly Ser Asn Gly Ile Val
785                 790                 795                 800
```

Ile Gly His Gly Asp Asp Val Phe Lys Gly Asn Tyr Ile Gln Leu Ala
            805                 810                 815

Gly Thr Asn Asp Ala Gln Tyr Pro Thr Tyr Leu Tyr Gln Lys Ile Asp
            820                 825                 830

Glu Ser Lys Leu Lys Glu Tyr Thr Arg Tyr Lys Leu Arg Gly Phe Ile
            835                 840                 845

Lys Ser Ser Gln Asp Leu Glu Ala Tyr Val Ile Arg Tyr Asp Ala Lys
        850                 855                 860

His Glu Thr Leu Asp Val Ser Asn Asn Leu Phe Pro Asp Ile Ser Pro
865                 870                 875                 880

Val Asn Ala Cys Gly Glu Pro Asn Arg Cys Gly Ala Leu Gln Tyr Leu
                885                 890                 895

Asp Glu Asn Pro Arg Leu Glu Cys Ser Ser Ile Gln Asp Gly Ile Leu
            900                 905                 910

Ser Asp Ser His Ser Phe Ser Leu Asn Ile Asp Thr Gly Ser Ile Asp
            915                 920                 925

Phe Asn Glu Asn Val Gly Ile Trp Val Leu Phe Lys Ile Ser Thr Pro
        930                 935                 940

Glu Gly Tyr Ala Arg Phe Gly Asn Leu Glu Val Ile Glu Asp Asp Thr
945                 950                 955                 960

Val Ile Gly Glu Ala Leu Ala Arg Val Lys Arg Gln Glu Thr Lys Trp
                965                 970                 975

Arg Asn Lys Leu Thr Gln Leu Arg Thr Glu Thr Gln Ala Ile Tyr Thr
            980                 985                 990

Arg Ala Lys Gln Ala Ile Asp Asn Leu Phe Thr Asn Ala Gln Asp Ser
        995                 1000                1005

His Leu Lys Ile Gly Ala Thr Phe Ala Ser Ile Val Ala Ala Arg Lys
    1010                1015                1020

Ile Val Gln Ser Ile Arg Glu Ala Tyr Met Pro Trp Leu Ser Ile Val
1025                1030                1035                1040

Pro Gly Val Asn Tyr Pro Ile Phe Thr Glu Leu Asn Glu Arg Val Gln
            1045                1050                1055

Arg Ala Phe Gln Leu Tyr Asp Val Arg Asn Val Val Arg Asn Gly Arg
            1060                1065                1070

Phe Leu Ser Gly Val Ser Asp Trp Ile Val Thr Ser Asp Val Lys Val
        1075                1080                1085

Gln Glu Glu Asn Gly Asn Asn Val Leu Val Leu Ser Asn Trp Asp Ala
1090                1095                1100

Gln Val Leu Gln Cys Leu Lys Leu Tyr Gln Asp His Gly Tyr Ile Leu
1105                1110                1115                1120

Arg Val Thr Ala Arg Lys Glu Gly Leu Gly Glu Gly Tyr Ile Thr Ile
            1125                1130                1135

Thr Asp Glu Glu Gly His Thr Asp Gln Leu Thr Phe Gly Thr Cys Glu
            1140                1145                1150

Glu Ile Asp Ala Ser Asn Met Phe Val Thr Thr Gly Tyr Met Thr Lys
        1155                1160                1165

Glu Leu Glu Phe Phe Pro Asn Thr Glu Lys Val Arg Ile Glu Ile Gly
    1170                1175                1180

Glu Thr Glu Gly Thr Phe Gln Val Glu Ser Ile Glu Leu Phe Leu Met
1185                1190                1195                1200

Glu Asp Leu Cys

<210> SEQ ID NO 55

```
<211> LENGTH: 1131
<212> TYPE: PRT
<213> ORGANISM: Bacillus thuringiensis

<400> SEQUENCE: 55

Met Asn Gln Lys Asn Tyr Asp Ile Met Gly Ala Ser Thr Asn Ala Thr
  1               5                  10                  15

Ala Glu Leu Thr Glu Asn Tyr Asn Thr Ile Ile Ser Pro Tyr Gly Ala
             20                  25                  30

Pro Thr Ser Val Thr Thr Ile Glu Ile Thr Gly Thr Ile Leu Ser
         35                  40                  45

Asp Leu Gly Val Pro Gly Ala Ser Ser Ile Ser Leu Leu Leu Asn Lys
 50                  55                  60

Leu Leu Ser Ile Leu Trp Pro Asp Asp Thr Asn Thr Met Trp Gly Thr
 65                  70                  75                  80

Phe Ala Lys Glu Thr Ala Tyr Leu Leu Asn Glu Val Leu Ser Pro Asn
                 85                  90                  95

Asp Pro Val Val Ile Asp Ala Asp Asn Lys Leu Glu Gly Leu Lys Asn
            100                 105                 110

Thr Leu Asp Leu Tyr Leu Glu Ala Leu Lys Glu Trp Lys Asn Asp Pro
        115                 120                 125

Gln Asn Pro Ala Ser Gln Glu Arg Val Arg Thr Arg Phe Arg Asn Val
130                 135                 140

Asp Asp Asp Phe Thr His Asp Met Pro Ser Phe Ala Arg Ala Gly Tyr
145                 150                 155                 160

Glu Thr Lys Leu Leu Thr Val Tyr Ala Gln Ala Ala Asn Leu His Leu
                165                 170                 175

Leu Leu Leu Arg Asp Ala Ser Met Phe Gly Glu Gly Trp Gly Met Thr
            180                 185                 190

Gln Val Asn Ile Asn Asp Asn Tyr Asn Arg Gln Leu Arg Leu Thr Ala
        195                 200                 205

Gln Tyr Thr Asp His Ser Val Lys Trp Tyr Asn Ala Gly Leu Glu Lys
    210                 215                 220

Leu Lys Gly Lys Leu Thr Gly Glu Asn Trp Tyr Thr Tyr Asn Arg Phe
225                 230                 235                 240

Arg Arg Glu Met Thr Leu Met Val Leu Asp Val Val Ala Leu Phe Pro
                245                 250                 255

Asn Tyr Asp Thr Arg Met Tyr Pro Ile Ala Thr Thr Ser Glu Leu Thr
            260                 265                 270

Arg Ile Ile Tyr Thr Asp Pro Ile Ala Tyr Thr Gln Asp His Pro Trp
        275                 280                 285

Tyr Lys Ile Thr Ser Leu Ser Phe Ser Asp Ile Glu Asn Ser Ala Ile
    290                 295                 300

Pro Ser Pro Ser Phe Phe Arg Trp Leu Lys Ser Val Ser Ile Asn Ser
305                 310                 315                 320

Gln Trp Trp Gly Ser Gly Pro Asn Gln Thr Tyr Tyr Trp Val Gly His
                325                 330                 335

Glu Leu Val Tyr Thr Asn Ser Asn Tyr Asn Gln Ser Leu Lys Val Lys
            340                 345                 350

Tyr Gly Asp Pro Asn Ser Tyr Ile Glu Pro Pro Asp Ser Phe Asn Phe
        355                 360                 365

Ser Ser Thr Asp Val Tyr Arg Thr Ile Ser Ile Ala Lys Asn Ser Ile
    370                 375                 380

Ser Asn Tyr Ile Val Ser Glu Val Arg Phe Asn Ser Ile Ser Asn Thr
385                 390                 395                 400
```

```
Asn Lys Ile Ser Glu Glu Ile Tyr Lys His Gln Ser Asn Trp Pro Leu
            405                 410                 415

Lys Glu Thr Lys Asp Ser Ile Ala Glu Leu Ser Ile Ala Ala Asn Pro
            420                 425                 430

Pro Thr Thr Phe Gly Asn Val Ala Glu Tyr Ser His Arg Leu Ala Tyr
            435                 440                 445

Ile Ser Glu Ala Tyr Ser Ser His Asn Pro Ser Lys Tyr Pro Ala Tyr
            450                 455                 460

Ile Pro Val Tyr Gly Trp Thr His Thr Ser Val Arg Tyr Asp Asn Lys
465                 470                 475                 480

Ile Tyr Pro Asp Lys Ile Thr Gln Ile Pro Ala Val Lys Ser Ala Ser
                485                 490                 495

Val Glu Gly Gly Thr Trp Lys Asn Val Val Lys Gly Pro Gly Phe Thr
            500                 505                 510

Gly Gly Asp Val Thr Thr Ala Val Ser Pro Ala Asn Leu Ile Asp Val
            515                 520                 525

Ile Lys Ile His Val Thr Leu Asp Ser Asn Ser Leu Ser Gln Lys Tyr
            530                 535                 540

Arg Ala Arg Leu Arg Tyr Ala Ser Asn Ala Tyr Val Ala Ala Thr Leu
545                 550                 555                 560

Tyr Thr Asn Thr Ser Ser Asn Tyr His Phe Glu Leu Thr Lys Gly Thr
                565                 570                 575

Thr Glu Gln Phe Ser Thr Tyr Asn Ser Phe Gln Tyr Val Asp Ile Pro
            580                 585                 590

Gly Ser Ile Gln Phe Asn Asn Thr Ser Asp Thr Val Ser Val Tyr Leu
        595                 600                 605

His Met Asp Ser Thr Thr Asn Ala Ser Val Gln Val Asp Arg Ile Glu
            610                 615                 620

Phe Ile Pro Val Asp Ile Asn Tyr Asp Glu Arg Val Gln Leu Glu Lys
625                 630                 635                 640

Thr Gln Lys Ala Val Thr Ala Leu Phe Thr Ala Gly Lys His Ala Leu
                645                 650                 655

Gln Thr Asp Val Thr Asp Tyr Lys Val Asp Gln Val Ser Ile Leu Val
            660                 665                 670

Asp Cys Val Ser Ser Glu Leu Tyr Pro Asn Glu Lys Arg Glu Leu Gln
            675                 680                 685

Asn Leu Val Lys Tyr Ala Lys Arg Leu Ser Tyr Ser Arg Asn Leu Leu
        690                 695                 700

Leu Asp Pro Thr Phe Asp Ser Ile Asn Ser Ser Val Glu Asn Gly Trp
705                 710                 715                 720

Tyr Gly Ser Asn Gly Ile Ala Ile Gly Asn Gly Asp Tyr Val Phe Lys
                725                 730                 735

Gly Asn Tyr Leu Ile Phe Ser Gly Thr Asn Asp Thr Gln Tyr Pro Thr
            740                 745                 750

Tyr Leu Tyr Gln Lys Ile Asp Glu Ser Lys Leu Lys Glu Tyr Thr Arg
            755                 760                 765

Tyr Lys Leu Arg Gly Phe Ile Glu Asn Ser Gln Asp Leu Glu Ala Tyr
        770                 775                 780

Val Val Arg Tyr Asp Ala Lys His Glu Thr Leu Asp Val Ser Asn Asn
785                 790                 795                 800

Leu Leu Pro Asp Val Leu Pro Val Asn Ala Cys Gly Glu Pro Asn Arg
                805                 810                 815

Cys Val Ala Leu Gln Tyr Leu Asp Lys Asn Pro Arg Leu Glu Cys Ser
```

```
                    820                 825                 830
Ser Ile Gln Asp Gly Ile Leu Ser Asp Ser His Ser Phe Ser Leu Asn
        835                 840                 845

Ile Asp Thr Gly Ser Ile Asp Leu Asn Glu Asn Val Gly Ile Trp Val
850                 855                 860

Leu Phe Lys Ile Ser Thr Pro Glu Gly Tyr Ala Lys Phe Gly Asn Leu
865                 870                 875                 880

Glu Val Ile Glu Asp Gly Pro Val Ser Gly Glu Ala Leu Ala Arg Val
                885                 890                 895

Lys Arg Gln Glu Thr Lys Trp Arg Asn Lys Leu Ala Gln Leu Arg Thr
            900                 905                 910

Glu Thr Gln Ala Ile Tyr Thr Arg Ala Lys Gln Ala Leu Asp Asn Leu
        915                 920                 925

Phe Thr Asp Ala Gln Asp Ser Tyr Leu Lys Ile Gly Ala Thr Phe Ala
    930                 935                 940

Ala Ile Val Ala Ala Arg Lys Ile Val Gln Ser Ile Arg Glu Ala Tyr
945                 950                 955                 960

Met Ser Trp Leu Ser Val Val Pro Gly Val Asn Tyr Pro Ile Phe Thr
                965                 970                 975

Glu Leu Asn Glu Arg Val Gln Arg Ala Phe Gln Leu Tyr Asp Gly Arg
            980                 985                 990

Asn Val Val Arg Asn Gly Gln Phe Leu Asn Gly Val Leu Asp Trp Ile
        995                 1000                1005

Val Thr Ser Asp Val Ser Val Gln Glu Glu Asn Gly Asn Asn Val Leu
    1010                1015                1020

Val Leu Ser Asn Trp Asp Ala Gln Val Leu Gln Cys Leu Lys Leu Tyr
1025                1030                1035                1040

Gln Asp Arg Gly Tyr Ile Leu Arg Val Thr Ala Arg Lys Glu Gly Leu
                1045                1050                1055

Gly Glu Gly Tyr Ile Thr Ile Thr Asp Glu Glu Gly Asn Thr Asp Gln
            1060                1065                1070

Leu Thr Phe Gly Ser Cys Glu Glu Ile Asp Thr Ser Asn Ser Phe Val
        1075                1080                1085

Ser Thr Gly Tyr Met Thr Lys Glu Leu Glu Phe Phe Pro Asp Thr Glu
    1090                1095                1100

Lys Val His Ile Glu Ile Gly Glu Thr Glu Gly Ile Phe Gln Val Glu
1105                1110                1115                1120

Ser Val Glu Leu Phe Leu Met Glu Asp Leu Cys
                1125                1130

<210> SEQ ID NO 56
<211> LENGTH: 775
<212> TYPE: PRT
<213> ORGANISM: Bacillus thuringiensis

<400> SEQUENCE: 56

Met Arg Ile Asn Pro Ile Ile Lys Cys Val Ala Thr Thr Thr Leu Phe
 1               5                  10                  15

Ser Gln Phe Leu Thr Tyr Ser Ser Val Ser Tyr Ala Glu Glu Lys Gln
                20                  25                  30

Ser Gln Thr Lys Ile Lys Gln Val Met Gln Ser Glu Lys Ala Ser Gln
            35                  40                  45

Val Ser Asn Glu Ser Ser Gln Gly Leu Leu Gly Tyr Tyr Phe Gln Asp
        50                  55                  60

Ser Asn Phe Gln Gln Leu Thr Met Met Ala His Arg Gln Val Ser Asp
```

-continued

```
                65                  70                  75                  80
Leu Gln Ile Thr Lys Lys Glu Val Lys Asn Leu Leu Ala Asp Asp Gln
                    85                  90                  95

Gln His Ile Gly Ser Val Arg Trp Ile Gly Tyr Ile Gln Pro Ser Gln
                    100                 105                 110

Thr Gly Asp Tyr Ile Leu Ser Thr Ser Ser Asp Gln Val Val Ile
                    115                 120                 125

Glu Leu Asp Gly Lys Ile Ile Leu Asn Gln Ser Ser Met Thr Glu Ala
                    130                 135                 140

Ile Gln Leu Glu Lys Gly Lys Pro Tyr Lys Ile Arg Ile Glu Tyr Val
145                 150                 155                 160

Pro Glu Asn Lys Lys Asn Lys Asp Asn Leu Leu Asp Phe Glu Leu Asn
                    165                 170                 175

Trp Ser Ile Ser Gly Gly Thr Ala Glu Pro Val Pro Asp Asn Asp Phe
                    180                 185                 190

Leu Leu Pro Asp Leu Ser Arg Lys Gln Asp Gln Glu Lys Ile Ile Pro
                    195                 200                 205

Glu Thr Ser Leu Phe Glu Glu Lys Gly Glu Glu Lys Asn Val Ser Arg
                    210                 215                 220

Ser Lys Arg Ser Leu Ala Val Asn Pro Leu Leu Asp Thr Asp Asp Asp
225                 230                 235                 240

Gly Ile Tyr Asp Glu Trp Glu Thr Asn Gly Tyr Thr Ile Gln Gly Gln
                    245                 250                 255

Leu Ala Val Arg Trp Asn Asn Ser Met Lys Glu Gln Asn Tyr Pro Lys
                    260                 265                 270

Tyr Val Ser Asn Pro Tyr Lys Ser His Thr Val Ala Asp Pro Tyr Thr
                    275                 280                 285

Asp Trp Glu Lys Ala Ser Gly Arg Ile Asp Gln Ala Val Lys Arg Glu
                    290                 295                 300

Ala Lys Asn Pro Leu Val Ala Ala Tyr Pro Val Val Gly Val Asn Met
305                 310                 315                 320

Glu Arg Leu Ile Val Ser Glu Asn Gln Asn Ile Ser Thr Gly Leu Gly
                    325                 330                 335

Arg Thr Val Thr Ala Ser Thr Ser Ala Ser Ser Thr Ala Gly Ile Thr
                    340                 345                 350

Ala Gly Ile Asp Ala Thr Val Gly Ala Ser Leu Leu Gly Pro Ser Gly
                    355                 360                 365

Ser Val Thr Ala His Phe Ser Tyr Thr Gly Ser Ser Thr Ala Ala Val
                    370                 375                 380

Glu Asn Ser Ser Ser Asn Asn Trp Ser Asp Asp Leu Gly Ile Asn Thr
385                 390                 395                 400

Ala His Ser Ala Tyr Leu Asn Ala Asn Val Arg Tyr Tyr Asn Thr Gly
                    405                 410                 415

Thr Ala Pro Ile Tyr Asn Val Thr Pro Thr Thr Asn Phe Val Leu Asp
                    420                 425                 430

Ser Glu Thr Ile Val Thr Val Arg Ala Lys Glu Asn Gln Leu Gly Asp
                    435                 440                 445

Val Leu Lys Ala Gly Gly Thr Tyr Pro Glu Lys His Leu Asn Pro Ile
                    450                 455                 460

Ala Leu Asn Thr Leu Asp Asp Phe Gly Ser Gln Leu Ile Pro Ile Asn
465                 470                 475                 480

Tyr Asp Gln Thr Lys Arg Leu Glu Asn Gly Asn Lys Leu Gln Leu Gln
                    485                 490                 495
```

Thr Thr Gln Ala Ser Gly Leu Tyr Gly Lys Met Asn Ser Asn Gly Gly
                500                 505                 510

Leu Asn Ile His Pro Ser Gln Glu Trp Glu Pro Val Arg Ala Gln Ile
            515                 520                 525

Glu Ser Val Ser Ala Gly Ile Val Leu Asp Thr Gly Glu Glu Val Leu
        530                 535                 540

Glu Arg Arg Val Ala Thr Arg Asp Asp Arg Asp Pro Glu Asp Leu Thr
545                 550                 555                 560

Pro Glu Ile Thr Ile Gly Glu Ala Ile Lys Ile Ala Phe Asp Thr Thr
                565                 570                 575

Glu Gln Gly Gly Lys Leu Gln Tyr Lys Asp Thr Pro Leu Asn Glu Ser
            580                 585                 590

Leu Val Glu Leu Ile Val Asp Glu Ser Thr Ala Arg Glu Ile Lys Ala
        595                 600                 605

Gln Leu Asp Gly Asn Pro Gly Leu Glu Lys Lys Ile Tyr Asn Val Lys
    610                 615                 620

Leu Lys Arg Gly Met Asn Ile Met Leu Lys Lys Pro Ile Trp Tyr Ser
625                 630                 635                 640

Asp Phe Asp Thr His Gln His Asn Trp Ser Asn Ile Thr Ile Ala Pro
                645                 650                 655

Glu Glu Gly Ile Thr Gly Asn Ala Gly Lys Ile Ser Gln Gly Ser Val
            660                 665                 670

Gln Pro Ala Phe Leu Arg Tyr Gln Thr Val Glu Asp Phe Lys Asn Leu
        675                 680                 685

Lys Pro Asn Thr Arg Tyr Lys Leu Ser Ala Ser Ile Arg Tyr Leu Asp
    690                 695                 700

Leu Glu Pro Gly Gly Val Thr Gly Ala Tyr Ile Arg Val Asn Asp Leu
705                 710                 715                 720

Pro Asn Asn Glu Tyr Leu Ile Arg Ser Asn Leu Tyr Glu Arg Ile Glu
                725                 730                 735

Ser Thr Phe Thr Thr Gly Ile Ile Pro Ser Gly Ile Thr Asp Phe Arg
            740                 745                 750

Ile Ala Thr Thr Gly Ser Arg Asp Met Leu Leu Asp Asp Ile Thr Leu
        755                 760                 765

Val Glu Leu Gly Pro Ser Asn
    770                 775

<210> SEQ ID NO 57
<211> LENGTH: 672
<212> TYPE: PRT
<213> ORGANISM: Bacillus thuringiensis

<400> SEQUENCE: 57

Met Lys Asn Met Asn Ser Tyr Gln Asn Lys Asn Lys Asn Glu Tyr Glu
1               5                   10                  15

Ile Leu Asp Thr Ser Arg Ser Ser Thr Met Ser Thr Arg Tyr Pro
            20                  25                  30

Arg Tyr Pro Leu Ala Glu Asn Pro Gln Ile Ser Met Gln Asn Thr Asn
        35                  40                  45

Tyr Lys Asp Trp Ile Asn Met Cys Ala Ser Arg Asn Leu Glu Asp Gly
    50                  55                  60

Ile Tyr Pro Thr Ser Ala Asn Asp Val Ile Thr Ser Ile Asn Ile
65                  70                  75                  80

Ser Ser Tyr Ile Leu Ser Met Leu Gly Met Pro Asn Leu Ser Ser Ile
                85                  90                  95

-continued

```
Ile Ala Ile Trp Gly Val Leu Phe Asn Ala Phe Trp Pro Val Ser Gly
                100                 105                 110

Asn Gln Trp Glu His Tyr Met Asn His Val Gln Ala Leu Ile Lys Arg
            115                 120                 125

Glu Leu Gln Ala Phe Ala Arg Glu Gln Ala Leu Arg Gln Leu Glu Gly
130                 135                 140

Leu Gly Gly Asn Leu Gly Leu Tyr Lys Glu Ala Leu Ala Glu Trp Glu
145                 150                 155                 160

Gln Asp Arg Asp Asn Pro Thr Thr Lys Glu Arg Val Arg Asp Arg Phe
                165                 170                 175

Arg Ile Leu Asp Gly Phe Phe Thr Gln Tyr Ile Pro Val Phe Arg Ile
            180                 185                 190

Gln Gly Tyr Glu Val Gln Leu Leu Ser Ile Tyr Ala Lys Val Val Asn
        195                 200                 205

Leu His Leu Leu Leu Leu Arg Asp Ala Ser Met Phe Gly Ala Asp Trp
210                 215                 220

Gly Met Ser Gln Thr Asn Ile Asn Asp Asn Tyr Asn Arg Gln Met Lys
225                 230                 235                 240

Leu Thr Ser Leu Tyr Thr Asn His Cys Val Asp Phe Tyr Asn Gln Gly
                245                 250                 255

Leu Asn Glu Ala Arg Ala Leu Ser Asn Ser Ser Trp Asp Ile Phe Asn
            260                 265                 270

Asp Tyr Arg Arg Glu Met Thr Leu Thr Val Leu Asp Ile Val Ala Leu
        275                 280                 285

Phe Pro Ala Tyr Asp Tyr Arg Arg Tyr Pro Ile Thr Thr Lys Val Glu
290                 295                 300

Leu Thr Arg Glu Ile Tyr Thr Pro Ala Ile Ala Ser Gln Thr Trp Ser
305                 310                 315                 320

Asn His Asn His Leu Ser Pro Asn Val Asn Phe Gln Phe Tyr Glu Asn
                325                 330                 335

Asn Leu Val Arg Pro Pro Ala Phe Phe Thr Trp Leu Asp Arg Thr Glu
            340                 345                 350

Met Phe Ser Arg Asn Leu Ser Ile Glu Val Ser Glu Ala Trp Gly Gly
        355                 360                 365

His Ile Asn His Phe His His Thr Gly Glu Gln Pro Leu Ser Ser Arg
370                 375                 380

Ser Gly Phe Ile Gly Ser Asp Gln Arg Arg Val Ser Tyr Tyr Asp Phe
385                 390                 395                 400

Asn Phe Val Gly Asn Asp Val Phe Arg Ile Tyr Ser Arg Val Met Ser
                405                 410                 415

Asn Gln Val Gly Asn Phe Phe Gly Val Gly Gln Gly Asp Phe Phe Leu
            420                 425                 430

Val Asn Ser Asp Asn Ser Asn Thr Lys Thr Ile Ser Phe Thr Thr Arg
        435                 440                 445

Ala Thr Asn Ser Asn Gln Arg Ser Ile Phe Ser Gln Phe Pro Gly Glu
450                 455                 460

Asn Ser Asp Pro Pro Thr Ser Lys Asp Tyr Ser His Arg Leu Ser Trp
465                 470                 475                 480

Ile Ser Gly Ala Phe Ile Gly Ser Asp Leu Ala Asn Val Leu Ser Tyr
                485                 490                 495

Gly Trp Thr His Arg Ser Val Asp Pro Asn Asn Thr Ile Tyr Pro Asp
            500                 505                 510

Arg Ile Thr Gln Val Pro Ala Val Lys Ala Ser Ser Ala Pro Asp Cys
        515                 520                 525
```

```
Thr Val Ile Leu Gly Pro Gly Ser Thr Gly Gly Asn Leu Val Ser Phe
    530                 535                 540

Gly Arg Ser Gly Arg Leu Asn Met Gln Phe Lys Phe Thr Asn Ile Gln
545                 550                 555                 560

Thr Glu Tyr Arg Val Arg Ile Arg Tyr Ala Ser Thr Ala Val Asn Thr
                565                 570                 575

Leu Phe Val Ser Phe Ser Asp Tyr Asn Arg Asp Ile Ala Leu Asn Ser
            580                 585                 590

Thr Gly Ala Leu Ser Leu Asn Asn Leu Arg Asn Glu Asn Phe Ala Tyr
        595                 600                 605

Phe Glu Val Pro Gly Gly Ile Phe Arg Pro Ala Leu Gly Asn Thr Leu
    610                 615                 620

Ile Ile Ser Asn Trp Thr Thr Val Ala Pro Arg Leu Val Ile Asp Lys
625                 630                 635                 640

Ile Glu Phe Ile Pro Ile Asn Ala Thr Thr Ala Arg Tyr Gly Ser Lys
                645                 650                 655

Gln Glu Leu Glu Lys Ala Thr Lys Val Val Asn Asn Leu Phe Ile Asn
            660                 665                 670

<210> SEQ ID NO 58
<211> LENGTH: 1225
<212> TYPE: PRT
<213> ORGANISM: Bacillus thuringiensis

<400> SEQUENCE: 58

Met Ser Pro Asn Asn Gln Asn Glu Tyr Glu Ile Ile Asp Ala Thr Pro
 1               5                  10                  15

Ser Thr Ser Val Ser Asn Asp Ser Asn Arg Tyr Pro Phe Ala Asn Glu
                20                  25                  30

Pro Thr Asn Ala Leu Gln Asn Met Asn Tyr Lys Glu Tyr Leu Ser Met
            35                  40                  45

Ser Glu Gly Tyr Asp Arg Glu Tyr Phe Ala Ser Pro Gly Ala Leu Val
        50                  55                  60

Ser Gly Lys Gln Ala Ile Lys Val Gly Ile Asp Ile Val Gly Lys Ile
65                  70                  75                  80

Leu Gly Ala Leu Gly Ile Pro Phe Val Gly Glu Ile Val Gly Phe Tyr
                85                  90                  95

Asn Phe Ile Leu Asp Gln Leu Trp Pro Ser Asn Ser Val Ser Ile Trp
            100                 105                 110

Glu Gln Ile Met Thr Leu Val Glu Glu Leu Val Asp Gln Lys Ile Thr
        115                 120                 125

Glu Tyr Ala Arg Asn Lys Ala Ile Ala Glu Leu Thr Gly Leu Gly Asn
    130                 135                 140

Ala Met Asp Val Tyr Gln Gln Ser Leu Glu Asp Trp Val Ala Asn Pro
145                 150                 155                 160

Asn Asp Ala Arg Thr Arg Ser Val Val Ala Thr Gln Phe Thr Ala Leu
                165                 170                 175

Glu Leu Asp Phe Val Gln Ala Ile Pro Ser Phe Ala Ile Ser Gly Gln
            180                 185                 190

Glu Val Pro Leu Leu Gly Val Tyr Ala Gln Ala Val Asn Leu His Leu
        195                 200                 205

Leu Leu Leu Arg Asp Ala Ser Ile Phe Gly Glu Glu Trp Gly Phe Ser
    210                 215                 220

Ser Ser Glu Ile Ser Arg Tyr Tyr Asn Arg Gln Val Gln Leu Thr Ser
225                 230                 235                 240
```

-continued

```
Gln Tyr Ser Asp Tyr Cys Val Lys Trp Tyr Asn Thr Gly Leu Gln Lys
                245                 250                 255

Leu Lys Gly Thr Ser Ala Glu Asn Trp Leu Glu Tyr His Gln Phe Arg
            260                 265                 270

Arg Glu Met Thr Phe Met Val Leu Asp Leu Val Ala Leu Phe Pro Asn
        275                 280                 285

Tyr Asn Thr His Met Tyr Pro Leu Glu Thr Lys Ala Gln Leu Thr Arg
    290                 295                 300

Glu Val Tyr Thr Asp Pro Ile Ala Phe Asn Leu Ser Gly Ala Ala Gly
305                 310                 315                 320

Phe Cys Ser Pro Trp Ser Lys Tyr Thr Gly Ile Ser Phe Ser Glu Ile
                325                 330                 335

Glu Asn Ala Val Ile Arg Pro Pro His Leu Phe Asn Val Leu Arg Ser
            340                 345                 350

Leu Glu Ile Asn Thr Val Arg Gly Thr Ile Leu Gly Asn Thr Lys Asp
        355                 360                 365

Phe Gln Asn Tyr Trp Ser Gly His Ser Leu Arg Tyr Asn Phe Ile Gly
    370                 375                 380

Asn Thr Thr Ile Ser Glu Ser Asn Tyr Gly Tyr Leu Thr Ser Glu Lys
385                 390                 395                 400

Thr Arg Ile Glu Leu Asp Thr Arg Asp Ile Phe Glu Ile Asn Ser Thr
                405                 410                 415

Ala Ala Asn Leu Ala Asn Tyr Tyr Gln Gln Val Tyr Gly Val Pro Gln
            420                 425                 430

Ser Gly Phe His Met Val Arg Trp Asp Ser Pro Tyr Asn Thr Ser Thr
        435                 440                 445

Gln Leu Tyr Ser Lys Thr Tyr Thr Thr Pro Lys Asp Cys Thr Gln Val
    450                 455                 460

Tyr Gln Ser Ser Glu Glu Ile Pro Val Glu Arg Thr Val Pro Val Asn
465                 470                 475                 480

Glu Gly Tyr Ser His Arg Leu Ser Tyr Val Thr Ser Phe Asp Phe Ser
                485                 490                 495

Lys Ile Ile Asn Ser Phe Val Arg Asn Gly Asn Leu Pro Val Phe Val
            500                 505                 510

Trp Thr His Arg Ser Ala Asp Leu Thr Asn Thr Ile Tyr Pro Asp Val
        515                 520                 525

Ile Thr Gln Ile Pro Val Val Lys Ala Tyr Ala Leu Gly Ser Ser Ile
    530                 535                 540

Leu Pro Gly Ser Pro Ser Pro Thr Ile Val Pro Gly Pro Gly Phe Thr
545                 550                 555                 560

Gly Gly Asp Ile Ile Gln Leu Leu Ala Asn Thr Lys Gly Ile Ala Tyr
                565                 570                 575

Met Asn Phe Glu Ile Gln Asp Ile Asn Lys Glu Tyr Ile Met Arg Ile
            580                 585                 590

Arg Tyr Ala Ser Ala Ala Asn Pro Glu Phe Asn Ile Ala Val Gly Thr
        595                 600                 605

Ser Gly Glu Arg Val Ser Thr Ser Ala Gln Lys Thr Met Asn Pro Gly
    610                 615                 620

Asp Ile Leu Thr Phe Asn Lys Phe Asn Tyr Ala Thr Phe Pro Pro Ile
625                 630                 635                 640

Lys Phe Asn Ser Thr Lys Ile Ser Ile Ala Leu Thr Ala Ser Leu Ala
                645                 650                 655

Ala Phe Ala Ser Thr Leu Leu Glu Thr Tyr Ile Asp Arg Ile Glu Phe
```

```
                      660                 665                 670
Ile Pro Val Asp Glu Thr Tyr Glu Ala Glu Ala Asp Leu Glu Ala Ala
                675                 680                 685

Lys Lys Ala Val Asn Ala Leu Phe Thr Asn Thr Lys Asp Gly Leu Arg
        690                 695                 700

Pro Gly Val Thr Asp Tyr Glu Val Asn Gln Ala Ala Asn Leu Val Glu
705                 710                 715                 720

Cys Leu Ser Asp Asp Leu Tyr Pro Asn Glu Lys Arg Leu Leu Phe Asp
                725                 730                 735

Ala Val Arg Glu Ala Lys Arg Leu Ser Glu Ala Arg Asn Leu Leu Gln
            740                 745                 750

Asp Pro Asp Phe Gln Glu Ile Asn Gly Glu Asn Gly Trp Thr Ala Ser
        755                 760                 765

Thr Gly Val Glu Ile Ile Glu Gly Asp Ala Val Phe Lys Gly Arg Tyr
    770                 775                 780

Leu Arg Leu Pro Gly Ala Arg Glu Ile Asp Thr Glu Thr Tyr Pro Thr
785                 790                 795                 800

Tyr Val Tyr Gln Lys Ile Glu Glu Gly Val Leu Lys Pro Tyr Thr Arg
                805                 810                 815

Tyr Arg Leu Arg Gly Phe Val Gly Ser Ser Gln Gly Leu Glu Ile Phe
            820                 825                 830

Thr Ile Arg His Gln Thr Asn Arg Ile Val Lys Asn Val Pro Asp Asp
        835                 840                 845

Leu Leu Pro Asp Val Pro Val Asn Ser Asp Gly Arg Ile Asn Arg
    850                 855                 860

Cys Ser Glu Gln Lys Tyr Val Asn Ser Arg Leu Glu Gly Arg Gly
865                 870                 875                 880

Leu Pro Asn Gly Asn Arg Ser Ala Glu Ala His Glu Phe Ser Leu Pro
                885                 890                 895

Ile Asp Ile Gly Glu Leu Asp Tyr Asn Glu Asn Ala Gly Ile Trp Val
            900                 905                 910

Gly Phe Lys Ile Thr Asp Pro Glu Gly Tyr Ala Thr Leu Gly Asn Leu
        915                 920                 925

Glu Leu Val Glu Glu Gly Pro Leu Ser Gly Asp Ala Leu Glu Arg Leu
    930                 935                 940

Gln Arg Glu Glu Gln Gln Trp Lys Leu Gln Met Thr Lys Arg Arg Glu
945                 950                 955                 960

Glu Thr Asp Arg Lys Tyr Met Ala Ala Lys Gln Ala Val Asp Arg Leu
                965                 970                 975

Tyr Ala Asp Tyr Gln Asp Gln Gln Leu Asn Pro Asn Val Glu Ile Thr
            980                 985                 990

Asp Ile Thr Ala Ala Gln Asp Leu Ile Gln Ser Ile Pro Tyr Val Tyr
        995                 1000                1005

Asn Glu Ile Phe Pro Glu Ile Gln Gly Met Asn Tyr Ala Lys Phe Thr
    1010                1015                1020

Glu Leu Ser Asn Arg Leu Gln Arg Ala Trp Gly Leu Tyr Asp Gln Arg
1025                1030                1035                1040

Asn Ala Ile Pro Asn Gly Asp Phe Arg Asn Gly Leu Ser Asn Trp Asn
                1045                1050                1055

Thr Thr Pro Gly Val Glu Val Gln Gln Ile Asn Asp Thr Ser Val Leu
            1060                1065                1070

Val Ile Pro Asn Trp Asp Glu Gln Val Ser Gln Phe Thr Val Gln
        1075                1080                1085
```

```
Pro Asn Gln Arg Tyr Val Leu Arg Val Thr Ala Arg Lys Glu Gly Val
    1090                1095                1100

Gly Asn Gly Tyr Val Ser Ile Arg Asp Gly Gly Asn Gln Thr Glu Thr
1105                1110                1115                1120
Leu Thr Phe Ser Ala Ser Asp Tyr Asp Thr Asn Asn Val Tyr Asn Thr
                1125                1130                1135
Gln Ala Ser Asn Thr Asn Gly Tyr Asn Thr Asn Asn Ala Tyr Asn Thr
            1140                1145                1150

Gln Val Ser Asn Thr Asn Gly Tyr Asn Thr Asn Asn Ala Tyr Asn Thr
        1155                1160                1165

Asn Gly Tyr Asn Thr Gln Ala Ser Asn Thr Asn Gly Leu Tyr Asn Glu
    1170                1175                1180

Gln Thr Gly Tyr Ile Thr Lys Thr Val Thr Phe Ile Pro Tyr Thr Glu
1185                1190                1195                1200
Gln Val Trp Ile Glu Met Ser Glu Thr Glu Gly Thr Phe Tyr Ile Glu
                1205                1210                1215
Ser Val Glu Leu Ile Val Asp Val Glu
            1220                1225

<210> SEQ ID NO 59
<211> LENGTH: 1184
<212> TYPE: PRT
<213> ORGANISM: Bacillus thuringiensis

<400> SEQUENCE: 59

Met Cys Phe Leu Cys His Arg Arg His Ile Gly Asp Cys Leu Phe Asn
 1               5                  10                  15

Leu Ile Tyr Phe Leu Glu Val Asn Tyr Met Asp Ile Arg Asn Gln Lys
            20                  25                  30

Lys Ser Glu Glu Ile His Pro Thr Leu Asn Glu Ser Ser Ser Asn Thr
        35                  40                  45

Thr Ser Lys Tyr Pro Leu Ala Ser Asp Leu Ile Lys Gln Tyr Gln Asn
    50                  55                  60

Met Asn Tyr Lys Asp Ser Leu Asn Ile Ile Glu Glu Asn Asn Val Ile
65                  70                  75                  80

Asp Pro Val Ser Gly Thr Ala Ala Leu Val Thr Ala Arg Lys Ile Gly
                85                  90                  95

Gly Lys Ile Ile Lys Lys Leu Gly Glu Ala Ala Leu Ser Lys Ile Leu
            100                 105                 110

Lys Glu Ile Leu Gly Tyr Leu Trp Pro Thr Ser Gly Glu Asp Asp Ser
        115                 120                 125

Trp Thr Asp Met Met Thr Ala Val Glu Glu Leu Ile Asp Gln Lys Ile
    130                 135                 140

Gln Glu Gln Val Glu Leu Asp Ala Leu Thr Glu Leu Glu Lys Ile Gly
145                 150                 155                 160

Glu Ala Val Glu Ala Tyr Tyr Ile Ala Leu Asp Asp Trp Glu Pro Val
                165                 170                 175

Pro Glu Asp Met Phe Ser Leu Ser Glu Val Ile Lys Arg Tyr Asp Phe
            180                 185                 190

Ala Gln Gln Leu Ala Arg Ala Ser Met Pro Glu Phe Lys Lys Lys Gly
        195                 200                 205

Tyr Glu Ile Pro Leu Leu Ala Thr Tyr Ala Asn Ala Ala Asn Val His
    210                 215                 220

Leu Leu Leu Met Arg Asp Met Gln Ile Tyr Gly Glu Arg Trp Gly Ile
225                 230                 235                 240
```

-continued

Pro Lys Glu Asp Ile Glu Leu Tyr Leu Ser Glu Gln Glu Asn Phe Thr
            245                 250                 255

Ser Glu Tyr Thr Asp His Cys Val Lys Tyr Tyr Asn Glu Gly Leu Asn
            260                 265                 270

Gln Leu Lys Asn Lys Ser Gly Val Ser Gly Leu Val Trp Glu Asn Tyr
        275                 280                 285

Asn Arg Phe Arg Thr Glu Met Thr Ile Leu Val Leu Asp Ile Val Ala
    290                 295                 300

Val Phe Pro Arg Tyr Asn Val Ile Glu Tyr Pro Ile Asp Ser Thr Val
305                 310                 315                 320

Glu Leu Thr Arg Thr Ile Tyr Leu Asp Pro Leu Gly Tyr Thr Gly Asn
                325                 330                 335

Ser Asn Asp Glu His Pro Glu Tyr Tyr Ala Ser Thr Lys Ser Phe Ser
            340                 345                 350

Ser Ile Glu Ser Arg Ala Ile Pro Ala Pro Thr Leu Phe Gln Trp Ile
        355                 360                 365

Thr Glu Leu Gln Val Tyr Ser Ala Lys Gly Ser His Gly Ser Thr Tyr
    370                 375                 380

Thr Thr Trp Trp Thr Gly His Lys Val Thr Ala Lys Pro Thr Asn Gly
385                 390                 395                 400

Gly Leu Glu Ser Lys Tyr Asp Phe Gly Ser Ser Ser Gly Ser Gln Asn
                405                 410                 415

Lys Asp Val Phe Ala Leu Asp Gly Lys Asp Val Tyr Asp Ser Gln Ser
            420                 425                 430

Met Leu Thr Ser Ile Ser Tyr Ser Gly Ile Arg Tyr Phe Gly Cys Pro
        435                 440                 445

Gln Phe Lys Leu Asn Trp Ile Asn Lys Asn Glu Leu Ala Glu Gln
    450                 455                 460

Ile Phe Asn Tyr Ser Ser Asn Val Gly Ser Ser Phe Ser Glu Tyr Arg
465                 470                 475                 480

Tyr Ser Lys Asp Glu Leu Pro Ile Glu Leu Leu Ala Ser Pro Ile Tyr
                485                 490                 495

Gly Asp Ile Glu Glu Tyr Ser His Arg Leu Ser His Val Ser Glu Val
            500                 505                 510

Ile Lys Asp Tyr Gly Gln Gly Ile Ile Pro Val Leu Gly Phe Thr His
        515                 520                 525

Val Ser Val Ser Arg Asp Asn Arg Ile Tyr Ser Asp Lys Ile Thr Gln
    530                 535                 540

Ile Pro Ala Val Lys Met Tyr Glu Leu Val Ser Pro Ala Val Val Val
545                 550                 555                 560

Lys Gly Pro Gly Ser Thr Gly Gly Asp Leu Val Lys Arg Gly Ser Ser
                565                 570                 575

Gly Asn Ile Gly Ser Met Asn Val Thr Val Asn Ser Pro Leu Ser Gln
            580                 585                 590

Lys Tyr Arg Val Arg Val Arg Tyr Ala Thr Asn Ala Ser Gly Gln Leu
        595                 600                 605

Asn Val Ser Ile Asn Asp Lys Leu Thr Leu Gln Lys Pro Phe Glu Arg
    610                 615                 620

Thr Gly Thr Thr Ile Gly Glu Gly Thr Asp Leu Ser Tyr Asp Ser Phe
625                 630                 635                 640

Gly Tyr Leu Glu Tyr Ser Thr Thr Ile Gln Phe Pro Asn Glu His Pro
                645                 650                 655

Lys Ile Thr Phe Asn Leu Ser His Trp Ser Gly Ser Gly Ala Phe Tyr
            660                 665                 670

```
Ile Asp Lys Ile Glu Phe Ile Pro Val Asp Glu Asn Tyr Asp Glu Arg
        675                 680                 685

Val Thr Leu Glu Lys Ala Gln Lys Ala Val Asn Ala Leu Phe Thr Ala
    690                 695                 700

Gly Arg Asn Ala Leu Gln Lys Asp Val Thr Asp Phe Lys Val Asp Gln
705                 710                 715                 720

Val Ser Ile Leu Val Asp Cys Ile Pro Gly Glu Leu Tyr Pro Asn Glu
            725                 730                 735

Lys Arg Glu Leu Leu Ser Leu Val Lys Tyr Ala Lys Arg Leu Ser Tyr
        740                 745                 750

Ser Arg Asn Leu Leu Asp Pro Thr Phe Asp Ser Ile Asn Ser Pro
        755                 760                 765

Asp Glu Asn Gly Trp Tyr Gly Ser Asn Gly Ile Ala Ile Gly Asn Gly
    770                 775                 780

Asn Phe Val Phe Lys Gly Asn Tyr Leu Ile Phe Ser Gly Thr Asn Asp
785                 790                 795                 800

Thr Gln Tyr Pro Thr Tyr Leu Tyr Gln Lys Ile Asp Glu Ser Lys Leu
            805                 810                 815

Lys Glu Tyr Thr Arg Tyr Lys Leu Arg Gly Phe Ile Glu Ser Ser Gln
        820                 825                 830

Asp Leu Glu Ala Tyr Val Ile Arg Tyr Asp Ala Lys His Glu Thr Leu
        835                 840                 845

Asp Val Ser Asn Asn Leu Phe Pro Asp Ile Ser Pro Val Asn Ala Cys
    850                 855                 860

Gly Glu Pro Asn Arg Cys Ala Ala Leu Gln Tyr Leu Asp Glu Asn Pro
865                 870                 875                 880

Arg Leu Glu Cys Ser Ser Ile Gln Asp Gly Ile Leu Ser Asp Ser His
            885                 890                 895

Ser Phe Ser Leu Asn Ile Asp Thr Gly Ser Ile Asp Tyr Asp Glu Asn
        900                 905                 910

Val Gly Ile Trp Val Leu Phe Lys Ile Ser Thr Pro Glu Gly Tyr Ala
    915                 920                 925

Lys Phe Gly Asn Leu Glu Val Ile Glu Asp Gly Leu Val Ile Gly Glu
930                 935                 940

Ala Leu Ala Arg Val Lys Arg Gln Glu Thr Lys Trp Arg Asn Lys Leu
945                 950                 955                 960

Thr Gln Leu Arg Thr Glu Thr Gln Ala Ile Tyr Thr Arg Ala Lys Gln
            965                 970                 975

Ala Ile Asp Asn Leu Phe Thr Asn Ala Gln Asp Ser His Leu Lys Ile
        980                 985                 990

Gly Ala Thr Phe Ala Ser Ile Val Ala Ala Arg Lys Ile Val Gln Ser
        995                 1000                1005

Ile Arg Glu Ala Tyr Met Ser Trp Leu Ser Ile Val Pro Ser Val Asn
    1010                1015                1020

Tyr Pro Ile Phe Thr Glu Leu Asn Glu Arg Val Gln Arg Ala Phe Arg
1025                1030                1035                1040

Leu Tyr Asp Val Arg Asn Val Val Arg Asn Gly Arg Phe Leu Ser Gly
            1045                1050                1055

Val Ser Asp Trp Ile Val Thr Asp Val Lys Val Gln Glu Glu Asn
        1060                1065                1070

Gly Asn Asn Val Leu Val Leu Ser Asn Trp Asp Ala Gln Val Leu Gln
        1075                1080                1085

Cys Leu Asn Leu Tyr Glu Asp His Gly Tyr Ile Leu Arg Val Thr Ala
```

```
                  1090                1095                1100
Arg Lys Glu Gly Leu Gly Glu Gly Tyr Ile Thr Ile Thr Asp Glu Glu
1105                1110                1115                1120

Gly His Thr Asp Gln Leu Thr Phe Gly Gly Cys Glu Glu Ile Asp Ser
                1125                1130                1135

Ser Asn Ser Phe Val Ser Thr Gly Tyr Ile Thr Lys Glu Leu Glu Phe
            1140                1145                1150

Phe Pro Asp Thr Glu Lys Val Arg Ile Glu Ile Gly Glu Thr Glu Gly
            1155                1160                1165

Thr Phe Gln Val Glu Ser Val Glu Leu Phe Leu Met Glu Asp Ile Cys
            1170                1175                1180

<210> SEQ ID NO 60
<211> LENGTH: 1102
<212> TYPE: PRT
<213> ORGANISM: Bacillus thuringiensis

<400> SEQUENCE: 60

Met Asn Tyr Lys Glu Tyr Leu Asn Ile Thr Glu Gly Gly Ile Ile Asn
1               5                   10                  15

Pro Thr Leu Ala Gly Ser Ala Ile Val Ala Gln Asn Val Ser Lys
            20                  25                  30

Thr Ile Leu Lys Lys Leu Gly Ser Thr Ile Leu Gly Lys Ile Leu Gly
        35                  40                  45

Ser Val Leu Asp Ile Leu Trp Pro Thr Asn Thr Glu Glu Ile Trp Leu
    50                  55                  60

Glu Leu Ile Asp Glu Val Glu Glu Leu Ile Asn Gln Lys Ile Glu Gln
65                  70                  75                  80

Gln Val Ile Ile Asp Ala Glu Thr Ala Leu Glu Ser Val Lys Leu Asn
                85                  90                  95

Val Asp Leu Tyr Leu Asn Ala Phe Glu Glu Trp Glu Lys Arg Pro Thr
            100                 105                 110

Asn Glu Tyr Ser Thr Glu Leu Val Tyr Lys Arg Phe Thr Asp Ala Tyr
        115                 120                 125

Asn Tyr Ala Arg Thr Ser Ile Pro Phe Phe Arg Val Lys Thr Tyr Glu
    130                 135                 140

Val Ser Leu Leu Ser Val Tyr Ala Gln Ala Ala Asn Ile Ser Leu Leu
145                 150                 155                 160

Leu Ser Arg Asp Ala Gln Ile Tyr Gly Asp Leu Trp Gly Phe Asp Glu
                165                 170                 175

His Asp Lys Ala Thr Phe Asp Ser Glu Arg Lys Leu Phe Arg Ala Glu
            180                 185                 190

Tyr Ile Asp His Cys Thr Lys Tyr Tyr Lys Val Gly Leu Asp Arg Leu
        195                 200                 205

Lys Gly Ser Ser Tyr Gly Ser Trp Val Asn Tyr Asn Arg Tyr Arg Arg
    210                 215                 220

Glu Met Thr Leu Met Ile Leu Asp Thr Ile Ala Ala Phe Pro Tyr Tyr
225                 230                 235                 240

Asp Ile Glu Glu Tyr Pro Ile Glu Val Ser Thr Gln Leu Ala Arg Glu
                245                 250                 255

Val Tyr Thr Asp Pro Ile Ile Ser Phe Val Glu Ser Asp His Gly
            260                 265                 270

Pro Ser Phe Ser Phe Met Glu Ser Asn Ala Ile Arg Lys Pro His Leu
        275                 280                 285

Val Asp Tyr Leu Asp Asn Leu Tyr Ile Tyr Thr Ser Arg Phe Arg Thr
```

-continued

```
                290                 295                 300
Phe Ser Asn Glu Phe Gln Pro Asp Leu Asn Tyr Trp Ala Ala His Lys
305                 310                 315                 320

Val Lys Tyr Lys Tyr Ser Gly Asp Pro Thr Leu His Glu Thr Pro Ile
                325                 330                 335

Tyr Gly Asn Ala Ser Asn Tyr Glu Ser Thr Gly Asn Tyr Ser Phe Arg
            340                 345                 350

Gly Asn Ser Ile Tyr Gln Thr Leu Ser Ala Pro Ser Ala Ile Leu Thr
            355                 360                 365

Pro Asn Tyr Ile Tyr Tyr Gly Ile Glu Gln Val Glu Phe Tyr Gly Asn
370                 375                 380

Lys Gly Asn Val Tyr Tyr Arg Gly Gly Asn Lys Tyr Pro Leu Ser Val
385                 390                 395                 400

Asp Ser Ala Asn Gln Leu Pro Pro Asp Val Glu Pro Ile Thr Glu Asn
                405                 410                 415

Tyr Asn His Val Leu Cys His Ala Thr Ala Val Pro Val Lys Asp Gly
            420                 425                 430

Gly Thr Val Pro Ile Phe Ser Trp Thr His Arg Ser Ala Asp Tyr Tyr
            435                 440                 445

Asn Thr Ile Tyr Pro Asp Lys Ile Thr Gln Leu Pro Ala Val Lys Ser
450                 455                 460

Thr Pro Ser Pro Glu Val Glu Gly Leu Lys Val Gln Glu Gly Pro Gly
465                 470                 475                 480

Phe Thr Gly Gly Asp Leu Val Val Ala Lys Ser Ser Asn Gln Thr Ile
                485                 490                 495

Val Arg Leu Lys Val Thr Val Asp Ser Pro Gly Thr Gln Lys Tyr Arg
            500                 505                 510

Ile Arg Leu Lys Tyr Ala Ala Thr Ser Asn Phe Tyr Leu Gly Ala Tyr
            515                 520                 525

Ala Gly Ser Asn Gly Gly Asn Gly Ile Pro Gly Ile Ser Thr Val Pro
            530                 535                 540

Lys Thr Met Asn Ile Glu Asp Pro Leu Ser Tyr Thr Ser Phe Ala Tyr
545                 550                 555                 560

Ile Asp Leu Pro Asp Ser Tyr Thr Phe Ser Gln Lys Asp Glu Val Ile
                565                 570                 575

Arg Phe Thr Ile Asn Ile Tyr Glu Ser Gly Gly Ala Val Tyr Ala Asp
            580                 585                 590

Lys Val Glu Phe Ile Pro Val Asp Ala Asp Tyr Asp Glu Gly Val Gln
            595                 600                 605

Leu Glu Lys Ala Gln Lys Ala Val Asn Ala Leu Phe Thr Ala Gly Arg
610                 615                 620

Asn Ala Leu Gln Thr Asp Val Thr Asp Tyr Lys Val Asp Gln Val Ser
625                 630                 635                 640

Ile Leu Val Asp Cys Val Ser Gly Glu Leu Tyr Pro Asn Glu Lys Arg
                645                 650                 655

Glu Leu Gln Asn Leu Ile Lys Tyr Ala Lys Arg Leu Ser Tyr Ser Arg
            660                 665                 670

Asn Leu Leu Leu Asp Pro Thr Phe Asp Ser Ile Asn Ser Ser Asp Glu
            675                 680                 685

Asn Gly Trp Tyr Gly Ser Asn Gly Ile Ala Ile Gly Ser Gly Asn Ile
            690                 695                 700

Val Phe Lys Gly Asn Tyr Leu Ile Phe Ser Gly Thr Asn Asp Glu Gln
705                 710                 715                 720
```

Tyr Pro Thr Tyr Leu Tyr Gln Lys Ile Asp Glu Ser Lys Leu Lys Glu
            725                 730                 735

Tyr Thr Arg Tyr Lys Leu Arg Gly Phe Ile Glu Ser Ser Gln Asp Leu
            740                 745                 750

Glu Ala Tyr Val Ile Arg Tyr Asp Ala Lys His Gln Thr Met Asp Val
            755                 760                 765

Ser Asn Asn Leu Phe Ser Asp Ile Thr Pro Val Asn Ala Cys Gly Glu
            770                 775                 780

Pro Asn Arg Cys Ala Ala Leu Pro Tyr Leu Asp Glu Asn Pro Arg Leu
785                 790                 795                 800

Glu Cys Ser Ser Ile Gln Asp Gly Ile Leu Ser Asp Ser His Ser Phe
            805                 810                 815

Ser Leu His Ile Asp Thr Gly Ser Ile Asp Phe Asn Glu Asn Val Gly
            820                 825                 830

Ile Trp Val Leu Phe Lys Ile Ser Thr Leu Glu Gly Tyr Ala Lys Phe
            835                 840                 845

Gly Asn Leu Glu Val Ile Glu Asp Gly Pro Val Ile Gly Glu Ala Leu
            850                 855                 860

Ala Arg Val Lys Arg Gln Glu Thr Lys Trp Arg Asn Lys Leu Thr Gln
865                 870                 875                 880

Leu Arg Thr Glu Thr Gln Ala Ile Tyr Thr Arg Ala Lys Gln Ala Ile
            885                 890                 895

Asp Asn Leu Phe Thr Asn Glu Gln Asp Ser His Leu Lys Ile Gly Thr
            900                 905                 910

Thr Phe Ala Leu Ile Val Ala Ala Arg Lys Ile Val Gln Ser Ile Arg
            915                 920                 925

Glu Ala Tyr Met Ser Trp Leu Ser Ile Val Pro Gly Val Asn Tyr Pro
            930                 935                 940

Ile Phe Thr Glu Leu Asn Glu Arg Val Gln Gln Ala Phe Gln Leu Tyr
945                 950                 955                 960

Asp Val Arg Asn Val Val Arg Asn Gly Arg Phe Gln Ser Gly Thr Ser
            965                 970                 975

Asp Trp Ile Val Thr Ser Asp Val Lys Val Gln Glu Glu Asn Gly Asn
            980                 985                 990

Asn Val Leu Val Leu Ser Asn Trp Asp Ala Gln Val Leu Gln Cys Met
            995                 1000                1005

Thr Leu Tyr Gln Asp Arg Gly Tyr Ile Leu Arg Val Thr Ala Arg Lys
            1010                1015                1020

Glu Gly Leu Gly Glu Gly Tyr Val Thr Ile Thr Asp Glu Glu Gly Asn
1025                1030                1035                1040

Thr Asp Gln Leu Arg Phe Gly Gly Cys Glu Glu Ile Asp Ala Ser Asn
            1045                1050                1055

Ser Phe Val Ser Thr Gly Tyr Val Thr Lys Glu Leu Glu Phe Phe Pro
            1060                1065                1070

Asp Thr Glu Lys Val Arg Ile Glu Ile Gly Glu Thr Glu Gly Ile Phe
            1075                1080                1085

Gln Val Gly Ser Val Glu Leu Phe Leu Met Glu Asp Leu Cys
            1090                1095                1100

<210> SEQ ID NO 61
<211> LENGTH: 1131
<212> TYPE: PRT
<213> ORGANISM: Bacillus thuringiensis

<400> SEQUENCE: 61

-continued

```
Met Asn Gln Lys Asn Tyr Glu Ile Ile Gly Ala Ser Thr Asn Gly Thr
 1               5                  10                  15

Ile Glu Leu Pro Glu Asp Tyr Asn Thr Ile Val Ser Pro Tyr Asp Ala
             20                  25                  30

Pro Ala Ser Val Thr Thr Thr Ile Glu Ile Thr Gly Thr Ile Leu Ser
             35                  40                  45

Asp Leu Gly Val Pro Gly Ala Ser Ser Val Ser Leu Leu Asn Lys
 50                  55                  60

Leu Ile Asn Leu Leu Trp Pro Asn Asp Thr Asn Thr Val Trp Gly Thr
 65                  70                  75                  80

Phe Gly Lys Glu Thr Ala Asp Leu Leu Asn Glu Val Leu Ser Pro Asp
                 85                  90                  95

Asp Pro Val Val Lys Asp Ala Asn Thr Ile Leu Lys Gly Ile Asn Gly
                100                 105                 110

Ser Leu Asn Leu Tyr Leu Asn Ala Leu Glu Ile Trp Lys Lys Asp Pro
                115                 120                 125

Asn Asn Leu Thr Thr Ile Glu Asn Val Thr Asp Tyr Phe Arg Ser Leu
        130                 135                 140

Asn Val Val Phe Thr His Asp Met Pro Ser Phe Ala Val Pro Gly Tyr
145                 150                 155                 160

Glu Thr Lys Leu Leu Thr Ile Tyr Ala Gln Ala Ala Asn Leu His Leu
                165                 170                 175

Leu Leu Leu Arg Asp Ala Ser Arg Phe Gly Glu Gly Trp Gly Leu Thr
            180                 185                 190

Gln Glu Ile Ile Asn Thr Asn Tyr Asn Asp Gln Leu Arg Leu Thr Ala
            195                 200                 205

Glu Tyr Thr Asp His Cys Val Lys Trp Tyr Asn Ala Gly Leu Glu Lys
210                 215                 220

Leu Lys Gly Asn Leu Thr Gly Glu Asn Trp Tyr Thr Tyr Asn Arg Phe
225                 230                 235                 240

Arg Arg Glu Met Thr Leu Met Val Leu Asp Val Val Ala Leu Phe Pro
                245                 250                 255

Asn Tyr Asp Thr Arg Met Tyr Pro Ile Gly Thr Ser Ser Glu Leu Thr
            260                 265                 270

Arg Met Ile Tyr Thr Asp Pro Ile Ala Tyr Thr Gln Ser Asp Pro Trp
        275                 280                 285

Tyr Lys Ile Thr Ser Leu Ser Phe Ser Asn Ile Glu Asn Ser Ala Ile
        290                 295                 300

Pro Ser Pro Ser Phe Phe Arg Trp Leu Lys Ser Val Ser Ile Asn Ser
305                 310                 315                 320

Gln Trp Trp Gly Ser Gly Pro Ser Gln Thr Tyr Tyr Trp Val Gly His
                325                 330                 335

Glu Leu Val Tyr Ser Asn Ser Asn Ser Asn Gln Ser Leu Lys Val Lys
            340                 345                 350

Tyr Gly Asp Pro Asn Ser Phe Ile Glu Pro Pro Asp Ser Phe Ser Phe
        355                 360                 365

Ser Ser Thr Asp Val Tyr Arg Thr Ile Ser Val Val Arg Asn Ser Val
370                 375                 380

Ser Asn Tyr Ile Val Ser Glu Val Arg Phe Asn Ser Ile Ser Ser Thr
385                 390                 395                 400

Asn Gln Ile Ser Glu Glu Ile Tyr Lys His Gln Ser Asn Trp Ser Arg
            405                 410                 415

Gln Glu Thr Lys Asp Ser Ile Thr Glu Leu Ser Leu Ala Ala Asn Pro
        420                 425                 430
```

```
Pro Thr Thr Phe Gly Asn Val Ala Glu Tyr Ser His Arg Leu Ala Tyr
        435                 440                 445

Ile Ser Glu Ala Tyr Gln Ser His Asn Pro Ser Lys Tyr Pro Thr Tyr
    450                 455                 460

Ile Pro Val Phe Gly Trp Thr His Thr Ser Val Arg Tyr Asp Asn Lys
465                 470                 475                 480

Ile Phe Pro Asp Lys Ile Thr Gln Ile Pro Ala Val Lys Ser Ser Ser
                485                 490                 495

Ala Gln Gly Gly Ser Trp Lys Asn Ile Val Lys Gly Pro Gly Phe Thr
            500                 505                 510

Gly Gly Asp Val Thr Thr Ala Val Ser Pro Ala Thr Val Thr Asp Ile
        515                 520                 525

Ile Lys Ile Gln Val Thr Leu Asp Pro Asn Ser Leu Ser Gln Lys Tyr
    530                 535                 540

Arg Ala Arg Leu Arg Tyr Ala Ser Asn Ala Phe Val Pro Ala Thr Leu
545                 550                 555                 560

Tyr Thr Asn Thr Ser Ser Asn Tyr Asn Phe Glu Leu Lys Lys Gly Thr
                565                 570                 575

Thr Glu Gln Phe Thr Thr Tyr Asn Ser Tyr Gln Tyr Val Asp Ile Pro
            580                 585                 590

Gly Ser Ile Gln Phe Asn Asn Thr Ser Asp Thr Val Ser Val Tyr Leu
        595                 600                 605

His Met Asp Ser Thr Ser Asn Val Asn Val His Val Asp Arg Ile Glu
    610                 615                 620

Phe Ile Pro Ile Asp Glu Asn Tyr Asp Glu Arg Phe Gln Leu Glu Lys
625                 630                 635                 640

Ala Gln Lys Ala Val Asn Ala Leu Phe Thr Ala Gly Arg Asn Ala Leu
                645                 650                 655

Gln Thr Asp Val Thr Asp Tyr Lys Val Asp Gln Val Ser Ile Leu Val
            660                 665                 670

Asp Cys Val Ser Gly Glu Leu Tyr Pro Asn Glu Lys Arg Glu Leu Leu
        675                 680                 685

Ser Leu Val Lys Tyr Ala Lys Arg Leu Ser Tyr Ser Arg Asn Leu Leu
    690                 695                 700

Leu Asp Pro Thr Phe Asp Ser Ile Asn Ser Pro Glu Glu Asn Gly Trp
705                 710                 715                 720

Tyr Gly Ser Asn Gly Ile Ala Ile Gly Ser Gly Asn Ile Val Phe Lys
                725                 730                 735

Gly Asn Tyr Leu Ile Phe Ser Gly Thr Asn Asp Glu Gln Tyr Pro Thr
            740                 745                 750

Tyr Leu Tyr Gln Lys Ile Asp Glu Thr Lys Leu Lys Glu Tyr Thr Arg
        755                 760                 765

Tyr Lys Leu Arg Gly Phe Ile Glu Ser Ser Gln Asp Leu Glu Ala Tyr
    770                 775                 780

Val Ile Arg Tyr Asp Ala Lys His Gln Thr Met Asp Val Ser Asn Asn
785                 790                 795                 800

Leu Phe Ser Asp Ile Thr Pro Val Asn Ala Cys Gly Glu Pro Asn Arg
                805                 810                 815

Cys Ala Ala Leu Pro Tyr Leu Asp Glu Asn Pro Arg Leu Glu Cys Ser
            820                 825                 830

Ser Ile Gln Asp Gly Ile Leu Ser Asp Ser His Ser Phe Ser Leu His
        835                 840                 845

Ile Asp Thr Gly Ser Ile Asp Phe Asn Glu Asn Val Gly Ile Trp Val
```

```
    850                 855                 860

Leu Phe Lys Ile Ser Thr Pro Glu Gly Tyr Ala Arg Phe Gly Asn Leu
865                 870                 875                 880

Glu Val Ile Glu Asp Gly Pro Val Ile Gly Glu Ala Leu Ala Arg Val
                885                 890                 895

Lys Arg Gln Glu Thr Lys Trp Arg Asn Lys Leu Thr Gln Leu Arg Thr
            900                 905                 910

Glu Thr Gln Ala Ile Tyr Thr Arg Ala Lys Gln Ala Ile Asp Asn Leu
        915                 920                 925

Phe Thr Asn Ala Gln Asp Ser His Leu Lys Ile Gly Ala Thr Phe Ala
    930                 935                 940

Ser Ile Val Ala Ala Arg Lys Ile Val Gln Ser Ile Arg Glu Ala Tyr
945                 950                 955                 960

Met Ser Trp Leu Ser Ile Val Pro Gly Val Asn Tyr Pro Ile Val Thr
                965                 970                 975

Glu Leu Asn Glu Arg Ile Gln Gln Ala Phe Gln Leu Tyr Asp Val Arg
            980                 985                 990

Asn Val Val Arg Asn Gly Arg Phe Gln Ser Gly Thr Ser Asp Trp Ile
        995                 1000                1005

Val Thr Ser Asp Val Arg Val Gln Glu Glu Asn Gly Asn Asn Val Leu
    1010                1015                1020

Val Leu Ser Asn Trp Asp Ala Gln Val Leu Gln Cys Met Thr Leu Tyr
1025                1030                1035                1040

Gln Asp Arg Gly Tyr Ile Leu Arg Val Thr Ala Arg Lys Glu Gly Leu
                1045                1050                1055

Gly Glu Gly Tyr Val Thr Ile Thr Asp Glu Glu Gly Asn Thr Asp Gln
            1060                1065                1070

Leu Arg Phe Gly Gly Cys Glu Glu Ile Asp Ala Ser Asn Ser Phe Val
        1075                1080                1085

Ser Thr Gly Tyr Met Thr Lys Glu Leu Glu Phe Phe Pro Asp Thr Glu
    1090                1095                1100

Lys Val Arg Ile Glu Ile Gly Glu Thr Glu Gly Thr Phe Gln Val Glu
1105                1110                1115                1120

Ser Val Glu Leu Phe Leu Met Glu Asp Leu Cys
                1125                1130
```

<210> SEQ ID NO 62
<211> LENGTH: 1206
<212> TYPE: PRT
<213> ORGANISM: Bacillus thuringiensis

<400> SEQUENCE: 62

```
Met Ser Pro Asn Asn Gln Asn Glu Tyr Glu Ile Ile Asp Ala Thr Pro
 1               5                  10                  15

Ser Thr Ser Val Ser Asn Asp Ser Asn Arg Tyr Pro Phe Ala Asn Glu
            20                  25                  30

Pro Thr Asn Ala Leu Gln Asn Met Asp Tyr Lys Asp Tyr Leu Lys Met
        35                  40                  45

Ser Ala Gly Asn Ala Ser Glu Tyr Pro Gly Ser Pro Glu Val Leu Val
    50                  55                  60

Ser Gly Gln Asp Ala Ala Lys Ala Ala Ile Asp Ile Val Gly Lys Leu
65                  70                  75                  80

Leu Ser Gly Leu Gly Val Pro Phe Val Gly Pro Ile Val Ser Leu Tyr
                85                  90                  95

Thr Gln Leu Ile Asp Ile Leu Trp Pro Ser Gly Glu Lys Ser Gln Trp
```

-continued

```
                100                 105                 110
Glu Ile Phe Met Glu Gln Val Glu Glu Leu Ile Asn Gln Lys Ile Ala
            115                 120                 125
Glu Tyr Ala Arg Asn Lys Ala Leu Ser Glu Leu Glu Gly Leu Gly Asn
        130                 135                 140
Asn Tyr Gln Leu Tyr Leu Thr Ala Leu Glu Glu Trp Glu Glu Asn Pro
145                 150                 155                 160
Asn Gly Ser Arg Ala Leu Arg Asp Val Arg Asn Arg Phe Glu Ile Leu
                165                 170                 175
Asp Ser Leu Phe Thr Gln Tyr Met Pro Ser Phe Arg Val Thr Asn Phe
            180                 185                 190
Glu Val Pro Phe Leu Thr Val Tyr Ala Met Ala Ala Asn Leu His Leu
        195                 200                 205
Leu Leu Leu Lys Asp Ala Ser Ile Phe Gly Glu Glu Trp Gly Trp Ser
210                 215                 220
Thr Thr Thr Ile Asn Asn Tyr Tyr Asp Arg Gln Met Lys Leu Thr Ala
225                 230                 235                 240
Glu Tyr Ser Asp His Cys Val Lys Trp Tyr Glu Thr Gly Leu Ala Lys
                245                 250                 255
Leu Lys Gly Thr Ser Ala Lys Gln Trp Val Asp Tyr Asn Gln Phe Arg
            260                 265                 270
Arg Glu Met Thr Leu Ala Val Leu Asp Val Val Ala Leu Phe Pro Asn
        275                 280                 285
Tyr Asp Thr Arg Thr Tyr Pro Met Glu Thr Lys Ala Gln Leu Thr Arg
    290                 295                 300
Glu Val Tyr Thr Asp Pro Leu Gly Ala Val Asn Val Ser Ser Ile Gly
305                 310                 315                 320
Ser Trp Tyr Asp Lys Ala Pro Ser Phe Gly Val Ile Glu Ser Ser Val
                325                 330                 335
Ile Arg Pro Pro His Val Phe Asp Tyr Ile Thr Gly Leu Thr Val Tyr
            340                 345                 350
Thr Gln Ser Arg Ser Ile Ser Ser Ala Arg Tyr Ile Arg His Trp Ala
        355                 360                 365
Gly His Gln Ile Ser Tyr His Arg Val Ser Arg Gly Ser Asn Leu Gln
    370                 375                 380
Gln Met Tyr Gly Thr Asn Gln Asn Leu His Ser Thr Ser Thr Phe Asp
385                 390                 395                 400
Phe Thr Asn Tyr Asp Ile Tyr Lys Thr Leu Ser Lys Asp Ala Val Leu
                405                 410                 415
Leu Asp Ile Val Tyr Pro Gly Tyr Thr Tyr Ile Phe Phe Gly Met Pro
            420                 425                 430
Glu Val Glu Phe Phe Met Val Asn Gln Leu Asn Asn Thr Arg Lys Thr
        435                 440                 445
Leu Lys Tyr Asn Pro Val Ser Lys Asp Ile Ile Ala Ser Thr Arg Asp
    450                 455                 460
Ser Glu Leu Glu Leu Pro Pro Glu Thr Ser Asp Gln Pro Asn Tyr Glu
465                 470                 475                 480
Ser Tyr Ser His Arg Leu Cys His Ile Thr Ser Ile Pro Ala Thr Gly
                485                 490                 495
Asn Thr Thr Gly Leu Val Pro Val Phe Ser Trp Thr His Arg Ser Ala
            500                 505                 510
Asp Leu Asn Asn Thr Ile Tyr Ser Asp Lys Ile Thr Gln Ile Pro Ala
        515                 520                 525
```

```
Val Lys Cys Trp Asp Asn Leu Pro Phe Val Pro Val Lys Gly Pro
        530                 535                 540

Gly His Thr Gly Gly Asp Leu Leu Gln Tyr Asn Arg Ser Thr Gly Ser
545                 550                 555                 560

Val Gly Thr Leu Phe Leu Ala Arg Tyr Gly Leu Ala Leu Glu Lys Ala
                565                 570                 575

Gly Lys Tyr Arg Val Arg Leu Arg Tyr Ala Thr Asp Ala Asp Ile Val
                580                 585                 590

Leu His Val Asn Asp Ala Gln Ile Gln Met Pro Lys Thr Met Asn Pro
        595                 600                 605

Gly Glu Asp Leu Thr Ser Lys Thr Phe Lys Val Ala Asp Ala Ile Thr
        610                 615                 620

Thr Leu Asn Leu Ala Thr Asp Ser Ser Leu Ala Leu Lys His Asn Leu
625                 630                 635                 640

Gly Glu Asp Pro Asn Ser Thr Leu Ser Gly Ile Val Tyr Val Asp Arg
                645                 650                 655

Ile Glu Phe Ile Pro Val Asp Glu Thr Tyr Glu Ala Glu Gln Asp Leu
                660                 665                 670

Glu Ala Ala Lys Lys Ala Val Asn Ala Leu Phe Thr Asn Thr Lys Asp
        675                 680                 685

Gly Leu Arg Pro Gly Val Thr Asp Tyr Glu Val Asn Gln Ala Ala Asn
690                 695                 700

Leu Val Glu Cys Leu Ser Asp Asp Leu Tyr Pro Asn Glu Lys Arg Leu
705                 710                 715                 720

Leu Phe Asp Ala Val Arg Glu Ala Lys Arg Leu Ser Glu Ala Arg Asn
                725                 730                 735

Leu Leu Gln Asp Pro Asp Phe Gln Glu Ile Asn Gly Glu Asn Gly Trp
        740                 745                 750

Thr Ala Ser Thr Gly Ile Glu Val Ile Glu Gly Asp Ala Leu Phe Lys
        755                 760                 765

Gly Arg Tyr Leu Arg Leu Pro Gly Ala Arg Glu Ile Asp Thr Glu Thr
770                 775                 780

Tyr Pro Thr Tyr Leu Tyr Gln Lys Val Glu Glu Gly Val Leu Lys Pro
785                 790                 795                 800

Tyr Thr Arg Tyr Arg Leu Arg Gly Phe Val Gly Ser Ser Gln Gly Leu
                805                 810                 815

Glu Ile Phe Thr Ile Arg His Gln Thr Asn Arg Ile Val Lys Asn Val
                820                 825                 830

Pro Asp Asp Leu Leu Pro Asp Val Ser Pro Val Asn Ser Asp Gly Ser
        835                 840                 845

Ile Asn Arg Cys Ser Glu Gln Lys Tyr Val Asn Ser Arg Leu Glu Val
850                 855                 860

Glu Asn Arg Ser Gly Glu Ala His Glu Phe Ser Ile Pro Ile Asp Thr
865                 870                 875                 880

Gly Glu Ile Asp Tyr Asn Glu Asn Ala Gly Ile Trp Val Gly Phe Lys
                885                 890                 895

Ile Thr Asp Pro Glu Gly Tyr Ala Thr Leu Gly Asn Leu Glu Leu Val
                900                 905                 910

Glu Glu Gly Pro Leu Ser Gly Asp Ala Leu Glu Arg Leu Gln Arg Glu
        915                 920                 925

Glu Gln Gln Trp Lys Ile Gln Met Thr Arg Arg Arg Glu Glu Thr Asp
        930                 935                 940

Arg Arg Tyr Met Ala Ser Lys Gln Ala Val Asp Arg Leu Tyr Ala Asp
945                 950                 955                 960
```

```
Tyr Gln Asp Gln Gln Leu Asn Pro Asp Val Glu Ile Thr Asp Leu Thr
            965                 970                 975

Ala Ala Gln Asp Leu Ile Gln Ser Ile Pro Tyr Val Tyr Asn Glu Met
            980                 985                 990

Phe Pro Glu Ile Pro Gly Met Asn Tyr Thr Lys Phe Thr Glu Leu Thr
            995                 1000                1005

Asp Arg Leu Gln Gln Ala Trp Ser Leu Tyr Asp Gln Arg Asn Ala Ile
    1010                1015                1020

Pro Asn Gly Asp Phe Arg Asn Gly Leu Ser Asn Trp Asn Ala Thr Pro
1025                1030                1035                1040

Gly Val Glu Val Gln Gln Ile Asn His Thr Ser Val Leu Val Ile Pro
                1045                1050                1055

Asn Trp Asp Glu Gln Val Ser Gln Phe Thr Val Gln Pro Asn Gln
                1060                1065                1070

Arg Tyr Val Leu Arg Val Thr Ala Arg Lys Glu Gly Val Gly Asn Gly
                1075                1080                1085

Tyr Val Ser Ile Arg Asp Gly Gly Asn Gln Thr Glu Thr Leu Thr Phe
                1090                1095                1100

Ser Ala Ser Asp Tyr Asp Thr Asn Gly Met Tyr Asn Thr Gln Val Ser
1105                1110                1115                1120

Asn Thr Asn Gly Tyr Asn Thr Asn Ala Tyr Asn Thr Gln Ala Ser
                1125                1130                1135

Ser Thr Asn Gly Tyr Asn Ala Asn Asn Met Tyr Asn Thr Gln Ala Ser
                1140                1145                1150

Asn Thr Asn Gly Tyr Asn Thr Asn Ser Val Tyr Asn Asp Gln Thr Gly
                1155                1160                1165

Tyr Ile Thr Lys Thr Val Thr Phe Ile Pro Tyr Thr Asp Gln Met Trp
                1170                1175                1180

Ile Glu Met Ser Glu Thr Glu Gly Thr Phe Tyr Ile Glu Ser Val Glu
1185                1190                1195                1200

Leu Ile Val Asp Val Glu
                1205

<210> SEQ ID NO 63
<211> LENGTH: 1210
<212> TYPE: PRT
<213> ORGANISM: Bacillus thuringiensis

<400> SEQUENCE: 63

Met Ser Pro Asn Asn Gln Asn Glu Tyr Glu Ile Ile Asp Ala Thr Pro
  1               5                  10                  15

Ser Thr Ser Val Ser Asn Asp Ser Asn Arg Tyr Pro Phe Ala Asn Glu
             20                  25                  30

Pro Thr Asn Ala Leu Gln Asn Met Asp Tyr Lys Asp Tyr Leu Lys Met
         35                  40                  45

Ser Ala Gly Asn Ala Ser Glu Tyr Pro Gly Ser Pro Glu Val Leu Val
     50                  55                  60

Ser Gly Gln Asp Ala Ala Lys Ala Ala Ile Asp Ile Val Gly Lys Leu
 65                  70                  75                  80

Leu Ser Gly Leu Gly Val Pro Phe Val Gly Pro Ile Val Ser Leu Tyr
                 85                  90                  95

Thr Gln Leu Ile Asp Ile Leu Trp Pro Ser Gly Gln Lys Ser Gln Trp
            100                 105                 110

Glu Ile Phe Met Glu Gln Val Glu Glu Leu Ile Asn Gln Lys Ile Ala
        115                 120                 125
```

```
Glu Tyr Ala Arg Asn Lys Ala Leu Ser Glu Leu Glu Gly Leu Gly Asn
    130                 135                 140

Asn Tyr Gln Leu Tyr Leu Thr Ala Leu Glu Glu Trp Lys Glu Asn Pro
145                 150                 155                 160

Asn Gly Ser Arg Ala Leu Arg Asp Val Arg Asn Arg Phe Glu Ile Leu
                165                 170                 175

Asp Ser Leu Phe Thr Gln Tyr Met Pro Ser Phe Arg Val Thr Asn Phe
            180                 185                 190

Glu Val Pro Phe Leu Thr Val Tyr Thr Gln Ala Ala Asn Leu His Leu
        195                 200                 205

Leu Leu Leu Lys Asp Ala Ser Ile Phe Gly Glu Glu Trp Gly Trp Ser
    210                 215                 220

Thr Thr Thr Ile Asn Asn Tyr Tyr Asp Arg Gln Met Lys Leu Thr Ala
225                 230                 235                 240

Glu Tyr Ser Asp His Cys Val Lys Trp Tyr Glu Thr Gly Leu Ala Lys
                245                 250                 255

Leu Lys Gly Thr Ser Ala Lys Gln Trp Val Asp Tyr Asn Gln Phe Arg
            260                 265                 270

Arg Glu Met Thr Leu Thr Val Leu Asp Val Val Ala Leu Phe Pro Asn
        275                 280                 285

Tyr Asp Thr Arg Thr Tyr Pro Met Glu Thr Lys Ala Gln Leu Thr Arg
    290                 295                 300

Glu Val Tyr Thr Asp Pro Leu Gly Ala Val Asn Val Ser Ser Ile Gly
305                 310                 315                 320

Ser Trp Tyr Asp Lys Ala Pro Ser Phe Gly Val Ile Glu Ser Ser Val
                325                 330                 335

Ile Arg Pro Pro His Val Phe Asp Tyr Ile Thr Gly Leu Thr Val Tyr
            340                 345                 350

Thr Gln Ser Arg Ser Ile Ser Ser Ala Arg Tyr Ile Arg His Trp Ala
        355                 360                 365

Gly His Gln Ile Ser Tyr His Arg Ile Phe Ser Asp Asn Ile Ile Lys
    370                 375                 380

Gln Met Tyr Gly Thr Asn Gln Asn Leu His Ser Thr Ser Thr Phe Asp
385                 390                 395                 400

Phe Thr Asn Tyr Asp Ile Tyr Lys Thr Leu Ser Lys Asp Ala Val Leu
                405                 410                 415

Leu Asp Ile Val Phe Pro Gly Tyr Thr Tyr Ile Phe Phe Gly Met Pro
            420                 425                 430

Glu Val Glu Phe Phe Met Val Asn Gln Leu Asn Asn Thr Arg Lys Thr
        435                 440                 445

Leu Lys Tyr Asn Pro Val Ser Lys Asp Ile Ile Ala Gly Thr Arg Asp
    450                 455                 460

Ser Glu Leu Glu Leu Pro Pro Glu Thr Ser Asp Gln Pro Asn Tyr Glu
465                 470                 475                 480

Ser Tyr Ser His Arg Leu Cys His Ile Thr Ser Ile Pro Ala Thr Gly
                485                 490                 495

Ser Thr Thr Gly Leu Val Pro Val Phe Ser Trp Thr His Arg Ser Ala
            500                 505                 510

Asp Leu Ile Asn Ala Val His Ser Asp Lys Ile Thr Gln Ile Pro Val
        515                 520                 525

Val Lys Val Ser Asp Leu Ala Pro Ser Ile Thr Gly Gly Pro Asn Asn
    530                 535                 540

Thr Val Val Ser Gly Pro Gly Phe Thr Gly Gly Gly Ile Ile Lys Val
```

-continued

```
          545                 550                 555                 560
Ile Arg Asn Gly Val Ile Ile Ser His Met Arg Val Lys Ile Ser Asp
                565                 570                 575
Ile Asn Lys Glu Tyr Ser Met Arg Ile Arg Tyr Ala Ser Ala Asn Asn
                580                 585                 590
Thr Glu Phe Tyr Ile Asn Pro Ser Glu Glu Asn Val Lys Ser His Ala
                595                 600                 605
Gln Lys Thr Met Asn Arg Gly Glu Ala Leu Thr Tyr Asn Lys Phe Asn
                610                 615                 620
Tyr Ala Thr Leu Pro Pro Ile Lys Phe Thr Thr Thr Glu Pro Phe Ile
625                 630                 635                 640
Thr Leu Gly Ala Ile Phe Glu Ala Glu Asp Phe Leu Gly Ile Glu Ala
                645                 650                 655
Tyr Ile Asp Arg Ile Glu Phe Ile Pro Val Asp Glu Thr Tyr Glu Ala
                660                 665                 670
Glu Gln Asp Leu Glu Ala Ala Lys Lys Ala Val Asn Ala Leu Phe Thr
                675                 680                 685
Asn Thr Lys Asp Gly Leu Arg Pro Gly Val Thr Asp Tyr Glu Val Asn
                690                 695                 700
Gln Ala Ala Asn Leu Val Glu Cys Leu Ser Asp Leu Tyr Pro Asn
705                 710                 715                 720
Glu Lys Arg Leu Leu Phe Asp Ala Val Arg Glu Ala Lys Arg Leu Ser
                725                 730                 735
Glu Ala Arg Asn Leu Leu Gln Asp Pro Asp Phe Gln Glu Ile Asn Gly
                740                 745                 750
Glu Asn Gly Trp Thr Ala Ser Thr Gly Ile Glu Val Ile Glu Gly Asp
                755                 760                 765
Ala Leu Phe Lys Gly Arg Tyr Leu Arg Leu Pro Gly Ala Arg Glu Ile
                770                 775                 780
Asp Thr Glu Thr Tyr Pro Thr Tyr Leu Tyr Gln Lys Val Glu Glu Gly
785                 790                 795                 800
Val Leu Lys Pro Tyr Thr Arg Tyr Arg Leu Arg Gly Phe Val Gly Ser
                805                 810                 815
Ser Gln Gly Leu Glu Ile Phe Thr Ile Arg His Gln Thr Asn Arg Ile
                820                 825                 830
Val Lys Asn Val Pro Asp Asp Leu Leu Pro Asp Val Ser Pro Val Asn
                835                 840                 845
Ser Asp Gly Ser Ile Asn Arg Cys Ser Glu Gln Lys Tyr Val Asn Ser
850                 855                 860
Arg Leu Glu Val Glu Asn Arg Ser Gly Glu Ala His Glu Phe Ser Ile
865                 870                 875                 880
Pro Ile Asp Thr Gly Glu Ile Asp Tyr Asn Glu Asn Ala Gly Ile Trp
                885                 890                 895
Val Gly Phe Lys Ile Thr Asp Pro Glu Gly Tyr Ala Thr Leu Gly Asn
                900                 905                 910
Leu Glu Leu Val Glu Glu Gly Pro Leu Ser Gly Asp Ala Leu Glu Arg
                915                 920                 925
Leu Gln Arg Glu Glu Gln Gln Trp Lys Ile Gln Met Thr Arg Arg Arg
                930                 935                 940
Glu Glu Thr Asp Arg Arg Tyr Met Ala Ser Lys Gln Ala Val Asp Arg
945                 950                 955                 960
Leu Tyr Ala Asp Tyr Gln Asp Gln Gln Leu Asn Pro Asp Val Glu Ile
                965                 970                 975
```

```
Thr Asp Leu Thr Ala Ala Gln Asp Leu Ile Gln Ser Ile Pro Tyr Val
            980                 985                 990

Tyr Asn Glu Met Phe Pro Glu Ile Pro Gly Met Asn Tyr Thr Lys Phe
            995                1000                1005

Thr Glu Leu Thr Asp Arg Leu Gln Gln Ala Trp Ser Leu Tyr Asp Gln
           1010                1015                1020

Arg Asn Ala Ile Pro Asn Gly Asp Phe Arg Asn Gly Leu Ser Asn Trp
           1025                1030                1035                1040

Asn Ala Thr Pro Gly Val Glu Val Gln Gln Ile Asn His Thr Ser Val
           1045                1050                1055

Leu Val Ile Pro Asn Trp Asp Glu Gln Val Ser Gln Gln Phe Thr Val
           1060                1065                1070

Gln Pro Asn Gln Arg Tyr Val Leu Arg Val Thr Ala Arg Lys Glu Gly
           1075                1080                1085

Val Gly Asn Gly Tyr Val Ser Ile Arg Asp Gly Gly Asn Gln Thr Glu
           1090                1095                1100

Thr Leu Thr Phe Ser Ala Ser Asp Tyr Asp Thr Asn Gly Met Tyr Asn
           1105                1110                1115                1120

Thr Gln Val Ser Asn Thr Asn Gly Tyr Asn Thr Asn Asn Ala Tyr Asn
                       1125                1130                1135

Thr Gln Ala Ser Ser Thr Asn Gly Tyr Asn Ala Asn Asn Met Tyr Asn
                       1140                1145                1150

Thr Gln Ala Ser Asn Thr Asn Gly Tyr Asn Thr Asn Ser Val Tyr Asn
                       1155                1160                1165

Asp Gln Thr Gly Tyr Ile Thr Lys Thr Val Thr Phe Ile Pro Tyr Thr
           1170                1175                1180

Asp Gln Met Trp Ile Glu Met Ser Glu Thr Glu Gly Thr Phe Tyr Ile
1185                1190                1195                1200

Glu Ser Val Glu Leu Ile Val Asp Val Glu
                       1205                1210

<210> SEQ ID NO 64
<211> LENGTH: 1138
<212> TYPE: PRT
<213> ORGANISM: Bacillus thuringiensis

<400> SEQUENCE: 64

Met Asn Leu Asn Asn Leu Asp Gly Tyr Glu Asp Ser Asn Arg Thr Leu
 1               5                  10                  15

Asn Asn Ser Leu Asn Tyr Pro Thr Gln Lys Ala Leu Ser Pro Ser Leu
                20                  25                  30

Lys Asn Met Asn Tyr Gln Asp Phe Leu Ser Ile Thr Glu Arg Glu Gln
            35                  40                  45

Pro Glu Ala Leu Ala Ser Gly Asn Thr Ala Ile Asn Thr Val Val Ser
 50                  55                  60

Val Thr Gly Ala Thr Leu Ser Ala Leu Gly Val Pro Gly Ala Ser Phe
65                  70                  75                  80

Ile Thr Asn Phe Tyr Leu Lys Ile Ala Gly Leu Leu Trp Pro Glu Asn
                85                  90                  95

Gly Lys Ile Trp Asp Glu Phe Met Thr Glu Val Glu Ala Leu Ile Asp
            100                 105                 110

Gln Lys Ile Glu Glu Tyr Val Arg Asn Lys Ala Ile Ala Glu Leu Asp
        115                 120                 125

Gly Leu Gly Ser Ala Leu Asp Lys Tyr Gln Lys Ala Leu Ala Asp Trp
130                 135                 140
```

```
Leu Gly Lys Gln Asp Asp Pro Glu Ala Ile Leu Ser Val Ala Thr Glu
145                 150                 155                 160

Phe Arg Ile Ile Asp Ser Leu Phe Glu Phe Ser Met Pro Ser Phe Lys
                165                 170                 175

Val Thr Gly Tyr Glu Ile Pro Leu Leu Thr Val Tyr Ala Gln Ala Ala
            180                 185                 190

Asn Leu His Leu Ala Leu Leu Arg Asp Ser Thr Leu Tyr Gly Asp Lys
        195                 200                 205

Trp Gly Phe Thr Gln Asn Asn Ile Glu Glu Asn Tyr Asn Arg Gln Lys
    210                 215                 220

Lys Arg Ile Ser Glu Tyr Ser Asp His Cys Thr Lys Trp Tyr Asn Ser
225                 230                 235                 240

Gly Leu Ser Arg Leu Asn Gly Ser Thr Tyr Glu Gln Trp Ile Asn Tyr
                245                 250                 255

Asn Arg Phe Arg Arg Glu Met Ile Leu Met Ala Leu Asp Leu Val Ala
                260                 265                 270

Val Phe Pro Phe His Asp Pro Arg Arg Tyr Ser Met Glu Thr Ser Thr
            275                 280                 285

Gln Leu Thr Arg Glu Val Tyr Thr Asp Pro Val Ser Leu Ser Ile Ser
290                 295                 300

Asn Pro Asp Ile Gly Pro Ser Phe Ser Gln Met Glu Asn Thr Ala Ile
305                 310                 315                 320

Arg Thr Pro His Leu Val Asp Tyr Leu Asp Glu Leu Tyr Ile Tyr Thr
                325                 330                 335

Ser Lys Tyr Lys Ala Phe Ser His Glu Ile Gln Pro Asp Leu Phe Tyr
            340                 345                 350

Trp Ser Ala His Lys Val Ser Phe Lys Lys Ser Glu Gln Ser Asn Leu
        355                 360                 365

Tyr Thr Thr Gly Ile Tyr Gly Lys Thr Ser Gly Tyr Ile Ser Ser Gly
    370                 375                 380

Ala Tyr Ser Phe His Gly Asn Asp Ile Tyr Arg Thr Leu Ala Ala Pro
385                 390                 395                 400

Ser Val Val Val Tyr Pro Tyr Thr Gln Asn Tyr Gly Val Glu Gln Val
                405                 410                 415

Glu Phe Tyr Gly Val Lys Gly His Val His Tyr Arg Gly Asp Asn Lys
            420                 425                 430

Tyr Asp Leu Thr Tyr Asp Ser Ile Asp Gln Leu Pro Pro Asp Gly Glu
        435                 440                 445

Pro Ile His Glu Lys Tyr Thr His Arg Leu Cys His Ala Thr Ala Ile
    450                 455                 460

Phe Lys Ser Thr Pro Asp Tyr Asp Asn Ala Thr Ile Pro Ile Phe Ser
465                 470                 475                 480

Trp Thr His Arg Ser Ala Glu Tyr Tyr Asn Arg Ile Tyr Pro Asn Lys
                485                 490                 495

Ile Thr Lys Ile Pro Ala Val Lys Met Tyr Lys Leu Asp Asp Pro Ser
            500                 505                 510

Thr Val Val Lys Gly Pro Gly Phe Thr Gly Gly Asp Leu Val Lys Arg
        515                 520                 525

Gly Ser Thr Gly Tyr Ile Gly Asp Ile Lys Ala Thr Val Asn Ser Pro
    530                 535                 540

Leu Ser Gln Lys Tyr Arg Val Arg Val Arg Tyr Ala Thr Asn Val Ser
545                 550                 555                 560

Gly Gln Phe Asn Val Tyr Ile Asn Asp Lys Ile Thr Leu Gln Thr Lys
                565                 570                 575
```

```
Phe Gln Asn Thr Val Glu Thr Ile Gly Glu Gly Lys Asp Leu Thr Tyr
                580                 585                 590
Gly Ser Phe Gly Tyr Ile Glu Tyr Ser Thr Thr Ile Gln Phe Pro Asp
            595                 600                 605
Glu His Pro Lys Ile Thr Leu His Leu Ser Asp Leu Ser Asn Asn Ser
610                 615                 620
Ser Phe Tyr Val Asp Ser Ile Glu Phe Ile Pro Val Asp Val Asn Tyr
625                 630                 635                 640
Ala Glu Lys Glu Lys Leu Glu Lys Ala Gln Lys Ala Val Asn Thr Leu
                645                 650                 655
Phe Thr Glu Gly Arg Asn Ala Leu Gln Lys Asp Val Thr Asp Tyr Lys
                660                 665                 670
Val Asp Gln Val Ser Ile Leu Val Asp Cys Ile Ser Gly Asp Leu Tyr
            675                 680                 685
Pro Asn Glu Lys Arg Glu Leu Gln Asn Leu Val Lys Tyr Ala Lys Arg
690                 695                 700
Leu Ser Tyr Ser Arg Asn Leu Leu Asp Pro Thr Phe Asp Ser Ile
705                 710                 715                 720
Asn Ser Ser Glu Glu Asn Gly Trp Tyr Gly Ser Asn Gly Ile Val Ile
                725                 730                 735
Gly Asn Gly Asp Phe Val Phe Lys Gly Asn Tyr Leu Ile Phe Ser Gly
                740                 745                 750
Thr Asn Asp Thr Gln Tyr Pro Thr Tyr Leu Tyr Gln Lys Ile Asp Glu
            755                 760                 765
Ser Lys Leu Lys Glu Tyr Thr Arg Tyr Lys Leu Lys Gly Phe Ile Glu
770                 775                 780
Ser Ser Gln Asp Leu Glu Ala Tyr Val Ile Arg Tyr Asp Ala Lys His
785                 790                 795                 800
Arg Thr Leu Asp Val Ser Asp Asn Leu Leu Pro Asp Ile Leu Pro Glu
                805                 810                 815
Asn Thr Cys Gly Glu Pro Asn Arg Cys Ala Ala Gln Gln Tyr Leu Asp
                820                 825                 830
Glu Asn Pro Ser Pro Glu Cys Ser Ser Met Gln Asp Gly Ile Leu Ser
            835                 840                 845
Asp Ser His Ser Phe Ser Leu Asn Ile Asp Thr Gly Ser Ile Asn His
            850                 855                 860
Asn Glu Asn Leu Gly Ile Trp Val Leu Phe Lys Ile Ser Thr Leu Glu
865                 870                 875                 880
Gly Tyr Ala Lys Phe Gly Asn Leu Glu Val Ile Glu Asp Gly Pro Val
                885                 890                 895
Ile Gly Glu Ala Leu Ala Arg Val Lys Arg Gln Glu Thr Lys Trp Arg
            900                 905                 910
Asn Lys Leu Ala Gln Leu Thr Thr Glu Thr Gln Ala Ile Tyr Thr Arg
            915                 920                 925
Ala Lys Gln Ala Leu Asp Asn Leu Phe Ala Asn Ala Gln Asp Ser His
            930                 935                 940
Leu Lys Arg Asp Val Thr Phe Ala Glu Ile Ala Ala Arg Lys Ile
945                 950                 955                 960
Val Gln Ser Ile Arg Glu Ala Tyr Met Ser Trp Leu Ser Val Val Pro
                965                 970                 975
Gly Val Asn His Pro Ile Phe Thr Glu Leu Ser Gly Arg Val Gln Arg
            980                 985                 990
Ala Phe Gln Leu Tyr Asp Val Arg Asn Val Val Arg Asn Gly Arg Phe
```

-continued

```
                995              1000            1005
Leu Asn Gly Leu Ser Asp Trp Ile Val Thr Ser Asp Val Lys Val Gln
        1010            1015            1020

Glu Glu Asn Gly Asn Asn Val Leu Val Leu Asn Asn Trp Asp Ala Gln
1025            1030            1035            1040

Val Leu Gln Asn Val Lys Leu Tyr Gln Asp Arg Gly Tyr Ile Leu His
            1045            1050            1055

Val Thr Ala Arg Lys Ile Gly Ile Gly Glu Gly Tyr Ile Thr Ile Thr
            1060            1065            1070

Asp Glu Glu Gly His Thr Asp Gln Leu Arg Phe Thr Ala Cys Glu Glu
        1075            1080            1085

Ile Asp Ala Ser Asn Ala Phe Ile Ser Gly Tyr Ile Thr Lys Glu Leu
    1090            1095            1100

Glu Phe Phe Pro Asp Thr Glu Lys Val His Ile Glu Ile Gly Glu Thr
1105            1110            1115            1120

Glu Gly Ile Phe Leu Val Glu Ser Ile Glu Leu Phe Leu Met Glu Glu
            1125            1130            1135

Leu Cys
```

VARIANT AXMI-R1 DELTA ENDOTOXIN GENES AND METHODS FOR THEIR USE

CROSS REFERENCE TO RELATED APPLICATION

This application claims the benefit of U.S. Provisional Application Ser. No. 61/150,309, filed Feb. 5, 2009, and 61/229,567, filed Jul. 29, 2009, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "384124_SequenceListing.txt", created on Feb. 3, 2010, and having a size of 384 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* (Bt) is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Cry3 type delta endotoxins were first identified in the early 1980's. Cry3Aa1 delta endotoxin (also previously known as cryC and cryIIIA) has been previously isolated from strains *Bacillus thuringiensis* var *san diego* (Herrnstadt et al. (1987) Gene. 57:37-46), *Bacillus thuringiensis tenebrionis* (Hofte et al. (1987) Nucleic acids Res. 15: 7183; McPherson et al. (1988) Bio/Technology 6:61-66; Sekar et al. (1987) Proc. Natl. Acad. Sci. USA 84: 7036-7040) and EG2158 (Donovan et al. (1988) Mol Gen Genet. 214(3):365-72).

Cry3Aa is often observed as a major component of a rhomboid crystal in certain native *Bacillus* strains, and is produced as a 72 kDa protein that is subsequently processed to a 66 kDa toxin by proteolytic processing by sporulation associated proteases. This 66 kDA protein has been known to produce activity on the coleopteran Colorado Potato Beetle.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules are provided that encode a pesticidal protein. Additionally, amino acid sequences corresponding to the pesticidal protein are encompassed. In particular, the present invention provides for an isolated nucleic acid molecule comprising a nucleotide sequence encoding a variant CRY3. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

The following embodiments are encompassed by the present invention:

1. A recombinant nucleic acid molecule comprising a nucleotide sequence encoding a variant Cry3 amino acid sequence, wherein said variant comprises one or more amino acid substitutions corresponding to the amino acid substitutions listed in Table 16, and wherein said variant has pesticidal activity.

2. The recombinant nucleic acid molecule of embodiment 1, wherein the pesticidal activity of said variant is improved relative to the pesticidal activity of SEQ ID NO:2.

3. The recombinant nucleic acid molecule of embodiment 1, wherein said pesticidal activity is against a coleopteran pest.

4. The recombinant nucleic acid molecule of embodiment 3, wherein said pesticidal activity is against a rootworm pest.

5. The recombinant nucleic acid molecule of embodiment 4, wherein said rootworm is Western corn rootworm or Southern corn rootworm.

6. The recombinant nucleic acid molecule of embodiment 1, wherein said nucleotide sequence is a synthetic sequence that has been designed for expression in a plant.

7. The recombinant nucleic acid molecule of embodiment 1, wherein said nucleotide sequence is operably linked to a promoter capable of directing expression of said nucleotide sequence in a plant cell.

8. A vector comprising the nucleic acid molecule of embodiment 1.

9. The vector of embodiment 8, further comprising a nucleic acid molecule encoding a heterologous polypeptide.

10. A host cell comprising the vector of claim 8.

11. The host cell of embodiment 10 that is a bacterial host cell.

12. The host cell of embodiment 10 that is a plant host cell.

13. A transgenic plant comprising the host cell of embodiment 12.

14. The transgenic plant of embodiment 13, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

15. A seed comprising the nucleic acid molecule of embodiment 1.

16. A recombinant polypeptide comprising a variant Cry3 amino acid sequence, wherein said variant comprises one or more amino acid substitutions corresponding to the amino acid substitutions listed in Table 16, and wherein said variant has pesticidal activity.

17. The recombinant polypeptide of embodiment 16, wherein the pesticidal activity of said variant is improved relative to the pesticidal activity of SEQ ID NO:2.

18. The recombinant polypeptide of embodiment 16, wherein said pesticidal activity is against a coleopteran pest.

19. The recombinant polypeptide of embodiment 18, wherein said pesticidal activity is against a rootworm pest.

20. The recombinant polypeptide of embodiment 19, wherein said rootworm is Western corn rootworm or Southern corn rootworm.

21. The polypeptide of embodiment 16 further comprising heterologous amino acid sequences.

22. A composition comprising the polypeptide of embodiment 16.

23. The composition of embodiment 22, wherein said composition is selected from the group consisting of a powder, dust, pellet, granule, spray, emulsion, colloid, and solution.

24. The composition of embodiment 22, wherein said composition is prepared by desiccation, lyophilization, homogenization, extraction, filtration, centrifugation, sedimentation, or concentration of a culture of *Bacillus thuringiensis* cells.

25. The composition of embodiment 22, comprising from about 1% to about 99% by weight of said polypeptide.

26. A method for controlling a coleopteran pest population comprising contacting said population with a pesticidally-effective amount of the polypeptide of embodiment 16.

27. A method for killing a coleopteran pest comprising contacting said pest with, or feeding to said pest, a pesticidally-effective amount of the polypeptide of embodiment 16.

28. A method for producing a polypeptide with pesticidal activity toward a coleopteran pest, comprising culturing a host cell comprising the vector of embodiment 7.

29. A plant having stably incorporated into its genome a DNA construct comprising nucleic acid molecule comprising a nucleotide sequence encoding a variant Cry3 amino acid sequence, wherein said variant comprises one or more amino acid substitutions corresponding to the amino acid substitutions listed in Table 16, and wherein said variant has pesticidal activity.

30. The plant of embodiment 29, wherein the pesticidal activity of said variant is improved relative to the pesticidal activity of SEQ ID NO:2.

31. The plant of embodiment 29, wherein said pesticidal activity is coleopteran activity.

32. The plant of embodiment 31, wherein said activity is against rootworm pests.

33. The plant of embodiment 32, wherein said rootworm is Western corn rootworm or Southern corn rootworm.

34. The plant of embodiment 29, wherein said plant is a plant cell.

35. A method for protecting a plant from a pest, comprising expressing in a plant or cell thereof a nucleotide sequence encoding a variant Cry3 amino acid sequence, wherein said variant comprises one or more amino acid substitutions corresponding to the amino acid substitutions listed in Table 16, and wherein said variant has pesticidal activity.

36. The recombinant nucleic acid molecule of embodiment 1, wherein the pesticidal activity of said variant is improved relative to the pesticidal activity of SEQ ID NO:2.

BRIEF DESCRIPTION OF THE FIGURES

FIG. 1 shows the annotated AXMI-R1 sequence (SEQ ID NO:2). The underlined regions represent loop regions (L1, L2 and L3). The vertical bars represent the boundaries between domain I (DI), domain II (DII), and domain III (DIII). The arrows note some of the regions targeted for generation of variants.

FIG. 2 shows an alignment of Axmi164 (SEQ ID NO:44), Axmi161 (SEQ ID NO:45), Axmi152 (SEQ ID NO:46), Axmi151 (SEQ ID NO:47), Axmi146 (SEQ ID NO:48), Axmi141 (SEQ ID NO:49), Axmi129 (SEQ ID NO:50), Axmi128 (SEQ ID NO:51), Axmi127 (SEQ ID NO:52), Axmi120 (SEQ ID NO:53), Axmi116 (SEQ ID NO:54), Axmi114 (SEQ ID NO:55), Axmi101 (SEQ ID NO:56), Axmi091 (SEQ ID NO:57), Axmi087 (SEQ ID NO:58), Axmi037 (SEQ ID NO:59), Axmi029 (SEQ ID NO:60), Axmi028 (SEQ ID NO:61), Cry8Bb1 (SEQ ID NO:62), Cry8Bc1 (SEQ ID NO:63), Cry7Aa (SEQ ID NO:64), AxmiR1 PermutP3c7 (evo21]]) (SEQ ID NO:13), and Axmi-R1 (SEQ ID NO:2).

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided.

Provided herein are compositions comprising nucleic acid sequences encoding variant Cry3 amino acid sequences wherein the variant has pesticidal activity, particularly pesticidal activity against coleopteran pests. By "variant Cry3" amino acid sequence is intended a Cry3 sequence other than a naturally-occurring Cry3 amino acid sequence wherein the amino acid sequence has one or more amino acid substitutions corresponding to the substitutions set forth in Table 16. For a list of Cry3 sequences, see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil Crickmore/Bt/index.

In some embodiments, the naturally-occurring, or "wild-type," Cry3 sequence is the Axmi-R1 nucleotide sequence set forth in SEQ ID NO:1, which encodes the amino acid sequence set forth in SEQ ID NO:2. The AXMI-R1 sequence corresponds to the cry3Aa sequence described in GEN-BANK® Accession No. P0A379. However, it will be understood that the substitutions described in Table 16 can be made at corresponding positions of any Cry3 protein, such as any Cry3A, Cry3B, or Cry3C protein. The "corresponding positions" can be determined by aligning the target sequence with SEQ ID NO:2. See, for example, the alignment shown in FIG. 2.

The crystal structure of the cry3Aa protein has been determined previously (Li et al, 1991, Nature 353:815-821). This crystal structure delineates the various loop regions, and shows sites of proteolytic processing relative to the three dimensional structure of the protein. This structure suggests that the toxin is arranged into three domains consistent with the structures of other delta-endotoxin sequences (typically referred to as Domains I, II, and III). Each domain of the toxin has loop regions that are defined based on the crystal structure. Prior to and since the publication of this crystal structure, there have been multiple attempts to describe broad simple rules related to the structure and function of toxicity of Bt endotoxins, and in particular the cry3-type endotoxins, and the role of proteolysis in this activity.

For example, Van Rie et al., 1997 (U.S. Pat. No. 5,659,123) suggest the identification of amino acids leading to improved toxicity by performing modifications of Domain II in the areas regarded as "loops" by identifying positions negatively impacting toxicity, followed by random replacement of amino acids at certain positions within these loops. Similarly, random alanine insertion into Loop II residues by Wu and Dean (J. Mol. Biol., 1996, 255: 628-640) reduced protein function. Random mutagenesis of Loop I residues by Wu et al (Febs Letters, 2000, 473:227-232) in most cases resulted in unstable protein and reduced protein function, and in two cases was reported to yield proteins with increased toxicity and altered binding properties. For the cry3Bb toxin (English et al, U.S. Pat. No. 6,023,013 re-issued as RE39,580) it was reported that certain substitutions in that toxin led to improved corn rootworm activity, but in most cases these alterations occurred in different residues than those suggested by Van Rie, or studied by Wu and Dean. In addition, modifications in the regions of the cry3A toxin that are normally cleaved by trypsin- or chymotrypsin-like proteases have been made in attempts to improve cry3A activity on coleopteran and notably western corn rootworm. Chen et al (U.S. Pat. No. 7,030,295) report that insertion of the synthetic tetrapeptide AAPF (SEQ ID NO:20), described as a "Cathepsin G cleavage site" (or a "chymotrypsin/Cathepsin G cleavage site"; Walters et al, 2008, Applied and Environ. Micro. 74: 367-374), at specific locations in the protein can lead to improved cry3A activity.

Trypsin cleavage of cry3A is well known in the art, and has been shown to naturally occur in the region of approximately R158-N159 in the native cry3A peptide (Carroll et al 1989 Biochem J. 261:99-105). Furthermore, chymotrypsin is also known to cleave in this region at the His161-Ser162 junction (Carroll et al 1997 J Invert. Biol. 70: 41-49). Walters et al (2008) showed cleavage of a modified Cry3A ("mCry3A," which contains a chymotrypsin cathepsin G protease recognition site) by chymotrypsin at its native location in this region (the His161-Ser162 junction). There are no reports of mutagenesis of the naturally occurring amino acid sequence in this region of Cry 3A resulting in improved pesticidal activity on coleopteran pests.

Thus, the invention provides variant Cry3 sequences having improved pesticidal activity relative to the corresponding wild-type sequence. In various embodiments, the variant Cry3 pesticidal sequences have improved pesticidal activity compared to the pesticidal activity of AXMI-R1. By "improved activity" is intended an increase in the mortality, reduction in feeding, or reduction in growth of a target pest. The improvement in activity is at least about 5%, at least about 10%, at least about 20%, at least about 30%%, at least about 40%, at least about 50%, at least about 60%, at least about 70%, at least about 80%, at least about 90%, at least about 100%, at least about 1.5-fold, at least about 2-fold, at least about 3-fold, at least about 4-fold, or greater increase in activity relative to the activity of the wild-type sequence, e.g., AXMI-R1. In some embodiments, the target pest is a coleopteran pest.

In some embodiments, the pesticidal sequences encompassed herein comprise variants of the axmi-R1 sequence set forth in SEQ ID NO:1. By "variants of axmi-R1" is intended a nucleotide or amino acid sequence corresponding to AXMI-R1, where one or more mutations has been introduced within certain regions (i.e., "target mutation region(s)") of the AXMI-R1 sequence. Unless otherwise specified, the amino acid regions outside of the target mutation region(s) are identical to the AXMI-R1 sequence. The identical regions are either identical amino acid sequences, or a nucleotide sequence that encodes an identical amino acid sequence. It will be understood that nucleotide sequences may differ from the wild-type nucleotide sequence, yet still encode the wild-type amino acid sequence, due to the degeneracy of the genetic code.

In other embodiments, the target mutation region of Cry3 corresponds to the proposed processing and pore forming region described in Li et al. (1991, Nature 353:815-821, herein incorporated by reference in its entirety, particularly with respect to the structural descriptions of the cry3Aa protein). In various embodiments, the target mutation region corresponds to amino acid positions 480 to 490, and positions 510 to 530 of SEQ ID NO:2. In some embodiments, the variant Cry3 sequence contains one or more of the mutations described in Table 16, including any combination of the mutations listed in Table 16, up to and including mutation at every position described in Table 16.

In some embodiments, the variant Cry3 sequences of the invention have one or more substitutions selected from the amino acid positions corresponding to positions 158, 482, 483, and 519 of SEQ ID NO:2. In another embodiment, the variant Cry3 sequences do not have the following substitutions: P154H, V155H, R315W, R315D, R315M, R315L, G316K, G316N, G316V, or G316A. In yet another embodiment, the variant Cry3 sequence of the invention does not have any of the combination of mutations listed in Table 2 of U.S. Pat. No. 6,023,013.

In another embodiment, the variant Cry3 sequence is selected from the group consisting of SEQ ID NO:6, 8, 10, 13, 15, 17, 19, and 21-43. In yet another embodiment, the variant Cry3 sequences encompassed herein consist of one or more mutations in the processing and pore formation region and one or more mutations in the receptor binding region. The variants encompassed herein have improved pesticidal activity relative to the pesticidal activity of the wild-type Cry3. In some embodiments, the improved pesticidal activity is against a coleopteran pests, for example, a rootworm pest.

The variant Cry3 sequences of the invention can be further modified to introduce one or more of the Cry3 mutations described in the art. For example, the variant AXMI-R1 sequence encompassed herein can comprise one or more of the substitutions listed in Table 16 in addition to one or more of the mutations described in U.S. Pat. Nos. 5,659,123 and 6,023,013; Wu and Dean (J. Mol. Biol., 1996, 255: 628-640); or Wu et al (Febs Letters, 2000, 473:227-232), or any combination thereof. Additionally, the variant AXMI-R1 sequence may comprise an insertion of one or more Cathepsin G cleavage sites as discussed supra (e.g., at or near the native chymotrypsin or trypsin cleavage site).

In yet another embodiment of the invention, the mutations described in Table 16 can be introduced into the corresponding positions of any amino acid sequences having homology to AXMI-R1 to introduce or improve toxicity to a pest of interest, particularly a coleopteran pest such as a rootworm pest. See, for example, the amino acid sequences aligned with AXMI-R1 in FIG. 2, or the homologous amino acid sequences set forth in, for example, GENBANK® Accession No. P0A379.1, AAA22336.1, AAA22542.1, AAS79487.1, AAU29411.1, AAW82872.1, AAA73184.1, CAA51996.1, 1DLC_A, Q45744.1, Q06117.1, AAA74198.1, P17969.1. The homologous amino acid sequence can be aligned using one of the alignment programs described herein to identify the corresponding positions for mutation. Alternatively, a crystal structure or other 3-dimensional representation thereof of the homologous amino acid sequence can be superimposed onto the crystal structure of Cry3A (described in Li et al. 1991, Nature 353:815-821) and the corresponding positions aligned. The crystal structure of the Cry3B protein is described in U.S. Pat. No. 6,023,013.

The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling. The proteins find use in controlling or killing lepidopteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid sequence (or DNA) is used herein to refer to a nucleic acid sequence (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include nucleotide sequences encoding variants of Cry3, as well as fragments and complements thereof. By "complement" is intended a nucleotide sequence that is sufficiently complementary to a given nucleotide sequence such that it can hybridize to the given nucleotide sequence to thereby form a stable duplex.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. By "retains activity" is intended that the fragment will have at least about 30%, at least about 50%, at least about 70%, 80%, 90%, 95% or higher of the pesticidal activity of the reference pesticidal protein (i.e., the pesticidal variant Cry3 sequences disclosed herein). In one embodiment, the pesticidal activity is coleoptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have a N-terminal truncation of at least about 100 amino acids, about 120, about 130, about 140, about 150, or about 160 amino acids relative to SEQ ID NO:2. In various embodiments, the proteolytic cleavage fragment may correspond to the native trypsin or chymotrypsin cleavage site corresponding to amino acid positions 158-159 or positions 160-161 of SEQ ID NO:2, respectively, or may correspond to any artificially-inserted cleavage sites, such as the Cathepsin G cleavage site described in Walters et al, 2008, Applied and Environ. Micro. 74: 367-374.

Preferred pesticidal proteins of the present invention are encoded by a nucleotide sequence sufficiently identical to the variant Cry3 sequences encompassed herein. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence (e.g., a native or variant Cry3 sequence, including a native or variant Cry3A, Cry3B, or Cry3C sequence, or a sequence selected from SEQ ID NO:2, 6, 8, 10, 13, 15, 17, 19, and 21-43, or a nucleotide sequence encoding any of these native or variant Cry3 protein sequences) using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., variant Cry3 sequences encompassed herein). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal variant Cry3 protein-encoding nucleotide sequences include those sequences that encode the variant pesticidal proteins disclosed herein but that differ conservatively because of the degeneracy of the genetic code as well as those that are sufficiently identical as discussed above. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the reference protein (i.e., variant Cry3 sequences encompassed herein), that is, pesticidal activity. By "retains activity" is intended that the variant will have at least about 30%, at least about 50%, at least about 70%, or at least about 80% of the pesticidal activity of the reference protein. In some embodiments, the variant pesticidal proteins described herein show improved activity relative to the AXMI-R1 protein set forth in SEQ ID NO:2. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743, 477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the target mutation region(s) of the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the reference sequence of a pesticidal protein without substantially altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the target mutation region(s), such as by permutation or saturation mutagenesis, and the resultant mutants can be screened for ability to confer pesticidal activity to identify mutants that retain activity or show improved activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal protein sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended the pesticidal variant Cry3 sequences encompassed herein. Fragments, biologically active portions, and variants thereof are also provided, and may be used to practice the methods of the present invention. An “isolated protein” or a “recombinant protein” is used to refer to a protein that is no longer in its natural environment, for example in vitro or in a recombinant bacterial or plant host cell.

“Fragments” or “biologically active portions” include polypeptide fragments of the variant Cry3 sequences encompassed herein, and that exhibit pesticidal activity. A biologically active portion of a pesticidal protein can be a polypeptide that is, for example, 10, 25, 50, 100, 150, 200, 250 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743, 477, all of which are herein incorporated by reference in their entirety. As used here, a fragment comprises at least 8 contiguous amino acids of the reference protein. The invention encompasses other fragments, however, such as any fragment in the protein greater than about 10, 20, 30, 50, 100, 150, 200, 250, 300, 350, 400, 450, 500, 550, 600, 650, or more amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:2. Variants also include polypeptides encoded by a nucleic acid molecule that hybridizes to the nucleic acid molecule encoding the variant Cry3 sequences encompassed herein, or a complement thereof, under stringent conditions. Variants include polypeptides that differ in amino acid sequence due to mutagenesis. Variant proteins encompassed by the present invention are biologically active, that is they continue to possess the desired biological activity of the variant Cry3 protein, that is, retain pesticidal activity. In some embodiments, the variants have improved activity relative to the reference protein (e.g., relative to SEQ ID NO:2, or relative to a specific variant Cry3 protein). Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be further altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of the variant Cry3 sequences encompassed herein, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions in one or more of the target mutation region(s). Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired (or improved) pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968;

Romer et al. (1993) *Biochem. Biophys. Res. Commun.* 196: 1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the variant Cry3 sequences disclosed herein. In various embodiments, the transgenic plant further comprises one or more additional genes for insect resistance, for example, one or more additional genes for controlling coleopteran pests (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; Cry34/35; VIPs, such as VIP3; or any of the modified Cry3A or Cry3B sequences known in the art as having toxicity against coleopteran pests. It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, *macadamia*, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhopper; *Blissus leucopterus* leucopterus, chinch bug; *Acrosternum hilare*, green stink bug; Soybean: *Pseudoplusia includens*, soybean looper; *Anticarsia gemmatalis*, velvetbean caterpillar; *Plathypena scabs*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2 (5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides:
Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

Methods for Increasing Plant Yield

Methods for increasing plant yield are provided. The methods comprise introducing into a plant or plant cell a polynucleotide comprising a pesticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

The following examples are offered by way of illustration and not by way of limitation.

EXPERIMENTAL

EXAMPLE 1

Expression Construct pAX 5510 is an expression vector, based on the pRSF1b1 vector system (Invitrogen) that contains the open reading frame SEQ ID NO:1 (Designated herein as axmi-R1, which encodes the sequence described in GENBANK® Accession No. POA379) downstream of the T7 promoter, such that induction of transcription of the T7 promoter (for example, in BL21: DE3 strains) results in accumulation of the cry-R1 protein (SEQ ID NO:2, which corresponds to the sequence described in GENBANK® Accession No. POA379), with an N-terminal His tag, in *E. coli* cells.

EXAMPLE 2

Western Corn Rootworm (WCRW) and Southern Corn Rootworm (SCRW) Bioassays

Western and Southern corn rootworm eggs (*Diabrotica virgifera* and *Diabrotica undecimpunctata*, respectively) (Crop Characteristics, MN) were washed and incubated at 25° C. until near-hatch. Molten artificial diet was prepared as previously described (U.S. Pat. No. 7,351,881, herein incorporated by reference), placed in 1 ml aliquots and allowed to cool in 24-well tissue culture plates (Corning 3527) for 1 hour. Once solidified, 40 µA of sample was placed in each well and allowed to diffuse into the diet. After the sample was absorbed, 7.5 µl of egg: 0.15% agar slurry (approximately 25 rootworm eggs per well) were delivered onto the side of each well and allowed to dry. Once dry, the plates were sealed with a BREATHE-EASY® gas permeable membrane (Research Products International) and placed in a dark growth chamber (25° C., 90% relative humidity (RH)).

After 24 hours, each plate had its membrane and then unhatched eggs removed, resealed with gas permeable membranes and returned to the dark growth chamber (25° C., 90% RH) for an additional four days. After a total of five days, insects in sample wells were compared to in-plate controls and assessed for stunting and mortality (See Table 1 for the scoring system).

TABLE 1

Scoring System used in WCRW and SCRW Bioassays

| Score | Definition |
|---|---|
| 0 | No Activity |
| 1 | Slight, non-uniform stunt |
| 2 | Non-uniform stunt |
| 3 | Uniform stunt |
| 4 | Uniform stunt with mortality (expressed as a percentage) |
| 5 | Uniform stunt with 100% mortality |

EXAMPLE 3

Mutagenesis Strategy, and Creation of First Mutagenized Library

The first generation point mutation library (PM Library 1, PM1) targeted 4 regions of SEQ ID NO:2, comprising twenty eight (28) positions. Using pAX5510 as a template, several individual positions were randomized using the QUIKCHANGE® Site-directed mutagenesis kit, and the DNA sequences of a large number of variants were determined. By analysis of the DNA sequences, desirable variants were pooled, while undesired clones (such as wild-type clones, duplicate mutants and frame shift mutants) were eliminated. Two hundred and ninety-four (294) unique variants were identified from PM Library 1 for further testing.

Primary screening. The pooled library variants, as well as pAX5510, were transformed into BL21*DE3 cells and plated on LB+Kanamycin (100 μg/ml). Fresh colonies were picked into 8.5 ml LB+Kanamycin (100 ug/ml) liquid medium and were grown in 24 deep well blocks at 37° C. and 250 rpm until an OD600 nm of 0.3-0.4 was reached. IPTG was added to a final concentration of 0.5 mM and the cultures were incubated for an additional 18 hours at 20° C. The OD600 nm was determined and the cells were collected by centrifugation (10 minutes at 4500 rpm, 4 degrees C.). The cell pellets were resuspended in 50 mM Sodium carbonate pH 10.5, 1 mM DTT at a density of 10 OD600/ml. The cells were disrupted by bead beating and soluble extracts were obtained after centrifugation at 4000 rpm for 15 minutes at 4° C.

The extracts were assayed for activity against WCRW and SCRW at 4 replicates per variant each. After 5 days, rootworm toxicity scores were determined by averaging the scores from 4 replicates. Variants (436 total) were screened in this primary screen, providing a 1.5× coverage of the library.

Re-assays and scale-up. Forty-three variants scoring ≧3 in the primary screen were re-assayed using the same experimental conditions as in the primary screen. The scores obtained from primary screen and re-assay, including scores from repeat isolates due to oversampling, were averaged, and 20 variants were prioritized for more extensive scale-ups.

For scale-ups, 5 freshly transformed colonies were picked into 135 ml LB+Kanamycin (100 μg/ml) and grown in 1 liter shaker flasks at 37° C. and 250 rpm until an OD600 nm of 0.3-0.4 was reached. IPTG was added to a final concentration of 0.5 mM and the cultures were incubated for an additional 18 hours at 20° C. The OD600 nm was determined and the cells were collected by centrifugation (10 minutes at 5000 rpm, 4 degrees C.). The cell pellets were resuspended in 50 mM Sodium carbonate pH10.5, 1 mM DTT at a density of 10 OD600/ml. The cells were disrupted by bead beating and soluble extracts were obtained after centrifugation at 4000 rpm for 15 minutes at 4° C. AXMI-R1 variants in those extracts were quantitated on SDS-PAGE stained with Coomassie by comparing serial dilutions of extract to a BSA standard of known concentration. The concentrations of the AXMI-R1 variants studied were close, ranging from 0.13-0.22 μg/ul.

For assaying, serial dilutions of extracts containing AXMI-R1 variant were prepared in a control extract from BL21*DE3 transformed with pRSF1b. The dilutions range from 40 to 1.25 μl of extract containing AXMI-R1 variants. Thus, the concentration of AXMI-R1 variants was titrated, while the amount of BL21#DE3 proteins was held constant. Forty replicates per variant and dilution were assayed on WCRW. The average score for each dilution was determined, as well as the EC50.

The AXMI-R1 variants were ranked according to the average bioassay score (n=40) at 40 μl of extract (Table 2). For comparison, 6 biological replicates of AXMI-R1 wild-type (wt) were prepared, and the data and standard deviations are provided. Variants D4F11, H9, G5, H4, D5D8, and D4A2 showed a significantly improved activity against WCRW. The nucleotide sequence encoding D5D8 is set forth in SEQ ID NO:5, and the amino acid sequence is set forth in SEQ ID NO:6.

TABLE 2

Variants with Improved Activity on WCRW.

| Amino acid Position relative to SEQ ID NO: 2 | Variant Protein ID | Amino Acid Change |
|---|---|---|
| 154 | D4F11 | P154A |
| 160 | H9 | P160I |
| 160 | G5 | P160A |
| 160 | H4 | P160F |
| 316 | D5D8 | G316T |
| 316 | D4A2 | G316Q |

Thus, while not bound by any particular theory or mechanism, improved WCRW activity may be linked to mutations in three positions of AXMI-R1 (Table 2). Positions 154 and 160 of AXMI-R1 are in the proposed processing and pore formation region, while position 316 is in the proposed receptor binding region (Li et al, 1991, Nature 353:815-821).

EXAMPLE 4

Combination Variants

Variants were generated that combine favorable mutations at position 316 with favorable mutations at positions 154 and 160 to identify combinations of mutations providing cumulative improvements of processing and receptor recognition. Table 3 lists the results of such testing; the bioassay data indicate that the combination mutants P160I; G316T (H9+D5D8) and P160F; G316T (H4+D5D8) provide cumulative improvements in activity. The nucleotide sequence encoding H9+D5D8 is set forth in SEQ ID NO:7, and the amino acid sequence is set forth in SEQ ID NO:8. The amino acid sequence for H4+D5D8 is set forth in SEQ ID NO:26.

TABLE 3

| | Score | | | | | | AVG | Std Dev |
|---|---|---|---|---|---|---|---|---|
| | 0 | 1 | 2 | 3 | 4 | 5 | | |
| Activity of Combined Variants on SCRW | | | | | | | | |
| AXMI-R1 | 2 | 12 | 6 | 0 | 0 | 0 | 1.2 | 0.62 |
| H4 | 0 | 0 | 12 | 8 | 0 | 0 | 2.4 | 0.5 |
| H9 | 0 | 0 | 16 | 4 | 0 | 0 | 2.2 | 0.41 |
| G5 | 0 | 0 | 13 | 7 | 0 | 0 | 2.35 | 0.49 |
| D4F11 | 0 | 0 | 18 | 2 | 0 | 0 | 2.1 | 0.31 |
| D5D8 | 0 | 0 | 13 | 7 | 0 | 0 | 2.35 | 0.49 |
| D4A2 | 0 | 0 | 16 | 4 | 0 | 0 | 2.2 | 0.41 |
| H9 + D5D8 | 0 | 0 | 2 | 15 | 3 | 0 | 3.05 | 0.51 |
| H4 + D5D8 | 0 | 0 | 3 | 17 | 0 | 0 | 2.85 | 0.37 |
| G5 + D5D8 | 0 | 0 | 14 | 6 | 0 | 0 | 2.3 | 0.47 |
| D4F11 + D5D8 | 0 | 0 | 18 | 2 | 0 | 0 | 2.1 | 0.31 |
| H9 + D4A2 | 0 | 1 | 10 | 9 | 0 | 0 | 2.4 | 0.6 |
| H4 + D4A2 | 0 | 0 | 17 | 3 | 0 | 0 | 2.15 | 0.37 |
| G5 + D4A2 | 0 | 0 | 8 | 12 | 0 | 0 | 2.6 | 0.5 |
| D4F11 + D4A2 | 0 | 0 | 18 | 2 | 0 | 0 | 2.1 | 0.31 |
| Vector | 20 | 0 | 0 | 0 | 0 | 0 | 0 | 0 |
| Activity of Combined Variants on WCRW | | | | | | | | |
| AXMI-R1 | 0 | 3 | 37 | 0 | 0 | 0 | 1.93 | 0.27 |
| H4 | 0 | 0 | 33 | 7 | 0 | 0 | 2.18 | 0.38 |
| H9 | 0 | 0 | 40 | 0 | 0 | 0 | 2.00 | 0.00 |
| G5 | 0 | 0 | 35 | 5 | 0 | 0 | 2.13 | 0.33 |
| D4F11 | 0 | 0 | 40 | 0 | 0 | 0 | 2.00 | 0.00 |
| D5D8 | 0 | 0 | 40 | 0 | 0 | 0 | 2.00 | 0.00 |
| D4A2 | 0 | 0 | 40 | 0 | 0 | 0 | 2.00 | 0.00 |
| H9 + D5D8 | 0 | 0 | 40 | 0 | 0 | 0 | 2.00 | 0.00 |
| H4 + D5D8 | 0 | 0 | 39 | 1 | 0 | 0 | 2.03 | 0.16 |
| G5 + D5D8 | 0 | 0 | 40 | 0 | 0 | 0 | 2.00 | 0.00 |
| D4F11 + D5D8 | 0 | 0 | 34 | 0 | 0 | 0 | 1.85 | 0.36 |
| H9 + D4A2 | 0 | 0 | 40 | 0 | 0 | 0 | 2.00 | 0.00 |
| H4 + D4A2 | 0 | 32 | 7 | 0 | 0 | 0 | 1.18 | 0.39 |
| G5 + D4A2 | 0 | 16 | 24 | 0 | 0 | 0 | 1.60 | 0.50 |
| D4F11 + D4A2 | 0 | 18 | 21 | 0 | 0 | 0 | 1.54 | 0.51 |
| Vector | 20 | 0 | 0 | 0 | 0 | 0 | 0.0 | 0.00 |

EXAMPLE 5

Point Mutant Library 2: Residues Flanking Position 316

Given the improved pesticidal activity generated in PM Library 1 (PM1) from mutations in residue 316, a second point mutation library (PM library 2, PM2) was generated for positions 313, 314, 315, 317, and 318 relative to SEQ ID NO:2. This library has a calculated diversity of 61 variants. Ninety two (92) variants were assayed, and five variants (R315F, R315M, R315W, Y317E, Y317N) flanking position 316 showed some improvement in the primary screen. Variants R315M and R315W were scaled up and assayed at protein concentrations in the range of 125-250 μg/ml. The data indicates that alterations of position 315 can generate improved activity against CRW.

TABLE 4

WCRW

| Score | pAX5510 (AXMI-R1) | L3F1 (R315M) | L3G2 (R315W) | pRSF1b (control) |
|---|---|---|---|---|
| Activity of Variants on WCRW | | | | |
| 0 | 0 | 0 | 0 | 20 |
| 1 | 0 | 0 | 0 | 0 |
| 2 | 32 | 30 | 31 | 0 |
| 3 | 8 | 9 | 9 | 0 |
| 4 | 0 | 0 | 0 | 0 |
| 5 | 0 | 0 | 0 | 0 |
| AVG | 2.20 | 2.23 | 2.23 | 0 |
| Std Dev | 0.41 | 0.43 | 0.42 | 0 |
| Activity of Variants on SCRW | | | | |
| 0 | 0 | 0 | 0 | 17 |
| 1 | 0 | 0 | 0 | 0 |
| 2 | 14 | 2 | 0 | 3 |
| 3 | 6 | 15 | 16 | 0 |
| 4 | 0 | 3 | 4 | 0 |
| 5 | 0 | 0 | 0 | 0 |
| AVG | 2.30 | 3.05 | 3.20 | 0.30 |

Frequency of Score (0-5)

EXAMPLE 6

Permutational Library 1

A permutational mutagenesis library was generated targeting positions 154, 155, 158 and 160. This library (Library P1; P1) was generated using oligo-directed mutagenesis methods as known in the art, resulting in a library with a theoretical complexity of 768 variants. The diversity incorporated in the library is as follows:

TABLE 5

Positions altered in Library 2.

| Position relative to SEQ ID NO: 2 | Amino Acids Observed in Variants | Amino Acid Changes in Library (P1) |
|---|---|---|
| 154 | P, A, E | P, A, E, D, H, Q |
| 155 | V, E, K | V, E, K, M |
| 158 | R, V | R, V, G, L |
| 160 | P, A, F, I | P, A, F, I, L, S, T, V |

Five hundred seventy three (573) clones were analyzed in a 24 well format (4 reps each), and 155 clones were identified for further testing. Seventy-three clones were re-tested, and ultimately eight clones were tested after scale up (as described herein).

EXAMPLE 7

Mortality of Variants on WCRW and SCRW

Several variants from P1 showing desired activity were selected for scale up experiments as described herein. The resulting protein was tested at protein concentrations in the range of 125-250 μg/ml. Several variants showed the ability to kill WCRW and SCRW in these assays, whereas control protein AXMI-R1 wt showed no mortality on either WCRW or SCRW in these assays.

In a first set of experiments, CRW eggs were deposited into wells, samples were added, and, after 5 days, damage to CRW and % CRW mortality (if applicable) were scored (Table 6).

The average scores and average mortality were based on 40 replicates for WCRW and 20 replicates for SCRW. The data showed that variants PermutP3c6 and PermutP3c7 give 8-9% mortality against WCRW and 60-80% mortality against SCRW, while the AXMI-R1 wt showed no mortality (Table 7). The nucleotide sequence encoding the 3c7 variant is set forth in SEQ ID NO:12, and the amino acid sequence is set forth in SEQ ID NO:13.

Analysis of the proteins by SDS-PAGE shows that the expression levels of AXMI-R1 wt, 3c6, and 3c7 are indistinguishable and likely identical.

TABLE 6

Activity of Variants on Corn Rootworm

| | Score: Western Corn Rootworm | | Score: Southern Corn Rootworm | |
|---|---|---|---|---|
| | Avg score (n = 40) | SD | Avg score (n = 20) | SD |
| Vector Control | 0.00 | 0.00 | 0.25 | 0.44 |
| AXMI-R1 | 2.50 | 0.51 | 2.65 | 0.49 |
| 3c6 | 3.03 | 0.62 | 4.70 | 0.57 |
| 3c7 | 3.03 | 0.62 | 4.10 | 0.85 |

TABLE 7

Mortality of Variants on Corn Rootworm

| | Mortality: Western Corn Rootworm | | Mortality: Southern Corn Rootworm | |
|---|---|---|---|---|
| | Percent Mortality (n = 40) | SD | Percent Mortality (n = 20) | SD |
| Vector Control | 0.00 | 0.00 | 0.00 | 0.00 |
| AXMI-R1 | 0.00 | 0.00 | 0.00 | 0.00 |
| 3c6 | 8.75 | 18.72 | 86.50 | 29.07 |
| 3c7 | 7.75 | 17.02 | 59.00 | 38.78 |

In a subsequent experiment, CRW eggs were deposited into wells, sample was added, and after 1 day unhatched eggs were removed. This method gives a more synchronized population of early hatching CRW larvae that encounter the sample within 1-2 days of sample application. Under these conditions, variant 3c7 achieved 44% mortality against WCRW and 86% mortality against SCRW (Table 8).

TABLE 8

Mortality of Variant PermutP3c7 in modified Corn Rootworm assay

| | Mortality: Western Corn Rootworm | | Mortality: Southern Corn Rootworm | |
|---|---|---|---|---|
| | Percent Mortality (n = 40) | SD | Percent Mortality (n = 20) | SD |
| Vector Control | 0.00 | 0.00 | 0.00 | 0.00 |
| 3c7 | 44.00 | 26.44 | 86.50 | 13.09 |

A third variant, 3a11 (V155K; R158G; P160T), also induced mortality against WCRW compared to the AXMI-R1 controls. In this experiment, CRW eggs were deposited into wells, sample was added, and after 1 day unhatched eggs were removed. Mortality of 36% was observed in rootworms exposed to 3a11 in this assay (Table 9).

TABLE 9

Activity of Variants 3a11 on Corn Rootworm

| | Western Corn Rootworm | |
|---|---|---|
| | Avg score (n = 40) | SD |
| Vector Control | 0.05 | 0.22 |
| AXMI-R1 | 2.45 | 0.71 |
| 3a11 | 3.8 | 0.69 |

TABLE 10

Summary of Amino Acid changes of certain variants

| Protein ID | Amino Acid Changes relative to SEQ ID NO: 2 |
|---|---|
| 3c7 | P154A; V155K; P160V |
| 3c6 | P154Q; V155E; P160L |
| 3a11 | V155K; R158G; P160T |

EXAMPLE 8

Combinatorial Variants

A variant that combined 3c7 (P154A, V155K, P160V) and the variant D5D8 (G316T) from Library PM 1 was generated and tested for CRW activity, and showed mortality against WCRW and SCRW at protein concentrations in the range of 125-250 μg/ml. The nucleotide sequence encoding the 3c7+ D5D8 variant is set forth in SEQ ID NO:9, and the amino acid sequence is set forth in SEQ ID NO:10.

EXAMPLE 9

Library PM2

A second generation point mutation library (PM2) was generated to combine alterations in positions 482 and 483 with alterations in positions 315 and 316. This library contains 756 variants. More than 1,100 clones were picked and tested for activity. Variants '1g8' (G316E, Q482L, G483K) and '2b11' (G316A, Q482L, G483K) were found to show improved activity on a rootworm pest compared to AXMI-R1. Variant 1g8 showed in most cases superior activity compared to 3c7. The nucleotide sequence encoding the 1g8 variant is set forth in SEQ ID NO:14, and the amino acid sequence is set forth in SEQ ID NO:15.

TABLE 11

Percentage of wells with 50% or greater mortality

| | WCRW | SCRW |
|---|---|---|
| AXMI-R1 (pAX5510) | 0 | 0 |
| 3c7 | 56 | 13 |
| 1g8 | 100 | 50 |
| Vector Control | 6 | 0 |

EXAMPLE 10

Library P3

A library (Library P3) of variants in the positions corresponding to positions 481 through 486 of AXMI-R1 (designated herein as 'Loop 3') was generated. Individual clones were tested to assess the contribution of each residue to pesticidal activity. Residues 482 and 483 were found to contribute to activity, since variants in these residues demonstrated improved activity on corn rootworm (Table 12).

TABLE 12

Improved Variants from Residues 482 and 483

| AA change relative to SEQ ID NO: 2 | | WCRW (score) | SCRW (score) |
|---|---|---|---|
| None | Test 1 | 1 | 0 |
| | Test 2 | 2 | 0 |
| | Test 3 | 2 | 2 |
| Q482I | Test 1 | 4 | 2 |
| | Test 2 | 3 | 2 |
| G483K | Test 1 | 4 | 3 |
| | Test 2 | 4 | 4 |
| G483S | Test 1 | 3 | 1 |
| | Test 2 | 4 | 3 |
| G438Q | Test 1 | 2 | 3 |
| | Test 2 | 4 | 3 |

EXAMPLE 11

Combination Variants

Clones were generated that combined the alterations observed in variants 1g8 and 2b11 with that in 3c7. The resulting clones AXMI-R1 (3c7+1g8) and AXMI-R1 (3c7+2b11) were tested and found to retain activity on corn rootworm. Notably, AXMI-R1 (3c7+1g8) appeared to exhibit higher mortality on corn rootworm than 3c7 alone. AXMI-R1 (3c7+2b11) also appeared in some tests to exhibit activity greater than 3c7 alone.

EXAMPLE 12

Generation of AXMI-R1 (EVO23)

A second generation permutational library for the processing region was cloned into AXMI-R1 (1g8) (SEQ ID NO:15), thus allowing a diversity screen in the processing region in the context of variant AXMI-R1 (1g8), which contains mutations in the receptor binding region. The diversity of that library is 573. Variants (n=813) were screened, 163 clones were re-assayed, and 40 variants were scaled up. AXMI-R1 (EVO23) (SEQ ID NO:17) had the highest activity from that library. The nucleotide sequence encoding AXMI-R1 (EVO23) is set forth in SEQ ID NO:16. The activity of EVO23 on WCRW is shown in Table 13.

TABLE 13

Activity of EVO23 on Western Corn Rootworm

| | WCRW avg mortality (%) | std dev |
|---|---|---|
| AXMI-R1 | 1.67 | 3.79 |
| Evo23 | 23.44 | 6.15 |
| pRSF1b | 0.20 | 0.78 |

EXAMPLE 13

Generation of Domain II/III Interface Variants

Modeling of axmi-R1 has identified 3 regions contributing to the interface between domain 2 and domain 3. These regions correspond to positions 331-335, positions 368-373, and positions 518-524 of SEQ ID NO:2. Variant libraries targeting these regions were generated. The diversity of the library corresponding to positions 518-524 was eight (Table 14). Twelve variants were screened, and L61E11 was re-assayed and scaled up.

TABLE 14

Domain II/III interface variant library

| position | 518 | 519 | 520 | 521 | 522 | 523 | 524 |
|---|---|---|---|---|---|---|---|
| wt | Y | K | L | Q | S | G | A |
| diversity | | S | | K | | | |
| codons | tat | aag agt | tta | caa aaa | tct | ggt | gct |
| permut dna | tat | ark | tta | maa | tct | ggt | gct |
| permut prot | Y | KSRN | L | QK | S | G | A |

The activity of the L61E11 variant against WCRW is show in Table 15.

TABLE 15

Activity of L61E11 on Western Corn Rootworm

| | WCRW avg mortality (%) | Stdv |
|---|---|---|
| AXMI-R1 | 13 | 14.2 |
| L61e11 | 18 | 14.5 |
| pRSF1b | 0 | 0 |

The present invention demonstrates that alteration of the residues described herein result in variants with improved activity on pests. A summary of the residues that were altered in the present invention is provided in Table 16.

TABLE 16

Summary of Positions Altered in Improved Variants

| SEQ ID NO: | Identifier | Summary of mutations | 154 | 155 | 158 | 160 | 315 | 316 | 482 | 483 | 519 |
|---|---|---|---|---|---|---|---|---|---|---|---|
| 2 | wt | wt | P | V | R | P | R | G | Q | G | K |
| 21 | D4F11 | P154A | A | | | | | | | | |
| 22 | H9 | P160I | | | | I | | | | | |
| 23 | G5 | P160A | | | | A | | | | | |
| 24 | H4 | P160F | | | | F | | | | | |
| 6 | D5D8 | G316T | | | | | | T | | | |
| 25 | D4A2 | G316Q | | | | | | Q | | | |
| 8 | H9 + D5D8 | P160I; G316T | | | | I | | T | | | |
| 26 | H4 + D5D8 | P160F; G316T | | | | F | | T | | | |
| 27 | H9 + D4A2 | P160I; G316Q | | | | I | | Q | | | |
| 28 | G5 + D4A2 | P160A; G316Q | | | | A | | Q | | | |
| 29 | R315M | R315M | | | | | M | | | | |
| 30 | R315W | R315W | | | | | W | | | | |
| 31 | 3c6 | P154Q; V155E; P160L | Q | E | | L | | | | | |
| 13 | 3c7 | P154A; V155K; P160V | A | K | | V | | | | | |
| 32 | 3a11 | V155K; R158G; P160T | | K | G | T | | | | | |

TABLE 16-continued

Summary of Positions Altered in Improved Variants

| SEQ ID NO: | Identifier | Summary of mutations | 154 | 155 | 158 | 160 | 315 | 316 | 482 | 483 | 519 |
|---|---|---|---|---|---|---|---|---|---|---|---|
| 15 | 1g8 | G316E; Q482L; G483K | | | | | | E | L | K | |
| 33 | 2b11 | G316A; Q482L; G483K | | | | | | A | L | K | |
| 34 | Q482I | Q482I | | | | | | | I | | |
| 35 | G483K | G483K | | | | | | | | K | |
| 36 | G483S | G483S | | | | | | | | S | |
| 37 | G483Q | G483Q | | | | | | | | Q | |
| 38 | 3c7 + 1g8 | P154A; V155K; P160V; G316E; Q482L; G483K | A | K | | V | | E | L | K | |
| 39 | 3c7 + 2b11 | P154A; V155K; P160V; G316A; Q482L; G483K | A | K | | V | | A | L | K | |
| 17 | Evo23 | P154H; P160L; G316E; Q482L; G483K | H | | | L | | E | L | K | |
| 19 | L61E11 | K519N | | | | | | | | | N |
| 10 | 3c7 + D5D8 (Evo20) | P154A; V155K; P160V; G316T | A | K | | V | | T | | | |
| 40 | G5 + D5D8 | P160A; G316T | | | | A | | T | | | |
| 41 | D4F11 + D5D8 | P154A; G316T | A | | | | | T | | | |
| 42 | H4 + D4A2 | P160F; G316Q | | | | F | | Q | | | |
| 43 | D4F11 + D4A2 | P154A; G316Q | A | | | | | Q | | | |

EXAMPLE 14

Use of Evolved AXMI-R1 Sequences in Other Cry Proteins

AXMI-R1 sequence segments containing favorable mutations could be inserted into other, homologous Cry proteins to improve processing, receptor binding and activity. For example, a sequence segment from an evolved AXMI-R1 variant covering the processing region could be used to replace the homologous region in axmi008, axmi028, and other Cry proteins. Since the 3D folding of Cry proteins is conserved, improved processing and potency of the hybrid protein may be achieved. Further mutagenesis of these AXMI-R1 variant sequences may help to adapt and improve the AXMI-R1 variant sequences in the context of the host proteins.

EXAMPLE 15

Additional Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

EXAMPLE 16

Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent sequence.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:11) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

EXAMPLE 17

Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials
DN62A5S Media

| Components | Per Liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

EXAMPLE 18

Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant polypeptide comprising a variant Cry3 amino acid sequence, wherein said variant comprises one or more amino acid substitutions in the amino acid sequence of SEQ ID NO:2, and wherein the one or more amino acid substitutions are selected from the group consisting of:
   a) an alanine, glutamine, or histidine residue at the position 154 of SEQ ID NO:2;
   b) a glutamic acid or a lysine residue at the position 155 of SEQ ID NO:2;
   c) a glycine residue at the position 158 of SEQ ID NO:2;
   d) an alanine, isoleucine, leucine, phenylalanine, threonine, or valine residue at the position 160 of SEQ ID NO:2;
   e) a methionine or tryptophan residue at the position 315 of SEQ ID NO:2;
   f) an alanine, glutamine, glutamic acid, or threonine residue at the position 316 of SEQ ID NO:2;
   g) an isoleucine or leucine residue at the position 482 of SEQ ID NO:2;
   h) a glutamine, lysine, or serine residue at the position 483 of SEQ ID NO:2; and
   i) an asparagine residue at the position 519 of SEQ ID NO:2; and wherein said variant has pesticidal activity.

2. The recombinant polypeptide of claim 1, wherein the pesticidal activity of said variant is improved relative to the pesticidal activity of SEQ ID NO:2.

3. The recombinant polypeptide of claim 1, wherein said pesticidal activity is against a coleopteran pest.

4. The recombinant polypeptide of claim 3, wherein said pesticidal activity is against a rootworm pest.

5. The recombinant polypeptide of claim 4, wherein said rootworm is Western corn rootworm or Southern corn rootworm.

6. The polypeptide of claim 1 further comprising heterologous amino acid sequences.

7. A composition comprising the polypeptide of claim 1.

8. The composition of claim 7, wherein said composition is selected from the group consisting of a powder, dust, pellet, granule, spray, emulsion, colloid, and solution.

9. The composition of claim 8, wherein said composition is prepared by desiccation, lyophilization, homogenization, extraction, filtration, centrifugation, sedimentation, or concentration of a culture of *Bacillus thuringiensis* cells.

10. The composition of claim 8, comprising from about 1% to about 99% by weight of said polypeptide.

11. A method for controlling a coleopteran pest population comprising contacting said population with a pesticidally-effective amount of the polypeptide of claim 1.

12. A method for killing a coleopteran pest comprising contacting said pest with, or feeding to said pest, a pesticidally-effective amount of the polypeptide of claim 1.

* * * * *